(12) United States Patent
Yates et al.

(10) Patent No.: US 10,751,109 B2
(45) Date of Patent: Aug. 25, 2020

(54) HIGH POWER BATTERY POWERED RF AMPLIFIER TOPOLOGY

(71) Applicant: Ethicon LLC, Guaynabo, PR (US)

(72) Inventors: David C. Yates, West Chester, OH (US); Gavin M. Monson, Oxford, OH (US)

(73) Assignee: Ethicon LLC, Guaynabo, PR (US)

( * ) Notice: Subject to any disclaimer, the term of this patent is extended or adjusted under 35 U.S.C. 154(b) by 0 days.

(21) Appl. No.: 16/021,493

(22) Filed: Jun. 28, 2018

(65) Prior Publication Data
US 2018/0368906 A1 Dec. 27, 2018

Related U.S. Application Data

(63) Continuation of application No. 14/579,543, filed on Dec. 22, 2014, now Pat. No. 10,159,524.

(51) Int. Cl.
*H03F 3/217* (2006.01)
*A61B 18/12* (2006.01)
(Continued)

(52) U.S. Cl.
CPC ..... *A61B 18/1206* (2013.01); *H02M 7/53806* (2013.01); *H03F 1/0277* (2013.01);
(Continued)

(58) Field of Classification Search
CPC .......... A61B 18/1206; A61B 2018/124; A61B 2018/1286; A61B 2018/1226; H02M 7/53806; H02M 5/12; H03F 3/2173; H03F 3/193; H03F 1/0277; H03F 3/2171; H03F 3/26; H03F 3/217; H03F 2200/541;
(Continued)

(56) References Cited

U.S. PATENT DOCUMENTS

| | | |
|---|---|---|
| 2,366,274 A | 1/1945 | Luth et al. |
| 2,458,152 A | 1/1949 | Eakins |

(Continued)

FOREIGN PATENT DOCUMENTS

| | | |
|---|---|---|
| CN | 1634601 A | 7/2005 |
| CN | 1922563 A | 2/2007 |

(Continued)

OTHER PUBLICATIONS

Technology Overview, printed from www.harmonicscalpel.com, Internet site, website accessed on Jun. 13, 2007, (3 pages).

(Continued)

*Primary Examiner* — Khanh V Nguyen

(57) ABSTRACT

In various embodiments, a control circuit for a radio frequency drive of an electrosurgical device is disclosed comprising a voltage data input configured to receive voltage data, a current data input configured to receive current data, and a switching signal output configured to source a switching signal. The control circuit is configured to adjust a frequency of the switching signal based on the voltage data and the current data. The radio frequency drive comprising a transformer comprising a first tap, a second tap, a third tap, a first portion of a primary coil, a second portion of the primary coil, and a secondary coil. Two of the first, second, and third taps are selected to drive the primary coil between the two selected taps.

19 Claims, 10 Drawing Sheets

(51) Int. Cl.
*H03F 1/02* (2006.01)
*H03F 3/193* (2006.01)
*H02M 7/538* (2007.01)
*H03F 3/26* (2006.01)
*H02M 5/12* (2006.01)
*H02P 13/06* (2006.01)
*H01F 29/02* (2006.01)

(52) U.S. Cl.
CPC ........... *H03F 3/193* (2013.01); *H03F 3/2173* (2013.01); *A61B 2018/124* (2013.01); *A61B 2018/1226* (2013.01); *A61B 2018/1286* (2013.01); *H01F 29/02* (2013.01); *H02M 5/12* (2013.01); *H02P 13/06* (2013.01); *H03F 3/217* (2013.01); *H03F 3/2171* (2013.01); *H03F 3/26* (2013.01); *H03F 2200/451* (2013.01); *H03F 2200/541* (2013.01)

(58) Field of Classification Search
CPC ......... H03F 2200/451; H03F 2200/351; H01F 29/02; H02P 13/06
USPC .............................................. 330/251, 207 A
See application file for complete search history.

(56) References Cited

U.S. PATENT DOCUMENTS

| | | |
|---|---|---|
| 2,510,693 A | 6/1950 | Green |
| 2,736,960 A | 3/1956 | Armstrong |
| 2,849,788 A | 9/1958 | Creek |
| 2,867,039 A | 1/1959 | Zach |
| 3,015,961 A | 1/1962 | Roney |
| 3,043,309 A | 7/1962 | McCarthy |
| 3,166,971 A | 1/1965 | Stoecker |
| 3,358,676 A | 12/1967 | Frei et al. |
| 3,525,912 A | 8/1970 | Wallin |
| 3,526,219 A | 9/1970 | Balamuth |
| 3,580,841 A | 5/1971 | Cadotte et al. |
| 3,614,484 A | 10/1971 | Shoh |
| 3,636,943 A | 1/1972 | Balamuth |
| 3,703,651 A | 11/1972 | Blowers |
| 3,710,399 A | 1/1973 | Hurst |
| 3,776,238 A | 12/1973 | Peyman et al. |
| 3,777,760 A | 12/1973 | Essner |
| 3,805,787 A | 4/1974 | Banko |
| 3,862,630 A | 1/1975 | Balamuth |
| 3,900,823 A | 8/1975 | Sokal et al. |
| 3,906,217 A | 9/1975 | Lackore |
| 3,918,442 A | 11/1975 | Nikolaev et al. |
| 3,946,738 A | 3/1976 | Newton et al. |
| 3,955,859 A | 5/1976 | Stella et al. |
| 3,956,826 A | 5/1976 | Perdreaux, Jr. |
| 3,988,535 A | 10/1976 | Hickman et al. |
| 4,005,714 A | 2/1977 | Hiltebrandt |
| 4,034,762 A | 7/1977 | Cosens et al. |
| 4,047,136 A | 9/1977 | Satto |
| 4,058,126 A | 11/1977 | Leveen |
| 4,063,561 A | 12/1977 | McKenna |
| 4,099,192 A | 7/1978 | Aizawa et al. |
| 4,156,187 A | 5/1979 | Murry et al. |
| 4,188,927 A | 2/1980 | Harris |
| 4,200,106 A | 4/1980 | Douvas et al. |
| 4,203,430 A | 5/1980 | Takahashi |
| 4,220,154 A | 9/1980 | Semm |
| 4,237,441 A | 12/1980 | van Konynenburg et al. |
| 4,278,077 A | 7/1981 | Mizumoto |
| 4,281,785 A | 8/1981 | Brooks |
| 4,304,987 A | 12/1981 | van Konynenburg |
| 4,314,559 A | 2/1982 | Allen |
| 4,384,584 A | 5/1983 | Chen |
| 4,445,063 A | 4/1984 | Smith |
| 4,463,759 A | 8/1984 | Garito et al. |
| 4,491,132 A | 1/1985 | Aikins |
| 4,492,231 A | 1/1985 | Auth |
| 4,535,773 A | 8/1985 | Yoon |
| 4,545,926 A | 10/1985 | Fouts, Jr. et al. |
| 4,550,870 A | 11/1985 | Krumme et al. |
| 4,582,236 A | 4/1986 | Hirose |
| 4,585,282 A | 4/1986 | Bosley |
| 4,597,390 A | 7/1986 | Mulhollan et al. |
| 4,617,927 A | 10/1986 | Manes |
| 4,633,874 A | 1/1987 | Chow et al. |
| 4,634,420 A | 1/1987 | Spinosa et al. |
| 4,640,279 A | 2/1987 | Beard |
| 4,655,746 A | 4/1987 | Daniels et al. |
| 4,671,287 A | 6/1987 | Fiddian-Green |
| 4,708,127 A | 11/1987 | Abdelghani |
| 4,735,603 A | 4/1988 | Goodson et al. |
| 4,761,871 A | 8/1988 | O'Connor et al. |
| 4,777,951 A | 10/1988 | Cribier et al. |
| 4,797,803 A | 1/1989 | Carroll |
| 4,798,588 A | 1/1989 | Aillon |
| 4,802,461 A | 2/1989 | Cho |
| 4,803,506 A | 2/1989 | Diehl et al. |
| 4,830,462 A | 5/1989 | Karny et al. |
| 4,832,683 A | 5/1989 | Idemoto et al. |
| 4,838,853 A | 6/1989 | Parisi |
| 4,849,133 A | 7/1989 | Yoshida et al. |
| 4,850,354 A | 7/1989 | McGurk-Burleson et al. |
| 4,860,745 A | 8/1989 | Farin et al. |
| 4,865,159 A | 9/1989 | Jamison |
| 4,878,493 A | 11/1989 | Pasternak et al. |
| 4,880,015 A | 11/1989 | Nierman |
| 4,896,009 A | 1/1990 | Pawlowski |
| 4,910,389 A | 3/1990 | Sherman et al. |
| 4,910,633 A | 3/1990 | Quinn |
| 4,911,148 A | 3/1990 | Sosnowski et al. |
| 4,919,129 A | 4/1990 | Weber, Jr. et al. |
| 4,920,978 A | 5/1990 | Colvin |
| 4,922,902 A | 5/1990 | Wuchinich et al. |
| 4,936,842 A | 6/1990 | D'Amelio et al. |
| 4,961,738 A | 10/1990 | Mackin |
| 4,967,670 A | 11/1990 | Morishita et al. |
| 4,981,756 A | 1/1991 | Rhandhawa |
| 5,007,919 A | 4/1991 | Silva et al. |
| 5,019,075 A | 5/1991 | Spears et al. |
| 5,020,514 A | 6/1991 | Heckele |
| 5,026,387 A | 6/1991 | Thomas |
| 5,061,269 A | 10/1991 | Muller |
| 5,093,754 A | 3/1992 | Kawashima |
| 5,099,216 A | 3/1992 | Pelrine |
| 5,099,840 A | 3/1992 | Goble et al. |
| 5,104,025 A | 4/1992 | Main et al. |
| 5,106,538 A | 4/1992 | Barma et al. |
| 5,108,383 A | 4/1992 | White |
| 5,112,300 A | 5/1992 | Ureche |
| 5,123,903 A | 6/1992 | Quaid et al. |
| 5,150,102 A | 9/1992 | Takashima |
| 5,150,272 A | 9/1992 | Danley et al. |
| 5,156,633 A | 10/1992 | Smith |
| 5,160,334 A | 11/1992 | Billings et al. |
| 5,162,044 A | 11/1992 | Gahn et al. |
| 5,167,725 A | 12/1992 | Clark et al. |
| D332,660 S | 1/1993 | Rawson et al. |
| 5,176,695 A | 1/1993 | Dulebohn |
| 5,184,605 A | 2/1993 | Grzeszykowski |
| 5,188,102 A | 2/1993 | Idemoto et al. |
| 5,190,541 A | 3/1993 | Abele et al. |
| 5,196,007 A | 3/1993 | Ellman et al. |
| 5,205,459 A | 4/1993 | Brinkerhoff et al. |
| 5,205,817 A | 4/1993 | Idemoto et al. |
| 5,209,719 A | 5/1993 | Baruch et al. |
| 5,213,569 A | 5/1993 | Davis |
| 5,217,460 A | 6/1993 | Knoepfler |
| 5,221,282 A | 6/1993 | Wuchinich |
| 5,226,910 A | 7/1993 | Kajiyama et al. |
| 5,234,428 A | 8/1993 | Kaufman |
| 5,241,236 A | 8/1993 | Sasaki et al. |
| 5,253,647 A | 10/1993 | Takahashi et al. |
| 5,254,130 A | 10/1993 | Poncet et al. |
| 5,257,988 A | 11/1993 | L'Esperance, Jr. |
| 5,258,004 A | 11/1993 | Bales et al. |
| 5,258,006 A | 11/1993 | Rydell et al. |

(56) References Cited

U.S. PATENT DOCUMENTS

| | | |
|---|---|---|
| 5,261,922 A | 11/1993 | Hood |
| 5,263,957 A | 11/1993 | Davison |
| 5,267,091 A | 11/1993 | Chen |
| 5,282,800 A | 2/1994 | Foshee et al. |
| 5,285,945 A | 2/1994 | Brinkerhoff et al. |
| 5,290,286 A | 3/1994 | Parins |
| 5,293,863 A | 3/1994 | Zhu et al. |
| 5,304,115 A | 4/1994 | Pflueger et al. |
| D347,474 S | 5/1994 | Olson |
| 5,309,927 A | 5/1994 | Welch |
| 5,312,023 A | 5/1994 | Green et al. |
| 5,313,306 A | 5/1994 | Kuban et al. |
| 5,318,563 A | 6/1994 | Malis et al. |
| 5,318,564 A | 6/1994 | Eggers |
| 5,318,565 A | 6/1994 | Kuriloff et al. |
| 5,318,570 A | 6/1994 | Hood et al. |
| 5,318,589 A | 6/1994 | Lichtman |
| 5,322,055 A | 6/1994 | Davison et al. |
| 5,324,260 A | 6/1994 | O'Neill et al. |
| 5,324,299 A | 6/1994 | Davison et al. |
| 5,326,013 A | 7/1994 | Green et al. |
| 5,330,471 A | 7/1994 | Eggers |
| 5,330,502 A | 7/1994 | Hassler et al. |
| 5,333,624 A | 8/1994 | Tovey |
| 5,339,723 A | 8/1994 | Huitema |
| 5,342,359 A | 8/1994 | Rydell |
| 5,344,420 A | 9/1994 | Hilal et al. |
| 5,346,502 A | 9/1994 | Estabrook et al. |
| 5,352,219 A | 10/1994 | Reddy |
| 5,359,992 A | 11/1994 | Hori et al. |
| 5,361,583 A | 11/1994 | Huitema |
| 5,366,466 A | 11/1994 | Christian et al. |
| 5,370,640 A | 12/1994 | Kolff |
| D354,564 S | 1/1995 | Medema |
| 5,381,067 A | 1/1995 | Greenstein et al. |
| 5,383,874 A | 1/1995 | Jackson et al. |
| 5,387,207 A | 2/1995 | Dyer et al. |
| 5,389,098 A | 2/1995 | Tsuruta et al. |
| 5,395,033 A | 3/1995 | Byrne et al. |
| 5,395,312 A | 3/1995 | Desai |
| 5,395,331 A | 3/1995 | O'Neill et al. |
| 5,395,363 A | 3/1995 | Billings et al. |
| 5,395,364 A | 3/1995 | Anderhub et al. |
| 5,396,266 A | 3/1995 | Brimhall |
| 5,396,900 A | 3/1995 | Slater et al. |
| 5,403,312 A | 4/1995 | Yates et al. |
| 5,409,483 A | 4/1995 | Campbell et al. |
| D358,887 S | 5/1995 | Feinberg |
| 5,411,481 A | 5/1995 | Allen et al. |
| 5,413,575 A | 5/1995 | Haenggi |
| 5,417,709 A | 5/1995 | Slater |
| 5,419,761 A | 5/1995 | Narayanan et al. |
| 5,421,829 A | 6/1995 | Olichney et al. |
| 5,428,504 A | 6/1995 | Bhatla |
| 5,429,131 A | 7/1995 | Scheinman et al. |
| 5,431,640 A | 7/1995 | Gabriel |
| 5,443,463 A | 8/1995 | Stern et al. |
| 5,445,615 A | 8/1995 | Yoon |
| 5,445,638 A | 8/1995 | Rydell et al. |
| 5,449,370 A | 9/1995 | Vaitekunas |
| 5,451,227 A | 9/1995 | Michaelson |
| 5,456,684 A | 10/1995 | Schmidt et al. |
| 5,458,598 A | 10/1995 | Feinberg et al. |
| 5,462,604 A | 10/1995 | Shibano et al. |
| 5,465,895 A | 11/1995 | Knodel et al. |
| 5,472,443 A | 12/1995 | Cordis et al. |
| 5,476,479 A | 12/1995 | Green et al. |
| 5,477,788 A | 12/1995 | Morishita |
| 5,478,003 A | 12/1995 | Green et al. |
| 5,480,409 A | 1/1996 | Riza |
| 5,483,501 A | 1/1996 | Park et al. |
| 5,484,436 A | 1/1996 | Eggers et al. |
| 5,486,162 A | 1/1996 | Brumbach |
| 5,486,189 A | 1/1996 | Mudry et al. |
| 5,489,256 A | 2/1996 | Adair |
| 5,496,317 A | 3/1996 | Goble et al. |
| 5,500,216 A | 3/1996 | Julian et al. |
| 5,501,654 A | 3/1996 | Failla et al. |
| 5,504,650 A | 4/1996 | Katsui et al. |
| 5,505,693 A | 4/1996 | Mackool |
| 5,509,922 A | 4/1996 | Aranyi et al. |
| 5,511,556 A | 4/1996 | DeSantis |
| 5,520,704 A | 5/1996 | Castro et al. |
| 5,522,839 A | 6/1996 | Pilling |
| 5,531,744 A | 7/1996 | Nardella et al. |
| 5,540,648 A | 7/1996 | Yoon |
| 5,540,681 A | 7/1996 | Strul et al. |
| 5,542,916 A | 8/1996 | Hirsch et al. |
| 5,542,938 A | 8/1996 | Avellanet et al. |
| 5,558,671 A | 9/1996 | Yates |
| 5,562,609 A | 10/1996 | Brumbach |
| 5,562,610 A | 10/1996 | Brumbach |
| 5,562,657 A | 10/1996 | Griffin |
| 5,563,179 A | 10/1996 | Stone et al. |
| 5,569,164 A | 10/1996 | Lurz |
| 5,571,121 A | 11/1996 | Heifetz |
| 5,573,534 A | 11/1996 | Stone |
| 5,584,830 A | 12/1996 | Ladd et al. |
| 5,599,350 A | 2/1997 | Schulze et al. |
| 5,601,601 A | 2/1997 | Tal et al. |
| 5,604,531 A | 2/1997 | Iddan et al. |
| 5,607,436 A | 3/1997 | Pratt et al. |
| 5,607,450 A | 3/1997 | Zvenyatsky et al. |
| 5,611,813 A | 3/1997 | Lichtman |
| 5,618,307 A | 4/1997 | Donlon et al. |
| 5,618,492 A | 4/1997 | Auten et al. |
| 5,624,452 A | 4/1997 | Yates |
| 5,626,578 A | 5/1997 | Tihon |
| 5,628,760 A | 5/1997 | Knoepfler |
| 5,630,420 A | 5/1997 | Vaitekunas |
| 5,632,432 A | 5/1997 | Schulze et al. |
| D381,077 S | 7/1997 | Hunt |
| 5,643,175 A | 7/1997 | Adair |
| 5,645,065 A | 7/1997 | Shapiro et al. |
| 5,647,871 A | 7/1997 | Levine et al. |
| 5,651,780 A | 7/1997 | Jackson et al. |
| 5,653,677 A | 8/1997 | Okada et al. |
| 5,653,713 A | 8/1997 | Michelson |
| 5,657,697 A | 8/1997 | Murai |
| 5,658,281 A | 8/1997 | Heard |
| 5,662,667 A | 9/1997 | Knodel |
| 5,665,085 A | 9/1997 | Nardella |
| 5,665,100 A | 9/1997 | Yoon |
| 5,669,922 A | 9/1997 | Hood |
| 5,674,219 A | 10/1997 | Monson et al. |
| 5,674,220 A | 10/1997 | Fox et al. |
| 5,674,235 A | 10/1997 | Parisi |
| 5,681,260 A | 10/1997 | Ueda et al. |
| 5,688,270 A | 11/1997 | Yates et al. |
| 5,690,269 A | 11/1997 | Bolanos et al. |
| 5,693,051 A | 12/1997 | Schulze et al. |
| 5,694,936 A | 12/1997 | Fujimoto et al. |
| 5,700,243 A | 12/1997 | Narciso, Jr. |
| 5,700,261 A | 12/1997 | Brinkerhoff |
| 5,704,900 A | 1/1998 | Dobrovolny et al. |
| 5,709,680 A | 1/1998 | Yates et al. |
| 5,711,472 A | 1/1998 | Bryan |
| 5,713,896 A | 2/1998 | Nardella |
| 5,716,366 A | 2/1998 | Yates |
| 5,720,742 A | 2/1998 | Zacharias |
| 5,720,744 A | 2/1998 | Eggleston et al. |
| 5,722,326 A | 3/1998 | Post |
| 5,722,426 A | 3/1998 | Kolff |
| 5,732,636 A | 3/1998 | Wang et al. |
| 5,733,074 A | 3/1998 | Stock et al. |
| 5,735,848 A | 4/1998 | Yates et al. |
| 5,738,652 A | 4/1998 | Boyd et al. |
| 5,741,226 A | 4/1998 | Strukel et al. |
| 5,741,305 A | 4/1998 | Vincent et al. |
| 5,743,906 A | 4/1998 | Parins et al. |
| 5,752,973 A | 5/1998 | Kieturakis |
| 5,755,717 A | 5/1998 | Yates et al. |
| 5,762,255 A | 6/1998 | Chrisman et al. |
| 5,776,130 A | 7/1998 | Buysse et al. |

(56) References Cited

U.S. PATENT DOCUMENTS

| | | |
|---|---|---|
| 5,779,701 A | 7/1998 | McBrayer et al. |
| 5,782,834 A | 7/1998 | Lucey et al. |
| 5,792,135 A | 8/1998 | Madhani et al. |
| 5,792,138 A | 8/1998 | Shipp |
| 5,796,188 A | 8/1998 | Bays |
| 5,797,941 A | 8/1998 | Schulze et al. |
| 5,800,432 A | 9/1998 | Swanson |
| 5,800,449 A | 9/1998 | Wales |
| 5,805,140 A | 9/1998 | Rosenberg et al. |
| 5,807,393 A | 9/1998 | Williamson, IV et al. |
| 5,810,718 A | 9/1998 | Akiba et al. |
| 5,810,811 A | 9/1998 | Yates et al. |
| 5,810,859 A | 9/1998 | DiMatteo et al. |
| 5,817,033 A | 10/1998 | DeSantis et al. |
| 5,817,084 A | 10/1998 | Jensen |
| 5,817,093 A | 10/1998 | Williamson, IV et al. |
| 5,827,323 A | 10/1998 | Klieman et al. |
| 5,828,160 A | 10/1998 | Sugishita |
| 5,836,867 A | 11/1998 | Speier et al. |
| 5,836,909 A | 11/1998 | Cosmescu |
| 5,836,943 A | 11/1998 | Miller, III |
| 5,836,990 A | 11/1998 | Li |
| 5,843,109 A | 12/1998 | Mehta et al. |
| 5,853,412 A | 12/1998 | Mayenberger |
| 5,876,401 A | 3/1999 | Schulze et al. |
| 5,878,193 A | 3/1999 | Wang et al. |
| 5,879,364 A | 3/1999 | Bromfield et al. |
| 5,880,668 A | 3/1999 | Hall |
| 5,883,454 A | 3/1999 | Hones et al. |
| 5,887,018 A | 3/1999 | Bayazitoglu et al. |
| 5,891,142 A | 4/1999 | Eggers et al. |
| 5,893,835 A | 4/1999 | Witt et al. |
| 5,897,569 A | 4/1999 | Kellogg et al. |
| 5,902,239 A | 5/1999 | Buurman |
| 5,904,147 A | 5/1999 | Conlan et al. |
| 5,906,579 A | 5/1999 | Vander Salm et al. |
| 5,906,625 A | 5/1999 | Bito et al. |
| 5,910,129 A | 6/1999 | Koblish et al. |
| 5,921,956 A | 7/1999 | Grinberg et al. |
| 5,929,846 A | 7/1999 | Rosenberg et al. |
| 5,935,143 A | 8/1999 | Hood |
| 5,935,144 A | 8/1999 | Estabrook |
| 5,938,633 A | 8/1999 | Beaupre |
| 5,944,298 A | 8/1999 | Koike |
| 5,944,718 A | 8/1999 | Austin et al. |
| 5,944,737 A | 8/1999 | Tsonton et al. |
| 5,954,736 A | 9/1999 | Bishop et al. |
| 5,954,746 A | 9/1999 | Holthaus et al. |
| 5,957,849 A | 9/1999 | Munro |
| 5,957,882 A | 9/1999 | Nita et al. |
| 5,957,943 A | 9/1999 | Vaitekunas |
| 5,968,007 A | 10/1999 | Simon et al. |
| 5,968,060 A | 10/1999 | Kellogg |
| D416,089 S | 11/1999 | Barton et al. |
| 5,984,938 A | 11/1999 | Yoon |
| 5,989,182 A | 11/1999 | Hori et al. |
| 5,989,274 A | 11/1999 | Davison et al. |
| 5,989,275 A | 11/1999 | Estabrook et al. |
| 5,993,972 A | 11/1999 | Reich et al. |
| 6,003,517 A | 12/1999 | Sheffield et al. |
| 6,007,484 A | 12/1999 | Thompson |
| 6,013,052 A | 1/2000 | Durman et al. |
| 6,014,580 A | 1/2000 | Blume et al. |
| 6,024,741 A | 2/2000 | Williamson, IV et al. |
| 6,024,744 A | 2/2000 | Kese et al. |
| 6,033,375 A | 3/2000 | Brumbach |
| 6,033,399 A | 3/2000 | Gines |
| 6,039,734 A | 3/2000 | Goble |
| 6,050,996 A | 4/2000 | Schmaltz et al. |
| 6,053,172 A | 4/2000 | Hovda et al. |
| 6,063,098 A | 5/2000 | Houser et al. |
| 6,066,132 A | 5/2000 | Chen et al. |
| 6,068,629 A | 5/2000 | Haissaguerre et al. |
| 6,068,647 A | 5/2000 | Witt et al. |
| 6,074,389 A | 6/2000 | Levine et al. |
| 6,077,285 A | 6/2000 | Boukhny |
| 6,080,152 A | 6/2000 | Nardella et al. |
| 6,083,151 A | 7/2000 | Renner et al. |
| 6,083,191 A | 7/2000 | Rose |
| 6,086,584 A | 7/2000 | Miller |
| 6,090,120 A | 7/2000 | Wright et al. |
| 6,091,995 A | 7/2000 | Ingle et al. |
| 6,099,483 A | 8/2000 | Palmer et al. |
| 6,099,550 A | 8/2000 | Yoon |
| 6,109,500 A | 8/2000 | Alli et al. |
| 6,113,594 A | 9/2000 | Savage |
| 6,113,598 A | 9/2000 | Baker |
| 6,123,466 A | 9/2000 | Persson et al. |
| H001904 H | 10/2000 | Yates et al. |
| 6,127,757 A | 10/2000 | Swinbanks |
| 6,132,368 A | 10/2000 | Cooper |
| 6,139,320 A | 10/2000 | Hahn |
| 6,144,402 A | 11/2000 | Norsworthy et al. |
| 6,152,902 A | 11/2000 | Christian et al. |
| 6,152,923 A | 11/2000 | Ryan |
| 6,154,198 A | 11/2000 | Rosenberg |
| 6,159,160 A | 12/2000 | Hsei et al. |
| 6,159,175 A | 12/2000 | Strukel et al. |
| 6,162,208 A | 12/2000 | Hipps |
| 6,173,199 B1 | 1/2001 | Gabriel |
| 6,173,715 B1 | 1/2001 | Sinanan et al. |
| 6,174,309 B1 | 1/2001 | Wrublewski et al. |
| 6,176,857 B1 | 1/2001 | Ashley |
| 6,190,386 B1 | 2/2001 | Rydell |
| 6,206,844 B1 | 3/2001 | Reichel et al. |
| 6,206,876 B1 | 3/2001 | Levine et al. |
| 6,206,877 B1 | 3/2001 | Kese et al. |
| 6,210,403 B1 | 4/2001 | Klicek |
| 6,214,023 B1 | 4/2001 | Whipple et al. |
| 6,219,572 B1 | 4/2001 | Young |
| 6,221,007 B1 | 4/2001 | Green |
| 6,228,080 B1 | 5/2001 | Gines |
| 6,231,565 B1 | 5/2001 | Tovey et al. |
| 6,233,476 B1 | 5/2001 | Strommer et al. |
| 6,238,366 B1 | 5/2001 | Savage et al. |
| 6,241,724 B1 | 6/2001 | Fleischman et al. |
| 6,248,074 B1 | 6/2001 | Ohno et al. |
| D444,365 S | 7/2001 | Bass et al. |
| 6,254,623 B1 | 7/2001 | Haibel, Jr. et al. |
| 6,258,034 B1 | 7/2001 | Hanafy |
| 6,258,086 B1 | 7/2001 | Ashley et al. |
| 6,259,230 B1 | 7/2001 | Chou |
| 6,267,761 B1 | 7/2001 | Ryan |
| 6,270,831 B2 | 8/2001 | Kumar et al. |
| 6,273,852 B1 | 8/2001 | Lehe et al. |
| 6,273,887 B1 | 8/2001 | Yamauchi et al. |
| 6,274,963 B1 | 8/2001 | Estabrook et al. |
| 6,277,115 B1 | 8/2001 | Saadat |
| 6,277,117 B1 | 8/2001 | Tetzlaff et al. |
| 6,278,218 B1 | 8/2001 | Madan et al. |
| 6,283,981 B1 | 9/2001 | Beaupre |
| 6,292,700 B1 | 9/2001 | Morrison et al. |
| 6,309,400 B2 | 10/2001 | Beaupre |
| 6,315,789 B1 | 11/2001 | Cragg |
| 6,319,221 B1 | 11/2001 | Savage et al. |
| 6,325,799 B1 | 12/2001 | Goble |
| 6,325,811 B1 | 12/2001 | Messerly |
| 6,328,751 B1 | 12/2001 | Beaupre |
| 6,340,878 B1 | 1/2002 | Oglesbee |
| 6,352,532 B1 | 3/2002 | Kramer et al. |
| 6,364,888 B1 | 4/2002 | Niemeyer et al. |
| 6,371,952 B1 | 4/2002 | Madhani et al. |
| 6,379,320 B1 | 4/2002 | Lafon et al. |
| D457,958 S | 5/2002 | Dycus et al. |
| 6,383,194 B1 | 5/2002 | Pothula |
| 6,387,094 B1 | 5/2002 | Eitenmuller |
| 6,387,109 B1 | 5/2002 | Davison et al. |
| 6,388,657 B1 | 5/2002 | Natoli |
| 6,391,026 B1 | 5/2002 | Hung et al. |
| 6,391,042 B1 | 5/2002 | Cimino |
| 6,398,779 B1 | 6/2002 | Buysse et al. |
| 6,409,722 B1 | 6/2002 | Hoey et al. |
| H002037 H | 7/2002 | Yates et al. |
| 6,416,469 B1 | 7/2002 | Phung et al. |

(56) References Cited

U.S. PATENT DOCUMENTS

| | | |
|---|---|---|
| 6,416,486 B1 | 7/2002 | Wampler |
| 6,419,675 B1 | 7/2002 | Gallo, Sr. |
| 6,423,073 B2 | 7/2002 | Bowman |
| 6,423,082 B1 | 7/2002 | Houser et al. |
| 6,430,446 B1 | 8/2002 | Knowlton |
| 6,432,118 B1 | 8/2002 | Messerly |
| 6,436,114 B1 | 8/2002 | Novak et al. |
| 6,436,115 B1 | 8/2002 | Beaupre |
| 6,443,968 B1 | 9/2002 | Holthaus et al. |
| 6,443,969 B1 | 9/2002 | Novak et al. |
| 6,454,781 B1 | 9/2002 | Witt et al. |
| 6,454,782 B1 | 9/2002 | Schwemberger |
| 6,458,128 B1 | 10/2002 | Schulze |
| 6,458,130 B1 | 10/2002 | Frazier et al. |
| 6,458,142 B1 | 10/2002 | Faller et al. |
| 6,461,363 B1 | 10/2002 | Gadberry et al. |
| 6,464,689 B1 | 10/2002 | Qin et al. |
| 6,464,702 B2 | 10/2002 | Schulze et al. |
| 6,464,703 B2 | 10/2002 | Bartel |
| 6,471,172 B1 | 10/2002 | Lemke et al. |
| 6,475,211 B2 | 11/2002 | Chess et al. |
| 6,475,216 B2 | 11/2002 | Mulier et al. |
| 6,480,796 B2 | 11/2002 | Wiener |
| 6,485,490 B2 | 11/2002 | Wampler et al. |
| 6,491,690 B1 | 12/2002 | Goble et al. |
| 6,491,691 B1 | 12/2002 | Morley et al. |
| 6,491,701 B2 | 12/2002 | Tierney et al. |
| 6,491,708 B2 | 12/2002 | Madan et al. |
| 6,497,715 B2 | 12/2002 | Satou |
| 6,500,112 B1 | 12/2002 | Khouri |
| 6,500,176 B1 | 12/2002 | Truckai et al. |
| 6,500,188 B2 | 12/2002 | Harper et al. |
| 6,503,248 B1 | 1/2003 | Levine |
| 6,506,208 B2 | 1/2003 | Hunt et al. |
| 6,511,480 B1 | 1/2003 | Tetzlaff et al. |
| 6,514,252 B2 | 2/2003 | Nezhat et al. |
| 6,517,565 B1 | 2/2003 | Whitman et al. |
| 6,520,960 B2 | 2/2003 | Blocher et al. |
| 6,522,909 B1 | 2/2003 | Garibaldi et al. |
| 6,524,316 B1 | 2/2003 | Nicholson et al. |
| 6,531,846 B1 | 3/2003 | Smith |
| 6,533,784 B2 | 3/2003 | Truckai et al. |
| 6,537,196 B1 | 3/2003 | Creighton, IV et al. |
| 6,537,272 B2 | 3/2003 | Christopherson et al. |
| 6,537,291 B2 | 3/2003 | Friedman et al. |
| 6,540,693 B2 | 4/2003 | Burbank et al. |
| 6,543,456 B1 | 4/2003 | Freeman |
| 6,544,260 B1 | 4/2003 | Markel et al. |
| 6,551,309 B1 | 4/2003 | LePivert |
| 6,554,829 B2 | 4/2003 | Schulze et al. |
| 6,558,376 B2 | 5/2003 | Bishop |
| 6,561,983 B2 | 5/2003 | Cronin et al. |
| 6,562,037 B2 | 5/2003 | Paton et al. |
| 6,572,632 B2 | 6/2003 | Zisterer et al. |
| 6,572,639 B2 | 6/2003 | Ingle et al. |
| 6,575,969 B1 | 6/2003 | Rittman, III et al. |
| 6,582,451 B1 | 6/2003 | Marucci et al. |
| 6,584,360 B2 | 6/2003 | Francischelli et al. |
| 6,585,735 B1 | 7/2003 | Frazier et al. |
| 6,589,200 B1 | 7/2003 | Schwemberger et al. |
| 6,589,239 B2 | 7/2003 | Khandkar et al. |
| 6,594,517 B1 | 7/2003 | Nevo |
| 6,599,321 B2 | 7/2003 | Hyde, Jr. |
| 6,602,252 B2 | 8/2003 | Mollenauer |
| 6,610,060 B2 | 8/2003 | Mulier et al. |
| 6,616,450 B2 | 9/2003 | Mossle et al. |
| 6,616,600 B2 | 9/2003 | Pauker |
| 6,619,529 B2 | 9/2003 | Green et al. |
| 6,620,129 B2 | 9/2003 | Stecker et al. |
| 6,620,161 B2 | 9/2003 | Schulze et al. |
| 6,622,731 B2 | 9/2003 | Daniel et al. |
| 6,623,482 B2 | 9/2003 | Pendekanti et al. |
| 6,623,501 B2 | 9/2003 | Heller et al. |
| 6,626,926 B2 | 9/2003 | Friedman et al. |
| 6,633,234 B2 | 10/2003 | Wiener et al. |
| 6,635,057 B2 | 10/2003 | Harano et al. |
| 6,644,532 B2 | 11/2003 | Green et al. |
| 6,648,817 B2 | 11/2003 | Schara et al. |
| 6,651,669 B1 | 11/2003 | Burnside |
| 6,656,177 B2 | 12/2003 | Truckai et al. |
| 6,656,198 B2 | 12/2003 | Tsonton et al. |
| 6,662,127 B2 | 12/2003 | Wiener et al. |
| 6,663,941 B2 | 12/2003 | Brown et al. |
| 6,673,248 B2 | 1/2004 | Chowdhury |
| 6,676,660 B2 | 1/2004 | Wampler et al. |
| 6,678,621 B2 | 1/2004 | Wiener et al. |
| 6,679,882 B1 | 1/2004 | Kornerup |
| 6,679,899 B2 | 1/2004 | Wiener et al. |
| 6,682,501 B1 | 1/2004 | Nelson et al. |
| 6,682,544 B2 | 1/2004 | Mastri et al. |
| 6,695,840 B2 | 2/2004 | Schulze |
| 6,716,215 B1 | 4/2004 | David et al. |
| 6,719,684 B2 | 4/2004 | Kim et al. |
| 6,719,765 B2 | 4/2004 | Bonutti |
| 6,722,552 B2 | 4/2004 | Fenton, Jr. |
| 6,726,686 B2 | 4/2004 | Buysse et al. |
| 6,731,047 B2 | 5/2004 | Kauf et al. |
| 6,733,498 B2 | 5/2004 | Paton et al. |
| 6,733,506 B1 | 5/2004 | McDevitt et al. |
| 6,736,813 B2 | 5/2004 | Yamauchi et al. |
| 6,743,229 B2 | 6/2004 | Buysse et al. |
| 6,746,443 B1 | 6/2004 | Morley et al. |
| 6,752,815 B2 | 6/2004 | Beaupre |
| 6,762,535 B2 | 7/2004 | Take et al. |
| 6,766,202 B2 | 7/2004 | Underwood et al. |
| 6,767,349 B2 | 7/2004 | Ouchi |
| 6,770,072 B1 | 8/2004 | Truckai et al. |
| 6,773,409 B2 | 8/2004 | Truckai et al. |
| 6,773,434 B2 | 8/2004 | Ciarrocca |
| 6,773,435 B2 | 8/2004 | Schulze et al. |
| 6,773,444 B2 | 8/2004 | Messerly |
| 6,775,575 B2 | 8/2004 | Bommannan et al. |
| 6,776,165 B2 | 8/2004 | Jin |
| 6,783,524 B2 | 8/2004 | Anderson et al. |
| 6,786,382 B1 | 9/2004 | Hoffman |
| 6,786,383 B2 | 9/2004 | Stegelmann |
| 6,789,939 B2 | 9/2004 | Schrodinger et al. |
| 6,790,216 B1 | 9/2004 | Ishikawa |
| 6,796,981 B2 | 9/2004 | Wham et al. |
| D496,997 S | 10/2004 | Dycus et al. |
| 6,800,085 B2 | 10/2004 | Selmon et al. |
| 6,802,843 B2 | 10/2004 | Truckai et al. |
| 6,806,317 B2 | 10/2004 | Morishita et al. |
| 6,808,491 B2 | 10/2004 | Kortenbach et al. |
| 6,811,842 B1 | 11/2004 | Ehrnsperger et al. |
| 6,814,731 B2 | 11/2004 | Swanson |
| 6,817,974 B2 | 11/2004 | Cooper et al. |
| 6,821,273 B2 | 11/2004 | Mollenauer |
| 6,828,712 B2 | 12/2004 | Battaglin et al. |
| 6,832,998 B2 | 12/2004 | Goble |
| 6,835,199 B2 | 12/2004 | McGuckin, Jr. et al. |
| 6,840,938 B1 | 1/2005 | Morley et al. |
| 6,860,880 B2 | 3/2005 | Treat et al. |
| 6,869,439 B2 | 3/2005 | White et al. |
| 6,875,220 B2 | 4/2005 | Du et al. |
| 6,877,647 B2 | 4/2005 | Green et al. |
| 6,893,435 B2 | 5/2005 | Goble |
| 6,905,497 B2 | 6/2005 | Truckai et al. |
| 6,908,463 B2 | 6/2005 | Treat et al. |
| 6,908,472 B2 | 6/2005 | Wiener et al. |
| 6,913,579 B2 | 7/2005 | Truckai et al. |
| 6,926,716 B2 | 8/2005 | Baker et al. |
| 6,929,622 B2 | 8/2005 | Chian |
| 6,929,632 B2 | 8/2005 | Nita et al. |
| 6,929,644 B2 | 8/2005 | Truckai et al. |
| 6,936,003 B2 | 8/2005 | Iddan |
| D509,589 S | 9/2005 | Wells |
| 6,939,347 B2 * | 9/2005 | Thompson ......... A61B 18/1206 128/898 |
| 6,945,981 B2 | 9/2005 | Donofrio et al. |
| 6,953,461 B2 | 10/2005 | McClurken et al. |
| D511,145 S | 11/2005 | Donofrio et al. |
| 6,959,852 B2 | 11/2005 | Shelton, IV et al. |
| 6,974,462 B2 | 12/2005 | Sater |

(56) References Cited

U.S. PATENT DOCUMENTS

| | | |
|---|---|---|
| 6,976,844 B2 | 12/2005 | Hickok et al. |
| 6,976,969 B2 | 12/2005 | Messerly |
| 6,977,495 B2 | 12/2005 | Donofrio |
| 6,984,220 B2 | 1/2006 | Wuchinich |
| 6,986,738 B2 | 1/2006 | Glukhovsky et al. |
| 6,986,780 B2 | 1/2006 | Rudnick et al. |
| 6,994,709 B2 | 2/2006 | Iida |
| 7,000,818 B2 | 2/2006 | Shelton, IV et al. |
| 7,004,951 B2 | 2/2006 | Gibbens, III |
| 7,011,657 B2 | 3/2006 | Truckai et al. |
| 7,029,435 B2 | 4/2006 | Nakao |
| 7,039,453 B2 | 5/2006 | Mullick et al. |
| 7,041,083 B2 | 5/2006 | Chu et al. |
| 7,041,088 B2 | 5/2006 | Nawrocki et al. |
| 7,041,102 B2 | 5/2006 | Truckai et al. |
| 7,044,352 B2 | 5/2006 | Shelton, IV et al. |
| 7,044,937 B1 | 5/2006 | Kirwan et al. |
| 7,052,496 B2 | 5/2006 | Yamauchi |
| 7,055,731 B2 | 6/2006 | Shelton, IV et al. |
| 7,056,284 B2 | 6/2006 | Martone et al. |
| 7,063,699 B2 | 6/2006 | Hess et al. |
| 7,066,879 B2 | 6/2006 | Fowler et al. |
| 7,066,936 B2 | 6/2006 | Ryan |
| 7,070,597 B2 | 7/2006 | Truckai et al. |
| 7,074,219 B2 | 7/2006 | Levine et al. |
| 7,077,039 B2 | 7/2006 | Gass et al. |
| 7,077,853 B2 | 7/2006 | Kramer et al. |
| 7,083,579 B2 | 8/2006 | Yokoi et al. |
| 7,083,617 B2 | 8/2006 | Kortenbach et al. |
| 7,083,618 B2 | 8/2006 | Couture et al. |
| 7,083,619 B2 | 8/2006 | Truckai et al. |
| 7,087,054 B2 | 8/2006 | Truckai et al. |
| 7,090,673 B2 | 8/2006 | Dycus et al. |
| 7,094,235 B2 | 8/2006 | Francischelli |
| 7,096,560 B2 | 8/2006 | Oddsen, Jr. |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,108,695 B2 | 9/2006 | Witt et al. |
| 7,112,201 B2 | 9/2006 | Truckai et al. |
| 7,118,564 B2 | 10/2006 | Ritchie et al. |
| 7,118,570 B2 | 10/2006 | Tetzlaff et al. |
| 7,120,498 B2 | 10/2006 | Imran et al. |
| 7,124,932 B2 | 10/2006 | Isaacson et al. |
| 7,125,409 B2 | 10/2006 | Truckai et al. |
| 7,131,970 B2 | 11/2006 | Moses et al. |
| 7,131,971 B2 | 11/2006 | Dycus et al. |
| 7,135,018 B2 | 11/2006 | Ryan et al. |
| 7,135,030 B2 | 11/2006 | Schwemberger et al. |
| 7,137,980 B2 | 11/2006 | Buysse et al. |
| 7,143,925 B2 | 12/2006 | Shelton, IV et al. |
| 7,147,138 B2 | 12/2006 | Shelton, IV |
| 7,147,638 B2 | 12/2006 | Chapman et al. |
| 7,153,315 B2 | 12/2006 | Miller |
| 7,156,189 B1 | 1/2007 | Bar-Cohen et al. |
| 7,156,846 B2 | 1/2007 | Dycus et al. |
| 7,156,853 B2 | 1/2007 | Muratsu |
| 7,157,058 B2 | 1/2007 | Marhasin et al. |
| 7,159,750 B2 | 1/2007 | Racenet et al. |
| 7,160,296 B2 | 1/2007 | Pearson et al. |
| 7,160,298 B2 | 1/2007 | Lawes et al. |
| 7,163,548 B2 | 1/2007 | Stulen et al. |
| 7,169,104 B2 | 1/2007 | Ueda et al. |
| 7,169,146 B2 | 1/2007 | Truckai et al. |
| 7,169,156 B2 | 1/2007 | Hart |
| 7,170,823 B2 | 1/2007 | Fabricius et al. |
| 7,179,271 B2 | 2/2007 | Friedman et al. |
| 7,186,253 B2 | 3/2007 | Truckai et al. |
| 7,189,233 B2 | 3/2007 | Truckai et al. |
| 7,195,631 B2 | 3/2007 | Dumbauld |
| D541,418 S | 4/2007 | Schechter et al. |
| 7,199,545 B2 | 4/2007 | Oleynikov et al. |
| 7,204,820 B2 | 4/2007 | Akahoshi |
| 7,207,471 B2 | 4/2007 | Heinrich et al. |
| 7,208,005 B2 | 4/2007 | Frecker et al. |
| 7,211,094 B2 | 5/2007 | Gannoe et al. |
| 7,220,951 B2 | 5/2007 | Truckai et al. |
| 7,223,229 B2 | 5/2007 | Inman et al. |
| 7,225,964 B2 | 6/2007 | Mastri et al. |
| 7,226,448 B2 | 6/2007 | Bertolero et al. |
| 7,229,455 B2 | 6/2007 | Sakurai et al. |
| 7,232,440 B2 | 6/2007 | Dumbauld et al. |
| 7,235,064 B2 | 6/2007 | Hopper et al. |
| 7,235,073 B2 | 6/2007 | Levine et al. |
| 7,241,290 B2 | 7/2007 | Doyle et al. |
| 7,241,294 B2 | 7/2007 | Reschke |
| 7,241,296 B2 | 7/2007 | Buysse et al. |
| 7,246,734 B2 | 7/2007 | Shelton, IV |
| 7,251,531 B2 | 7/2007 | Mosher et al. |
| 7,252,667 B2 | 8/2007 | Moses et al. |
| 7,255,697 B2 | 8/2007 | Dycus et al. |
| 7,267,677 B2 | 9/2007 | Johnson et al. |
| 7,267,685 B2 | 9/2007 | Butaric et al. |
| 7,270,664 B2 | 9/2007 | Johnson et al. |
| 7,273,483 B2 | 9/2007 | Wiener et al. |
| 7,276,065 B2 | 10/2007 | Morley et al. |
| 7,282,773 B2 | 10/2007 | Li et al. |
| 7,287,682 B1 | 10/2007 | Ezzat et al. |
| 7,297,145 B2 | 11/2007 | Woloszko et al. |
| 7,297,149 B2 | 11/2007 | Vitali et al. |
| 7,300,450 B2 | 11/2007 | Vleugels et al. |
| 7,303,557 B2 | 12/2007 | Wham et al. |
| 7,307,313 B2 | 12/2007 | Ohyanagi et al. |
| 7,309,849 B2 | 12/2007 | Truckai et al. |
| 7,311,709 B2 | 12/2007 | Truckai et al. |
| 7,317,955 B2 | 1/2008 | McGreevy |
| 7,326,236 B2 | 2/2008 | Andreas et al. |
| 7,329,257 B2 | 2/2008 | Kanehira et al. |
| 7,331,410 B2 | 2/2008 | Yong et al. |
| 7,353,068 B2 | 4/2008 | Tanaka et al. |
| 7,354,440 B2 | 4/2008 | Truckai et al. |
| 7,357,287 B2 | 4/2008 | Shelton, IV et al. |
| 7,360,542 B2 | 4/2008 | Nelson et al. |
| 7,364,577 B2 | 4/2008 | Wham et al. |
| 7,367,973 B2 | 5/2008 | Manzo et al. |
| 7,367,976 B2 | 5/2008 | Lawes et al. |
| 7,371,227 B2 | 5/2008 | Zeiner |
| RE40,388 E | 6/2008 | Gines |
| 7,380,695 B2 | 6/2008 | Doll et al. |
| 7,381,209 B2 | 6/2008 | Truckai et al. |
| 7,384,420 B2 | 6/2008 | Dycus et al. |
| 7,390,317 B2 | 6/2008 | Taylor et al. |
| 7,396,356 B2 | 7/2008 | Mollenauer |
| 7,403,224 B2 | 7/2008 | Fuller et al. |
| 7,404,508 B2 | 7/2008 | Smith et al. |
| 7,407,077 B2 | 8/2008 | Ortiz et al. |
| 7,408,288 B2 | 8/2008 | Hara |
| 7,416,101 B2 | 8/2008 | Shelton, IV et al. |
| D576,725 S | 9/2008 | Shumer et al. |
| 7,422,139 B2 | 9/2008 | Shelton, IV et al. |
| 7,422,586 B2 | 9/2008 | Morris et al. |
| 7,422,592 B2 | 9/2008 | Morley et al. |
| 7,429,259 B2 | 9/2008 | Cadeddu et al. |
| D578,643 S | 10/2008 | Shumer et al. |
| D578,644 S | 10/2008 | Shumer et al. |
| D578,645 S | 10/2008 | Shumer et al. |
| 7,431,704 B2 | 10/2008 | Babaev |
| 7,435,249 B2 | 10/2008 | Buysse et al. |
| 7,435,582 B2 | 10/2008 | Zimmermann et al. |
| 7,439,732 B2 | 10/2008 | LaPlaca |
| 7,441,684 B2 | 10/2008 | Shelton, IV et al. |
| 7,442,193 B2 | 10/2008 | Shields et al. |
| 7,442,194 B2 | 10/2008 | Dumbauld et al. |
| 7,445,621 B2 | 11/2008 | Dumbauld et al. |
| 7,448,993 B2 | 11/2008 | Yokoi et al. |
| 7,449,004 B2 | 11/2008 | Yamada et al. |
| 7,450,998 B2 | 11/2008 | Zilberman et al. |
| 7,451,904 B2 | 11/2008 | Shelton, IV |
| 7,464,846 B2 | 12/2008 | Shelton, IV et al. |
| 7,472,815 B2 | 1/2009 | Shelton, IV et al. |
| 7,473,253 B2 | 1/2009 | Dycus et al. |
| 7,479,148 B2 | 1/2009 | Beaupre |
| 7,479,160 B2 | 1/2009 | Branch et al. |
| 7,487,899 B2 | 2/2009 | Shelton, IV et al. |

(56) References Cited

U.S. PATENT DOCUMENTS

| | | |
|---|---|---|
| 7,488,319 B2 | 2/2009 | Yates |
| 7,491,201 B2 | 2/2009 | Shields et al. |
| 7,494,468 B2 | 2/2009 | Rabiner et al. |
| 7,494,501 B2 | 2/2009 | Ahlberg et al. |
| 7,498,080 B2 | 3/2009 | Tung et al. |
| 7,503,893 B2 | 3/2009 | Kucklick |
| 7,505,812 B1 | 3/2009 | Eggers et al. |
| 7,506,791 B2 | 3/2009 | Omaits et al. |
| 7,510,107 B2 | 3/2009 | Timm et al. |
| 7,510,556 B2 | 3/2009 | Nguyen et al. |
| 7,511,733 B2 | 3/2009 | Takizawa et al. |
| 7,513,025 B2 | 4/2009 | Fischer |
| 7,517,349 B2 | 4/2009 | Truckai et al. |
| 7,520,877 B2 | 4/2009 | Lee, Jr. et al. |
| 7,524,320 B2 | 4/2009 | Tierney et al. |
| 7,534,243 B1 | 5/2009 | Chin et al. |
| D594,983 S | 6/2009 | Price et al. |
| 7,540,872 B2 | 6/2009 | Schechter et al. |
| 7,543,730 B1 | 6/2009 | Marczyk |
| 7,544,200 B2 | 6/2009 | Houser |
| 7,550,216 B2 | 6/2009 | Ofer et al. |
| 7,553,309 B2 | 6/2009 | Buysse et al. |
| 7,559,452 B2 | 7/2009 | Wales et al. |
| 7,566,318 B2 | 7/2009 | Haefner |
| 7,567,012 B2 | 7/2009 | Namikawa |
| 7,582,086 B2 | 9/2009 | Privitera et al. |
| 7,582,087 B2 | 9/2009 | Tetzlaff et al. |
| 7,586,289 B2 | 9/2009 | Andruk et al. |
| 7,588,176 B2 | 9/2009 | Timm et al. |
| 7,588,177 B2 | 9/2009 | Racenet |
| 7,594,925 B2 | 9/2009 | Danek et al. |
| 7,597,693 B2 | 10/2009 | Garrison |
| 7,599,743 B2 | 10/2009 | Hassler, Jr. et al. |
| 7,601,119 B2 | 10/2009 | Shahinian |
| 7,604,150 B2 | 10/2009 | Boudreaux |
| 7,611,512 B2 | 11/2009 | Ein-Gal |
| 7,617,961 B2 | 11/2009 | Viola |
| 7,621,910 B2 | 11/2009 | Sugi |
| 7,621,930 B2 | 11/2009 | Houser |
| 7,625,370 B2 | 12/2009 | Hart et al. |
| 7,628,791 B2 | 12/2009 | Garrison et al. |
| 7,628,792 B2 | 12/2009 | Guerra |
| 7,632,267 B2 | 12/2009 | Dahla |
| 7,632,269 B2 | 12/2009 | Truckai et al. |
| 7,637,410 B2 | 12/2009 | Marczyk |
| 7,640,447 B2 | 12/2009 | Qiu |
| 7,641,653 B2 | 1/2010 | Dalla Betta et al. |
| 7,641,671 B2 | 1/2010 | Crainich |
| 7,644,848 B2 | 1/2010 | Swayze et al. |
| 7,645,277 B2 | 1/2010 | McClurken et al. |
| 7,648,499 B2 | 1/2010 | Orszulak et al. |
| 7,658,311 B2 | 2/2010 | Boudreaux |
| 7,662,151 B2 | 2/2010 | Crompton, Jr. et al. |
| 7,665,647 B2 | 2/2010 | Shelton, IV et al. |
| 7,666,206 B2 | 2/2010 | Taniguchi et al. |
| 7,670,334 B2 | 3/2010 | Hueil et al. |
| 7,678,043 B2 | 3/2010 | Gilad |
| 7,678,105 B2 | 3/2010 | McGreevy et al. |
| 7,686,804 B2 | 3/2010 | Johnson et al. |
| 7,691,095 B2 | 4/2010 | Bednarek et al. |
| 7,691,098 B2 | 4/2010 | Wallace et al. |
| 7,691,103 B2 | 4/2010 | Fernandez et al. |
| 7,703,459 B2 | 4/2010 | Saadat et al. |
| 7,703,653 B2 | 4/2010 | Shah et al. |
| 7,708,735 B2 | 5/2010 | Chapman et al. |
| 7,708,751 B2 | 5/2010 | Hughes et al. |
| 7,708,758 B2 | 5/2010 | Lee et al. |
| 7,717,312 B2 | 5/2010 | Beetel |
| 7,717,914 B2 | 5/2010 | Kimura |
| 7,717,915 B2 | 5/2010 | Miyazawa |
| 7,722,527 B2 | 5/2010 | Bouchier et al. |
| 7,722,607 B2 | 5/2010 | Dumbauld et al. |
| 7,725,214 B2 | 5/2010 | Diolaiti |
| D618,797 S | 6/2010 | Price et al. |
| 7,726,537 B2 | 6/2010 | Olson et al. |
| 7,744,615 B2 | 6/2010 | Couture |
| 7,751,115 B2 | 7/2010 | Song |
| 7,753,904 B2 | 7/2010 | Shelton, IV et al. |
| 7,753,908 B2 | 7/2010 | Swanson |
| 7,753,909 B2 | 7/2010 | Chapman et al. |
| 7,762,445 B2 | 7/2010 | Heinrich et al. |
| D621,503 S | 8/2010 | Otten et al. |
| 7,766,210 B2 | 8/2010 | Shelton, IV et al. |
| 7,766,910 B2 | 8/2010 | Hixson et al. |
| 7,770,774 B2 | 8/2010 | Mastri et al. |
| 7,770,775 B2 | 8/2010 | Shelton, IV et al. |
| 7,775,972 B2 | 8/2010 | Brock et al. |
| 7,776,036 B2 | 8/2010 | Schechter et al. |
| 7,776,037 B2 | 8/2010 | Odom |
| 7,780,651 B2 | 8/2010 | Madhani et al. |
| 7,780,659 B2 | 8/2010 | Okada et al. |
| 7,780,663 B2 | 8/2010 | Yates et al. |
| 7,784,663 B2 | 8/2010 | Shelton, IV |
| 7,789,283 B2 | 9/2010 | Shah |
| 7,789,878 B2 | 9/2010 | Dumbauld et al. |
| 7,789,883 B2 | 9/2010 | Takashino et al. |
| 7,793,814 B2 | 9/2010 | Racenet et al. |
| 7,799,027 B2 | 9/2010 | Hafner |
| 7,803,156 B2 | 9/2010 | Eder et al. |
| 7,806,891 B2 | 10/2010 | Nowlin et al. |
| 7,810,692 B2 | 10/2010 | Hall et al. |
| 7,810,693 B2 | 10/2010 | Broehl et al. |
| 7,815,641 B2 | 10/2010 | Dodde et al. |
| 7,819,298 B2 | 10/2010 | Hall et al. |
| 7,819,299 B2 | 10/2010 | Shelton, IV et al. |
| 7,819,872 B2 | 10/2010 | Johnson et al. |
| D627,066 S | 11/2010 | Romero |
| 7,824,401 B2 | 11/2010 | Manzo et al. |
| 7,832,408 B2 | 11/2010 | Shelton, IV et al. |
| 7,832,612 B2 | 11/2010 | Baxter, III et al. |
| 7,837,699 B2 | 11/2010 | Yamada et al. |
| 7,845,537 B2 | 12/2010 | Shelton, IV et al. |
| 7,846,159 B2 | 12/2010 | Morrison et al. |
| 7,846,160 B2 | 12/2010 | Payne et al. |
| 7,850,688 B2 | 12/2010 | Hafner |
| D631,155 S | 1/2011 | Peine et al. |
| 7,861,906 B2 | 1/2011 | Doll et al. |
| 7,862,560 B2 | 1/2011 | Marion |
| 7,867,228 B2 | 1/2011 | Nobis et al. |
| 7,871,392 B2 | 1/2011 | Sartor |
| 7,871,423 B2 | 1/2011 | Livneh |
| D631,965 S | 2/2011 | Price et al. |
| 7,877,852 B2 | 2/2011 | Unger et al. |
| 7,877,853 B2 | 2/2011 | Unger et al. |
| 7,879,035 B2 | 2/2011 | Garrison et al. |
| 7,879,070 B2 | 2/2011 | Ortiz et al. |
| 7,887,535 B2 | 2/2011 | Lands et al. |
| 7,892,606 B2 | 2/2011 | Thies et al. |
| 7,896,875 B2 | 3/2011 | Heim et al. |
| 7,896,878 B2 | 3/2011 | Johnson et al. |
| 7,901,400 B2 | 3/2011 | Wham et al. |
| 7,901,423 B2 | 3/2011 | Stulen et al. |
| 7,905,881 B2 | 3/2011 | Masuda et al. |
| 7,909,220 B2 | 3/2011 | Viola |
| 7,919,184 B2 | 4/2011 | Mohapatra et al. |
| 7,922,061 B2 | 4/2011 | Shelton, IV et al. |
| 7,922,651 B2 | 4/2011 | Yamada et al. |
| 7,922,953 B2 | 4/2011 | Guerra |
| 7,931,649 B2 | 4/2011 | Couture et al. |
| D637,288 S | 5/2011 | Houghton |
| D638,540 S | 5/2011 | Ijiri et al. |
| 7,935,114 B2 | 5/2011 | Takashino et al. |
| 7,942,303 B2 | 5/2011 | Shah |
| 7,942,868 B2 | 5/2011 | Cooper |
| 7,951,165 B2 | 5/2011 | Golden et al. |
| 7,955,331 B2 | 6/2011 | Truckai et al. |
| 7,959,050 B2 | 6/2011 | Smith et al. |
| 7,959,626 B2 | 6/2011 | Hong et al. |
| 7,963,963 B2 | 6/2011 | Francischelli et al. |
| 7,967,602 B2 | 6/2011 | Lindquist |
| 7,976,544 B2 | 7/2011 | McClurken et al. |
| 7,980,443 B2 | 7/2011 | Scheib et al. |
| 7,981,113 B2 | 7/2011 | Truckai et al. |
| 7,988,567 B2 | 8/2011 | Kim et al. |

(56) References Cited

U.S. PATENT DOCUMENTS

| | | |
|---|---|---|
| 7,997,278 B2 | 8/2011 | Utley et al. |
| 8,020,743 B2 | 9/2011 | Shelton, IV |
| 8,033,173 B2 | 10/2011 | Ehlert et al. |
| 8,038,612 B2 | 10/2011 | Paz |
| 8,038,693 B2 | 10/2011 | Allen |
| 8,048,070 B2 | 11/2011 | O'Brien et al. |
| 8,052,672 B2 | 11/2011 | Laufer et al. |
| 8,056,720 B2 | 11/2011 | Hawkes |
| 8,056,787 B2 | 11/2011 | Boudreaux et al. |
| 8,057,498 B2 | 11/2011 | Robertson |
| 8,058,771 B2 | 11/2011 | Giordano et al. |
| 8,061,014 B2 | 11/2011 | Smith et al. |
| 8,062,211 B2 | 11/2011 | Duval et al. |
| 8,066,167 B2 | 11/2011 | Measamer et al. |
| 8,070,036 B1 | 12/2011 | Knodel |
| 8,070,748 B2 | 12/2011 | Hixson et al. |
| 8,075,555 B2 | 12/2011 | Truckai et al. |
| 8,075,558 B2 | 12/2011 | Truckai et al. |
| 8,092,475 B2 | 1/2012 | Cotter et al. |
| 8,100,894 B2 | 1/2012 | Mucko et al. |
| 8,105,323 B2 | 1/2012 | Buysse et al. |
| 8,105,324 B2 | 1/2012 | Palanker et al. |
| 8,114,104 B2 | 2/2012 | Young et al. |
| 8,114,119 B2 | 2/2012 | Spivey et al. |
| 8,128,624 B2 | 3/2012 | Couture et al. |
| 8,128,657 B2 | 3/2012 | Shiono et al. |
| 8,133,218 B2 | 3/2012 | Daw et al. |
| 8,136,712 B2 | 3/2012 | Zingman |
| 8,141,762 B2 | 3/2012 | Bedi et al. |
| 8,142,461 B2 | 3/2012 | Houser et al. |
| 8,147,488 B2 | 4/2012 | Masuda |
| 8,147,508 B2 | 4/2012 | Madan et al. |
| 8,152,825 B2 | 4/2012 | Madan et al. |
| 8,157,145 B2 | 4/2012 | Shelton, IV et al. |
| 8,161,977 B2 | 4/2012 | Shelton, IV et al. |
| 8,162,940 B2 | 4/2012 | Johnson et al. |
| 8,177,794 B2 | 5/2012 | Cabrera et al. |
| 8,182,502 B2 | 5/2012 | Stulen et al. |
| 8,186,560 B2 | 5/2012 | Hess et al. |
| 8,187,166 B2 | 5/2012 | Kuth et al. |
| 8,187,267 B2 | 5/2012 | Pappone et al. |
| 8,192,433 B2 | 6/2012 | Johnson et al. |
| 8,197,472 B2 | 6/2012 | Lau et al. |
| 8,197,479 B2 | 6/2012 | Olson et al. |
| 8,197,494 B2 | 6/2012 | Jaggi et al. |
| 8,197,502 B2 | 6/2012 | Smith et al. |
| 8,206,212 B2 | 6/2012 | Iddings et al. |
| 8,221,415 B2 | 7/2012 | Francischelli |
| 8,226,675 B2 | 7/2012 | Houser et al. |
| 8,236,019 B2 | 8/2012 | Houser |
| 8,236,020 B2 | 8/2012 | Smith et al. |
| 8,241,235 B2 | 8/2012 | Kahler et al. |
| 8,241,283 B2 | 8/2012 | Guerra et al. |
| 8,241,284 B2 | 8/2012 | Dycus et al. |
| 8,241,312 B2 | 8/2012 | Messerly |
| 8,244,368 B2 | 8/2012 | Sherman |
| 8,246,615 B2 | 8/2012 | Behnke |
| 8,246,618 B2 | 8/2012 | Bucciaglia et al. |
| 8,251,994 B2 | 8/2012 | McKenna et al. |
| 8,252,012 B2 | 8/2012 | Stulen |
| 8,257,352 B2 | 9/2012 | Lawes et al. |
| 8,257,377 B2 | 9/2012 | Wiener et al. |
| 8,262,563 B2 | 9/2012 | Bakos et al. |
| 8,267,300 B2 | 9/2012 | Boudreaux |
| 8,267,854 B2 | 9/2012 | Asada et al. |
| 8,267,935 B2 | 9/2012 | Couture et al. |
| 8,273,085 B2 | 9/2012 | Park et al. |
| 8,277,446 B2 | 10/2012 | Heard |
| 8,277,447 B2 | 10/2012 | Garrison et al. |
| 8,277,471 B2 | 10/2012 | Wiener et al. |
| 8,282,581 B2 | 10/2012 | Zhao et al. |
| 8,282,669 B2 | 10/2012 | Gerber et al. |
| 8,287,528 B2 | 10/2012 | Wham et al. |
| 8,292,886 B2 | 10/2012 | Kerr et al. |
| 8,292,888 B2 | 10/2012 | Whitman |
| 8,298,228 B2 | 10/2012 | Buysse et al. |
| 8,298,232 B2 | 10/2012 | Unger |
| 8,303,583 B2 | 11/2012 | Hosier et al. |
| 8,306,629 B2 | 11/2012 | Mioduski et al. |
| 8,308,040 B2 | 11/2012 | Huang et al. |
| 8,319,400 B2 | 11/2012 | Houser et al. |
| 8,322,455 B2 | 12/2012 | Shelton, IV et al. |
| 8,323,302 B2 | 12/2012 | Robertson et al. |
| 8,323,310 B2 | 12/2012 | Kingsley |
| 8,328,061 B2 | 12/2012 | Kasvikis |
| 8,328,761 B2 | 12/2012 | Widenhouse et al. |
| 8,328,834 B2 | 12/2012 | Isaacs et al. |
| 8,333,778 B2 | 12/2012 | Smith et al. |
| 8,333,779 B2 | 12/2012 | Smith et al. |
| 8,334,468 B2 | 12/2012 | Palmer et al. |
| 8,334,635 B2 | 12/2012 | Voegele et al. |
| 8,338,726 B2 | 12/2012 | Palmer et al. |
| 8,343,146 B2 | 1/2013 | Godara et al. |
| 8,344,596 B2 | 1/2013 | Nield et al. |
| 8,348,880 B2 | 1/2013 | Messerly et al. |
| 8,348,947 B2 | 1/2013 | Takashino et al. |
| 8,348,967 B2 | 1/2013 | Stulen |
| 8,353,297 B2 | 1/2013 | Dacquay et al. |
| 8,357,158 B2 | 1/2013 | McKenna et al. |
| 8,361,569 B2 | 1/2013 | Saito et al. |
| 8,372,064 B2 | 2/2013 | Douglass et al. |
| 8,372,099 B2 | 2/2013 | Deville et al. |
| 8,372,101 B2 | 2/2013 | Smith et al. |
| 8,377,053 B2 | 2/2013 | Orszulak |
| 8,377,059 B2 | 2/2013 | Deville et al. |
| 8,377,085 B2 | 2/2013 | Smith et al. |
| 8,382,754 B2 | 2/2013 | Odom et al. |
| 8,382,782 B2 | 2/2013 | Robertson et al. |
| 8,382,792 B2 | 2/2013 | Chojin |
| 8,388,646 B2 | 3/2013 | Chojin |
| 8,388,647 B2 | 3/2013 | Nau, Jr. et al. |
| 8,394,094 B2 | 3/2013 | Edwards et al. |
| 8,394,115 B2 | 3/2013 | Houser et al. |
| 8,397,971 B2 | 3/2013 | Yates et al. |
| 8,403,926 B2 | 3/2013 | Nobis et al. |
| 8,403,948 B2 | 3/2013 | Deville et al. |
| 8,403,949 B2 | 3/2013 | Palmer et al. |
| 8,403,950 B2 | 3/2013 | Palmer et al. |
| 8,409,076 B2 | 4/2013 | Pang et al. |
| 8,414,577 B2 | 4/2013 | Boudreaux et al. |
| 8,418,349 B2 | 4/2013 | Smith et al. |
| 8,419,757 B2 | 4/2013 | Smith et al. |
| 8,419,758 B2 | 4/2013 | Smith et al. |
| 8,419,759 B2 | 4/2013 | Dietz |
| 8,425,410 B2 | 4/2013 | Murray et al. |
| 8,425,545 B2 | 4/2013 | Smith et al. |
| 8,430,811 B2 | 4/2013 | Hess et al. |
| 8,430,876 B2 | 4/2013 | Kappus et al. |
| 8,430,897 B2 | 4/2013 | Novak et al. |
| 8,430,898 B2 | 4/2013 | Wiener et al. |
| 8,435,257 B2 | 5/2013 | Smith et al. |
| 8,439,939 B2 | 5/2013 | Deville et al. |
| 8,444,662 B2 | 5/2013 | Palmer et al. |
| 8,444,664 B2 | 5/2013 | Balanev et al. |
| 8,453,906 B2 | 6/2013 | Huang et al. |
| 8,454,599 B2 | 6/2013 | Inagaki et al. |
| 8,454,639 B2 | 6/2013 | Du et al. |
| 8,460,288 B2 | 6/2013 | Tamai et al. |
| 8,460,292 B2 | 6/2013 | Truckai et al. |
| 8,461,744 B2 | 6/2013 | Wiener et al. |
| 8,469,956 B2 | 6/2013 | McKenna et al. |
| 8,469,981 B2 | 6/2013 | Robertson et al. |
| 8,475,361 B2 | 7/2013 | Barlow et al. |
| 8,475,453 B2 | 7/2013 | Marczyk et al. |
| 8,480,703 B2 | 7/2013 | Nicholas et al. |
| 8,484,833 B2 | 7/2013 | Cunningham et al. |
| 8,485,413 B2 | 7/2013 | Scheib et al. |
| 8,485,970 B2 | 7/2013 | Widenhouse et al. |
| 8,486,057 B2 | 7/2013 | Behnke, II |
| 8,486,096 B2 | 7/2013 | Robertson et al. |
| 8,491,625 B2 | 7/2013 | Horner |
| 8,496,682 B2 | 7/2013 | Guerra et al. |
| 8,512,336 B2 | 8/2013 | Couture |
| 8,512,364 B2 | 8/2013 | Kowalski et al. |

(56) References Cited

U.S. PATENT DOCUMENTS

| | | |
|---|---|---|
| 8,512,365 B2 | 8/2013 | Wiener et al. |
| 8,523,889 B2 | 9/2013 | Stulen et al. |
| 8,529,437 B2 | 9/2013 | Taylor et al. |
| 8,529,565 B2 | 9/2013 | Masuda et al. |
| 8,531,064 B2 | 9/2013 | Robertson et al. |
| 8,535,311 B2 | 9/2013 | Schall |
| 8,535,340 B2 | 9/2013 | Allen |
| 8,535,341 B2 | 9/2013 | Allen |
| 8,540,128 B2 | 9/2013 | Shelton, IV et al. |
| 8,542,501 B2 | 9/2013 | Kyono |
| 8,553,430 B2 | 10/2013 | Melanson et al. |
| 8,562,516 B2 | 10/2013 | Saadat et al. |
| 8,562,592 B2 | 10/2013 | Conlon et al. |
| 8,562,598 B2 | 10/2013 | Falkenstein et al. |
| 8,562,604 B2 | 10/2013 | Nishimura |
| 8,568,390 B2 | 10/2013 | Mueller |
| 8,568,412 B2 | 10/2013 | Brandt et al. |
| 8,569,997 B2 | 10/2013 | Lee |
| 8,574,187 B2 | 11/2013 | Marion |
| 8,574,231 B2 | 11/2013 | Boudreaux et al. |
| 8,579,176 B2 | 11/2013 | Smith et al. |
| 8,579,928 B2 | 11/2013 | Robertson et al. |
| 8,579,937 B2 | 11/2013 | Gresham |
| 8,591,459 B2 | 11/2013 | Clymer et al. |
| 8,591,506 B2 | 11/2013 | Wham et al. |
| D695,407 S | 12/2013 | Price et al. |
| 8,596,513 B2 | 12/2013 | Olson et al. |
| 8,597,182 B2 | 12/2013 | Stein et al. |
| 8,597,297 B2 | 12/2013 | Couture et al. |
| 8,608,044 B2 | 12/2013 | Hueil et al. |
| 8,613,383 B2 | 12/2013 | Beckman et al. |
| 8,622,274 B2 | 1/2014 | Yates et al. |
| 8,623,011 B2 | 1/2014 | Spivey |
| 8,623,016 B2 | 1/2014 | Fischer |
| 8,623,027 B2 | 1/2014 | Price et al. |
| 8,623,044 B2 | 1/2014 | Timm et al. |
| 8,628,529 B2 | 1/2014 | Aldridge et al. |
| 8,632,461 B2 | 1/2014 | Glossop |
| 8,632,539 B2 | 1/2014 | Twomey et al. |
| 8,636,648 B2 | 1/2014 | Gazdzinski |
| 8,636,736 B2 | 1/2014 | Yates et al. |
| 8,636,761 B2 | 1/2014 | Cunningham et al. |
| 8,638,428 B2 | 1/2014 | Brown |
| 8,640,788 B2 | 2/2014 | Dachs, II et al. |
| 8,641,712 B2 | 2/2014 | Couture |
| 8,647,350 B2 | 2/2014 | Mohan et al. |
| 8,650,728 B2 | 2/2014 | Wan et al. |
| 8,652,120 B2 | 2/2014 | Giordano et al. |
| 8,652,155 B2 | 2/2014 | Houser et al. |
| 8,663,220 B2 | 3/2014 | Wiener et al. |
| 8,663,222 B2 | 3/2014 | Anderson et al. |
| 8,663,223 B2 | 3/2014 | Masuda et al. |
| 8,668,691 B2 | 3/2014 | Heard |
| RE44,834 E | 4/2014 | Dumbauld et al. |
| 8,684,253 B2 | 4/2014 | Giordano et al. |
| 8,685,020 B2 | 4/2014 | Weizman et al. |
| 8,685,056 B2 | 4/2014 | Evans et al. |
| 8,696,662 B2 | 4/2014 | Eder et al. |
| 8,696,665 B2 | 4/2014 | Hunt et al. |
| 8,702,609 B2 | 4/2014 | Hadjicostis |
| 8,702,704 B2 | 4/2014 | Shelton, IV et al. |
| 8,708,213 B2 | 4/2014 | Shelton, IV et al. |
| 8,709,035 B2 | 4/2014 | Johnson et al. |
| 8,715,270 B2 | 5/2014 | Weitzner et al. |
| 8,715,277 B2 | 5/2014 | Weizman |
| 8,721,640 B2 | 5/2014 | Taylor et al. |
| 8,734,443 B2 | 5/2014 | Hixson et al. |
| 8,747,238 B2 | 6/2014 | Shelton, IV et al. |
| 8,747,351 B2 | 6/2014 | Schultz |
| 8,747,404 B2 | 6/2014 | Boudreaux et al. |
| 8,752,264 B2 | 6/2014 | Ackley et al. |
| 8,752,749 B2 | 6/2014 | Moore et al. |
| 8,753,338 B2 | 6/2014 | Widenhouse et al. |
| 8,758,342 B2 | 6/2014 | Bales et al. |
| 8,764,747 B2 | 7/2014 | Cummings et al. |
| 8,770,459 B2 | 7/2014 | Racenet et al. |
| 8,784,418 B2 | 7/2014 | Romero |
| 8,789,740 B2 | 7/2014 | Baxter, III et al. |
| 8,790,342 B2 | 7/2014 | Stulen et al. |
| 8,795,274 B2 | 8/2014 | Hanna |
| 8,795,276 B2 | 8/2014 | Dietz et al. |
| 8,795,327 B2 | 8/2014 | Dietz et al. |
| 8,800,838 B2 | 8/2014 | Shelton, IV |
| 8,801,752 B2 | 8/2014 | Fortier et al. |
| 8,807,414 B2 | 8/2014 | Ross et al. |
| 8,808,319 B2 | 8/2014 | Houser et al. |
| 8,814,856 B2 | 8/2014 | Elmouelhi et al. |
| 8,814,865 B2 | 8/2014 | Reschke |
| 8,814,870 B2 | 8/2014 | Paraschiv et al. |
| 8,827,992 B2 | 9/2014 | Koss et al. |
| 8,827,995 B2 | 9/2014 | Schaller et al. |
| 8,834,466 B2 | 9/2014 | Cummings et al. |
| 8,834,488 B2 | 9/2014 | Farritor et al. |
| 8,834,518 B2 | 9/2014 | Faller et al. |
| 8,845,630 B2 | 9/2014 | Mehta et al. |
| 8,851,354 B2 | 10/2014 | Swensgard et al. |
| 8,852,184 B2 | 10/2014 | Kucklick |
| 8,864,757 B2 | 10/2014 | Klimovitch et al. |
| 8,864,761 B2 | 10/2014 | Johnson et al. |
| 8,870,867 B2 | 10/2014 | Walberg et al. |
| 8,876,858 B2 | 11/2014 | Braun |
| 8,882,766 B2 | 11/2014 | Couture et al. |
| 8,882,791 B2 | 11/2014 | Stulen |
| 8,887,373 B2 | 11/2014 | Brandt et al. |
| 8,888,776 B2 | 11/2014 | Dietz et al. |
| 8,888,783 B2 | 11/2014 | Young |
| 8,888,809 B2 | 11/2014 | Davison et al. |
| 8,906,016 B2 | 12/2014 | Boudreaux et al. |
| 8,906,017 B2 | 12/2014 | Rioux et al. |
| 8,911,438 B2 | 12/2014 | Swoyer et al. |
| 8,911,460 B2 | 12/2014 | Neurohr et al. |
| 8,926,607 B2 | 1/2015 | Norvell et al. |
| 8,926,608 B2 | 1/2015 | Bacher et al. |
| 8,929,888 B2 | 1/2015 | Rao et al. |
| 8,931,682 B2 | 1/2015 | Timm et al. |
| 8,939,287 B2 | 1/2015 | Markovitch |
| 8,939,974 B2 | 1/2015 | Boudreaux et al. |
| 8,939,975 B2 | 1/2015 | Twomey et al. |
| 8,944,997 B2 | 2/2015 | Fernandez et al. |
| 8,945,125 B2 | 2/2015 | Schechter et al. |
| 8,951,248 B2 | 2/2015 | Messerly et al. |
| 8,951,272 B2 | 2/2015 | Robertson et al. |
| 8,956,349 B2 | 2/2015 | Aldridge et al. |
| 8,960,520 B2 | 2/2015 | McCuen |
| 8,961,515 B2 | 2/2015 | Twomey et al. |
| 8,961,547 B2 | 2/2015 | Dietz et al. |
| 8,968,276 B2 | 3/2015 | Zemlok et al. |
| 8,968,308 B2 | 3/2015 | Horner et al. |
| 8,968,312 B2 | 3/2015 | Marczyk et al. |
| 8,968,332 B2 | 3/2015 | Farritor et al. |
| 8,978,845 B2 | 3/2015 | Kim |
| 8,979,838 B2 | 3/2015 | Woloszko et al. |
| 8,979,843 B2 | 3/2015 | Timm et al. |
| 8,979,844 B2 | 3/2015 | White et al. |
| 8,979,890 B2 | 3/2015 | Boudreaux |
| 8,986,302 B2 | 3/2015 | Aldridge et al. |
| 8,989,855 B2 | 3/2015 | Murphy et al. |
| 8,992,422 B2 | 3/2015 | Spivey et al. |
| 8,992,526 B2 | 3/2015 | Brodbeck et al. |
| 9,005,199 B2 | 4/2015 | Beckman et al. |
| 9,011,437 B2 | 4/2015 | Woodruff et al. |
| 9,017,326 B2 | 4/2015 | DiNardo et al. |
| 9,017,372 B2 | 4/2015 | Artale et al. |
| 9,028,494 B2 | 5/2015 | Shelton, IV et al. |
| 9,028,519 B2 | 5/2015 | Yates et al. |
| 9,031,667 B2 | 5/2015 | Williams |
| 9,033,983 B2 | 5/2015 | Takashino et al. |
| 9,039,695 B2 | 5/2015 | Giordano et al. |
| 9,039,705 B2 | 5/2015 | Takashino |
| 9,039,731 B2 | 5/2015 | Joseph |
| 9,044,243 B2 | 6/2015 | Johnson et al. |
| 9,044,245 B2 | 6/2015 | Condie et al. |
| 9,044,256 B2 | 6/2015 | Cadeddu et al. |
| 9,044,261 B2 | 6/2015 | Houser |

(56) References Cited

U.S. PATENT DOCUMENTS

| | | |
|---|---|---|
| 9,050,093 B2 | 6/2015 | Aldridge et al. |
| 9,050,098 B2 | 6/2015 | Deville et al. |
| 9,055,961 B2 | 6/2015 | Manzo et al. |
| 9,060,770 B2 | 6/2015 | Shelton, IV et al. |
| 9,060,775 B2 | 6/2015 | Wiener et al. |
| 9,060,776 B2 | 6/2015 | Yates et al. |
| 9,066,723 B2 | 6/2015 | Beller et al. |
| 9,072,535 B2 | 7/2015 | Shelton, IV et al. |
| 9,072,536 B2 | 7/2015 | Shelton, IV et al. |
| 9,078,664 B2 | 7/2015 | Palmer et al. |
| 9,089,327 B2 | 7/2015 | Worrell et al. |
| 9,089,360 B2 | 7/2015 | Messerly et al. |
| 9,094,006 B2 | 7/2015 | Gravati et al. |
| 9,095,362 B2 | 8/2015 | Dachs, II et al. |
| 9,095,367 B2 * | 8/2015 | Olson .................... A61B 34/37 |
| 9,101,385 B2 | 8/2015 | Shelton, IV et al. |
| 9,107,672 B2 | 8/2015 | Tetzlaff et al. |
| 9,113,889 B2 | 8/2015 | Reschke |
| 9,113,900 B2 | 8/2015 | Buysse et al. |
| 9,119,630 B2 | 9/2015 | Townsend et al. |
| 9,119,657 B2 | 9/2015 | Shelton, IV et al. |
| 9,119,957 B2 | 9/2015 | Gantz et al. |
| 9,125,662 B2 | 9/2015 | Shelton, IV |
| 9,125,667 B2 | 9/2015 | Stone et al. |
| 9,138,289 B2 | 9/2015 | Conley et al. |
| 9,149,324 B2 | 10/2015 | Huang et al. |
| 9,149,325 B2 | 10/2015 | Worrell et al. |
| 9,155,585 B2 | 10/2015 | Bales, Jr. et al. |
| 9,161,803 B2 | 10/2015 | Yates et al. |
| 9,168,054 B2 | 10/2015 | Turner et al. |
| 9,168,085 B2 | 10/2015 | Juzkiw et al. |
| 9,168,089 B2 | 10/2015 | Buysse et al. |
| 9,179,912 B2 | 11/2015 | Yates et al. |
| 9,186,204 B2 | 11/2015 | Nishimura et al. |
| 9,187,758 B2 | 11/2015 | Cai et al. |
| 9,192,380 B2 | 11/2015 | Racenet et al. |
| 9,192,421 B2 | 11/2015 | Garrison |
| 9,192,431 B2 | 11/2015 | Woodruff et al. |
| 9,198,714 B2 | 12/2015 | Worrell et al. |
| 9,198,715 B2 | 12/2015 | Livneh |
| 9,198,716 B2 | 12/2015 | Masuda et al. |
| 9,204,879 B2 | 12/2015 | Shelton, IV |
| 9,204,919 B2 | 12/2015 | Brandt et al. |
| 9,216,050 B2 | 12/2015 | Condie et al. |
| 9,220,559 B2 | 12/2015 | Worrell et al. |
| 9,226,751 B2 | 1/2016 | Shelton, IV et al. |
| 9,226,767 B2 | 1/2016 | Stulen et al. |
| 9,237,891 B2 | 1/2016 | Shelton, IV |
| 9,254,165 B2 | 2/2016 | Aronow et al. |
| 9,259,234 B2 | 2/2016 | Robertson et al. |
| 9,259,265 B2 | 2/2016 | Harris et al. |
| 9,265,567 B2 | 2/2016 | Orban, III et al. |
| 9,265,571 B2 | 2/2016 | Twomey et al. |
| 9,265,926 B2 | 2/2016 | Strobl et al. |
| 9,271,784 B2 | 3/2016 | Evans et al. |
| 9,274,988 B2 | 3/2016 | Hsu et al. |
| 9,277,962 B2 | 3/2016 | Koss et al. |
| 9,282,974 B2 | 3/2016 | Shelton, IV |
| 9,283,027 B2 | 3/2016 | Monson et al. |
| 9,283,045 B2 | 3/2016 | Rhee et al. |
| 9,289,256 B2 | 3/2016 | Shelton, IV et al. |
| 9,295,514 B2 | 3/2016 | Shelton, IV et al. |
| 9,308,014 B2 | 4/2016 | Fischer |
| 9,314,292 B2 | 4/2016 | Trees et al. |
| 9,326,788 B2 | 5/2016 | Batross et al. |
| 9,326,812 B2 | 5/2016 | Waaler et al. |
| 9,333,025 B2 | 5/2016 | Monson et al. |
| 9,339,323 B2 | 5/2016 | Eder et al. |
| 9,339,326 B2 | 5/2016 | McCullagh et al. |
| 9,344,042 B2 | 5/2016 | Mao |
| 9,345,481 B2 | 5/2016 | Hall et al. |
| 9,345,900 B2 | 5/2016 | Wu et al. |
| 9,351,754 B2 | 5/2016 | Vakharia et al. |
| 9,358,065 B2 | 6/2016 | Ladtkow et al. |
| 9,364,230 B2 | 6/2016 | Shelton, IV et al. |
| 9,375,232 B2 | 6/2016 | Hunt et al. |
| 9,375,256 B2 | 6/2016 | Cunningham et al. |
| 9,375,267 B2 | 6/2016 | Kerr et al. |
| 9,381,060 B2 | 7/2016 | Artale et al. |
| 9,386,983 B2 | 7/2016 | Swensgard et al. |
| 9,393,037 B2 | 7/2016 | Olson et al. |
| 9,402,682 B2 | 8/2016 | Worrell et al. |
| 9,408,606 B2 | 8/2016 | Shelton, IV |
| 9,408,622 B2 | 8/2016 | Stulen et al. |
| 9,408,660 B2 | 8/2016 | Strobl et al. |
| 9,414,880 B2 | 8/2016 | Monson et al. |
| 9,421,060 B2 * | 8/2016 | Monson .................... H02J 7/00 |
| 9,456,863 B2 | 10/2016 | Moua |
| 9,456,864 B2 | 10/2016 | Witt et al. |
| 9,456,876 B2 | 10/2016 | Hagn |
| 9,492,224 B2 | 11/2016 | Boudreaux et al. |
| 9,504,524 B2 | 11/2016 | Behnke, II |
| 9,510,906 B2 | 12/2016 | Boudreaux et al. |
| 9,522,029 B2 | 12/2016 | Yates et al. |
| 9,526,564 B2 | 12/2016 | Rusin |
| 9,526,565 B2 | 12/2016 | Strobl |
| 9,549,663 B2 | 1/2017 | Larkin |
| 9,554,845 B2 | 1/2017 | Arts |
| 9,554,846 B2 | 1/2017 | Boudreaux |
| 9,554,854 B2 | 1/2017 | Yates et al. |
| 9,561,038 B2 | 2/2017 | Shelton, IV et al. |
| 9,585,709 B2 * | 3/2017 | Krapohl ............. A61B 18/1206 |
| 9,597,143 B2 | 3/2017 | Madan et al. |
| 9,610,091 B2 | 4/2017 | Johnson et al. |
| 9,610,114 B2 | 4/2017 | Baxter, III et al. |
| 9,615,877 B2 | 4/2017 | Tyrrell et al. |
| 9,622,810 B2 | 4/2017 | Hart et al. |
| 9,627,120 B2 | 4/2017 | Scott et al. |
| 9,629,629 B2 | 4/2017 | Leimbach et al. |
| 9,642,669 B2 | 5/2017 | Takashino et al. |
| 9,649,111 B2 | 5/2017 | Shelton, IV et al. |
| 9,649,144 B2 | 5/2017 | Aluru et al. |
| 9,649,151 B2 | 5/2017 | Goodman et al. |
| 9,662,131 B2 | 5/2017 | Omori et al. |
| 9,668,806 B2 | 6/2017 | Unger et al. |
| 9,687,295 B2 | 6/2017 | Joseph |
| 9,700,339 B2 | 7/2017 | Nield |
| 9,707,005 B2 | 7/2017 | Strobl et al. |
| 9,707,027 B2 | 7/2017 | Ruddenklau et al. |
| 9,707,030 B2 | 7/2017 | Davison et al. |
| 9,713,491 B2 | 7/2017 | Roy et al. |
| 9,724,118 B2 | 8/2017 | Schulte et al. |
| 9,724,152 B2 | 8/2017 | Horlle et al. |
| 9,737,355 B2 | 8/2017 | Yates et al. |
| 9,737,358 B2 | 8/2017 | Beckman et al. |
| 9,743,929 B2 | 8/2017 | Leimbach et al. |
| 9,757,128 B2 | 9/2017 | Baber et al. |
| 9,757,142 B2 | 9/2017 | Shimizu |
| 9,757,186 B2 | 9/2017 | Boudreaux et al. |
| 9,782,214 B2 | 10/2017 | Houser et al. |
| 9,782,220 B2 | 10/2017 | Mark et al. |
| 9,795,436 B2 | 10/2017 | Yates et al. |
| 9,802,033 B2 | 10/2017 | Hibner et al. |
| 9,808,244 B2 | 11/2017 | Leimbach et al. |
| 9,808,308 B2 | 11/2017 | Faller et al. |
| 9,814,460 B2 | 11/2017 | Kimsey et al. |
| 9,814,514 B2 | 11/2017 | Shelton, IV et al. |
| 9,820,768 B2 | 11/2017 | Gee et al. |
| 9,820,771 B2 | 11/2017 | Norton et al. |
| 9,833,239 B2 | 12/2017 | Yates et al. |
| 9,848,937 B2 | 12/2017 | Trees et al. |
| 9,848,939 B2 | 12/2017 | Mayer et al. |
| 9,861,428 B2 | 1/2018 | Trees et al. |
| 9,872,725 B2 | 1/2018 | Worrell et al. |
| 9,877,720 B2 | 1/2018 | Worrell et al. |
| 9,877,776 B2 | 1/2018 | Boudreaux |
| 9,877,782 B2 | 1/2018 | Voegele et al. |
| 9,888,958 B2 | 2/2018 | Evans et al. |
| 9,901,390 B2 | 2/2018 | Allen, IV et al. |
| 9,901,754 B2 | 2/2018 | Yamada |
| 9,907,563 B2 | 3/2018 | Germain et al. |
| 9,913,680 B2 | 3/2018 | Voegele et al. |
| 9,918,730 B2 | 3/2018 | Trees et al. |
| 9,931,157 B2 | 4/2018 | Strobl et al. |

(56) References Cited

U.S. PATENT DOCUMENTS

| | | |
|---|---|---|
| 9,937,001 B2 | 4/2018 | Nakamura |
| 9,943,357 B2 | 4/2018 | Cunningham et al. |
| 9,949,620 B2 | 4/2018 | Duval et al. |
| 9,949,785 B2 | 4/2018 | Price et al. |
| 9,949,788 B2 | 4/2018 | Boudreaux |
| 9,974,539 B2 | 5/2018 | Yates et al. |
| 9,993,289 B2 | 6/2018 | Sobajima et al. |
| 10,010,339 B2 | 7/2018 | Witt et al. |
| 10,016,207 B2 | 7/2018 | Suzuki et al. |
| 10,022,142 B2 | 7/2018 | Aranyi et al. |
| 10,041,822 B2 | 8/2018 | Zemlok |
| 10,052,044 B2 | 8/2018 | Shelton, IV et al. |
| 10,058,376 B2 | 8/2018 | Horner et al. |
| 10,070,916 B2 | 9/2018 | Artale |
| 10,080,606 B2 | 9/2018 | Kappus et al. |
| 10,092,310 B2 | 10/2018 | Boudreaux et al. |
| 10,092,348 B2 | 10/2018 | Boudreaux |
| 10,092,350 B2 | 10/2018 | Rothweiler et al. |
| 10,105,174 B2 * | 10/2018 | Krapohl ............ A61B 18/1233 |
| 10,111,699 B2 | 10/2018 | Boudreaux |
| 10,117,702 B2 | 11/2018 | Danziger et al. |
| 10,130,410 B2 | 11/2018 | Strobl et al. |
| 10,130,414 B2 | 11/2018 | Weiler et al. |
| 10,159,524 B2 | 12/2018 | Yates et al. |
| 10,166,060 B2 | 1/2019 | Johnson et al. |
| 10,172,669 B2 | 1/2019 | Felder et al. |
| 10,194,911 B2 | 2/2019 | Miller et al. |
| 10,194,972 B2 | 2/2019 | Yates et al. |
| 10,194,976 B2 | 2/2019 | Boudreaux |
| 10,194,977 B2 | 2/2019 | Yang |
| 10,211,586 B2 | 2/2019 | Adams et al. |
| 10,231,776 B2 | 3/2019 | Artale et al. |
| 10,238,387 B2 | 3/2019 | Yates et al. |
| 10,245,095 B2 | 4/2019 | Boudreaux |
| 10,258,404 B2 | 4/2019 | Wang |
| 10,265,118 B2 | 4/2019 | Gerhardt |
| 10,278,721 B2 | 5/2019 | Dietz et al. |
| 10,314,638 B2 | 6/2019 | Gee et al. |
| 10,321,950 B2 | 6/2019 | Yates et al. |
| 10,342,602 B2 | 7/2019 | Strobl et al. |
| 10,413,352 B2 | 9/2019 | Thomas et al. |
| 10,420,607 B2 | 9/2019 | Woloszko et al. |
| 10,433,900 B2 | 10/2019 | Harris et al. |
| 10,441,345 B2 | 10/2019 | Aldridge et al. |
| 10,463,421 B2 | 11/2019 | Boudreaux et al. |
| 10,478,243 B2 | 11/2019 | Couture et al. |
| 10,485,607 B2 | 11/2019 | Strobl et al. |
| 10,524,852 B1 | 1/2020 | Cagle et al. |
| 10,524,854 B2 | 1/2020 | Woodruff et al. |
| 10,568,682 B2 | 2/2020 | Dycus et al. |
| 10,575,868 B2 | 3/2020 | Hall et al. |
| 2001/0025184 A1 | 9/2001 | Messerly |
| 2001/0031950 A1 | 10/2001 | Ryan |
| 2001/0039419 A1 | 11/2001 | Francischelli et al. |
| 2002/0002377 A1 | 1/2002 | Cimino |
| 2002/0019649 A1 | 2/2002 | Sikora et al. |
| 2002/0022836 A1 | 2/2002 | Goble et al. |
| 2002/0049551 A1 | 4/2002 | Friedman et al. |
| 2002/0077550 A1 | 6/2002 | Rabiner et al. |
| 2002/0095175 A1 | 7/2002 | Brock et al. |
| 2002/0107517 A1 | 8/2002 | Witt et al. |
| 2002/0156493 A1 | 10/2002 | Houser et al. |
| 2003/0014053 A1 | 1/2003 | Nguyen et al. |
| 2003/0055443 A1 | 3/2003 | Spotnitz |
| 2003/0066938 A1 | 4/2003 | Zimmerman |
| 2003/0109875 A1 | 6/2003 | Tetzlaff et al. |
| 2003/0114731 A1 | 6/2003 | Cadeddu et al. |
| 2003/0114851 A1 | 6/2003 | Truckai et al. |
| 2003/0130693 A1 | 7/2003 | Levin et al. |
| 2003/0139741 A1 | 7/2003 | Goble et al. |
| 2003/0158548 A1 | 8/2003 | Phan et al. |
| 2003/0171747 A1 | 9/2003 | Kanehira et al. |
| 2003/0204199 A1 | 10/2003 | Novak et al. |
| 2003/0212332 A1 | 11/2003 | Fenton et al. |
| 2003/0229344 A1 | 12/2003 | Dycus et al. |
| 2004/0030254 A1 | 2/2004 | Babaev |
| 2004/0047485 A1 | 3/2004 | Sherrit et al. |
| 2004/0054364 A1 | 3/2004 | Aranyi et al. |
| 2004/0092921 A1 | 5/2004 | Kadziauskas et al. |
| 2004/0092992 A1 | 5/2004 | Adams et al. |
| 2004/0093039 A1 | 5/2004 | Schumert |
| 2004/0097919 A1 | 5/2004 | Wellman et al. |
| 2004/0097996 A1 | 5/2004 | Rabiner et al. |
| 2004/0102804 A1 | 5/2004 | Chin |
| 2004/0133089 A1 | 7/2004 | Kilcoyne et al. |
| 2004/0138621 A1 | 7/2004 | Jahns et al. |
| 2004/0167508 A1 | 8/2004 | Wham et al. |
| 2004/0193150 A1 | 9/2004 | Sharkey et al. |
| 2004/0199193 A1 | 10/2004 | Hayashi et al. |
| 2004/0249367 A1 | 12/2004 | Saadat et al. |
| 2004/0249374 A1 | 12/2004 | Tetzlaff et al. |
| 2004/0260273 A1 | 12/2004 | Wan |
| 2004/0260300 A1 | 12/2004 | Gorensek et al. |
| 2005/0015125 A1 | 1/2005 | Mioduski et al. |
| 2005/0033278 A1 | 2/2005 | McClurken et al. |
| 2005/0033337 A1 | 2/2005 | Muir et al. |
| 2005/0090817 A1 | 4/2005 | Phan |
| 2005/0096502 A1 | 5/2005 | Khalili |
| 2005/0119640 A1 | 6/2005 | Sverduk et al. |
| 2005/0131390 A1 | 6/2005 | Heinrich et al. |
| 2005/0143769 A1 | 6/2005 | White et al. |
| 2005/0149108 A1 | 7/2005 | Cox |
| 2005/0165429 A1 | 7/2005 | Douglas et al. |
| 2005/0171522 A1 | 8/2005 | Christopherson |
| 2005/0177184 A1 | 8/2005 | Easley |
| 2005/0192610 A1 | 9/2005 | Houser et al. |
| 2005/0215858 A1 | 9/2005 | Vail |
| 2005/0256405 A1 | 11/2005 | Makin et al. |
| 2005/0261588 A1 | 11/2005 | Makin et al. |
| 2005/0267464 A1 | 12/2005 | Truckai et al. |
| 2005/0272972 A1 | 12/2005 | Iddan |
| 2005/0273139 A1 | 12/2005 | Krauss et al. |
| 2005/0288555 A1 | 12/2005 | Binmoeller |
| 2005/0288659 A1 | 12/2005 | Kimura et al. |
| 2006/0030797 A1 | 2/2006 | Zhou et al. |
| 2006/0058825 A1 | 3/2006 | Ogura et al. |
| 2006/0063130 A1 | 3/2006 | Hayman et al. |
| 2006/0064086 A1 | 3/2006 | Odom |
| 2006/0159731 A1 | 7/2006 | Shoshan |
| 2006/0190034 A1 | 8/2006 | Nishizawa et al. |
| 2006/0211943 A1 | 9/2006 | Beaupre |
| 2006/0253050 A1 | 11/2006 | Yoshimine et al. |
| 2006/0270916 A1 | 11/2006 | Skwarek et al. |
| 2006/0293656 A1 | 12/2006 | Shadduck et al. |
| 2007/0008744 A1 | 1/2007 | Heo et al. |
| 2007/0010709 A1 | 1/2007 | Reinschke |
| 2007/0016235 A1 | 1/2007 | Tanaka et al. |
| 2007/0016236 A1 | 1/2007 | Beaupre |
| 2007/0020065 A1 | 1/2007 | Kirby |
| 2007/0032701 A1 | 2/2007 | Fowler et al. |
| 2007/0032704 A1 | 2/2007 | Gandini et al. |
| 2007/0051766 A1 | 3/2007 | Spencer |
| 2007/0055228 A1 | 3/2007 | Berg et al. |
| 2007/0063618 A1 | 3/2007 | Bromfield |
| 2007/0073185 A1 | 3/2007 | Nakao |
| 2007/0073341 A1 | 3/2007 | Smith et al. |
| 2007/0106317 A1 | 5/2007 | Shelton et al. |
| 2007/0118115 A1 | 5/2007 | Artale et al. |
| 2007/0123748 A1 | 5/2007 | Meglan |
| 2007/0130771 A1 | 6/2007 | Ehlert et al. |
| 2007/0135686 A1 | 6/2007 | Pruitt et al. |
| 2007/0149881 A1 | 6/2007 | Rabin |
| 2007/0173803 A1 | 7/2007 | Wham et al. |
| 2007/0173813 A1 | 7/2007 | Odom |
| 2007/0173872 A1 | 7/2007 | Neuenfeldt |
| 2007/0182842 A1 | 8/2007 | Sonnenschein et al. |
| 2007/0185474 A1 | 8/2007 | Nahen |
| 2007/0191713 A1 | 8/2007 | Eichmann et al. |
| 2007/0203483 A1 | 8/2007 | Kim et al. |
| 2007/0208340 A1 | 9/2007 | Ganz et al. |
| 2007/0219481 A1 | 9/2007 | Babaev |
| 2007/0232926 A1 | 10/2007 | Stulen et al. |
| 2007/0232928 A1 | 10/2007 | Wiener et al. |
| 2007/0236213 A1 | 10/2007 | Paden et al. |

(56) References Cited

U.S. PATENT DOCUMENTS

| | | |
|---|---|---|
| 2007/0249941 A1 | 10/2007 | Salehi et al. |
| 2007/0260242 A1 | 11/2007 | Dycus et al. |
| 2007/0265560 A1 | 11/2007 | Soltani et al. |
| 2007/0265613 A1 | 11/2007 | Edelstein et al. |
| 2007/0265616 A1 | 11/2007 | Couture et al. |
| 2007/0270651 A1 | 11/2007 | Gilad et al. |
| 2007/0275348 A1 | 11/2007 | Lemon |
| 2007/0276424 A1 | 11/2007 | Mikkaichi et al. |
| 2007/0287933 A1 | 12/2007 | Phan et al. |
| 2008/0015413 A1 | 1/2008 | Barlow et al. |
| 2008/0015575 A1 | 1/2008 | Odom et al. |
| 2008/0058775 A1 | 3/2008 | Darian et al. |
| 2008/0058845 A1 | 3/2008 | Shimizu et al. |
| 2008/0071269 A1 | 3/2008 | Hilario et al. |
| 2008/0082039 A1 | 4/2008 | Babaev |
| 2008/0082098 A1 | 4/2008 | Tanaka et al. |
| 2008/0114355 A1 | 5/2008 | Whayne et al. |
| 2008/0147058 A1 | 6/2008 | Horrell et al. |
| 2008/0147062 A1 | 6/2008 | Truckai et al. |
| 2008/0171938 A1 | 7/2008 | Masuda et al. |
| 2008/0177268 A1 | 7/2008 | Daum et al. |
| 2008/0188755 A1 | 8/2008 | Hart |
| 2008/0200940 A1 | 8/2008 | Eichmann et al. |
| 2008/0208231 A1 | 8/2008 | Ota et al. |
| 2008/0214967 A1 | 9/2008 | Aranyi et al. |
| 2008/0234709 A1 | 9/2008 | Houser |
| 2008/0281200 A1 | 11/2008 | Voic et al. |
| 2008/0281315 A1 | 11/2008 | Gines |
| 2008/0287948 A1 | 11/2008 | Newton et al. |
| 2008/0300588 A1 | 12/2008 | Groth et al. |
| 2008/0312502 A1 | 12/2008 | Swain et al. |
| 2009/0012516 A1 | 1/2009 | Curtis et al. |
| 2009/0048589 A1 | 2/2009 | Takashino et al. |
| 2009/0076506 A1 | 3/2009 | Baker |
| 2009/0082716 A1 | 3/2009 | Akahoshi |
| 2009/0082766 A1 | 3/2009 | Unger et al. |
| 2009/0143678 A1 | 6/2009 | Keast et al. |
| 2009/0182322 A1 | 7/2009 | D'Amelio et al. |
| 2009/0182331 A1 | 7/2009 | D'Amelio et al. |
| 2009/0182332 A1 | 7/2009 | Long et al. |
| 2009/0248021 A1 | 10/2009 | McKenna |
| 2009/0254080 A1 | 10/2009 | Honda |
| 2009/0270771 A1 | 10/2009 | Takahashi |
| 2009/0270853 A1 | 10/2009 | Yachi et al. |
| 2009/0287205 A1 | 11/2009 | Ingle |
| 2010/0036370 A1 | 2/2010 | Mirel et al. |
| 2010/0081863 A1 | 4/2010 | Hess et al. |
| 2010/0081864 A1 | 4/2010 | Hess et al. |
| 2010/0081883 A1 | 4/2010 | Murray et al. |
| 2010/0094323 A1 | 4/2010 | Isaacs et al. |
| 2010/0158307 A1 | 6/2010 | Kubota et al. |
| 2010/0187283 A1 | 7/2010 | Crainich et al. |
| 2010/0204802 A1 | 8/2010 | Wilson et al. |
| 2010/0222752 A1 | 9/2010 | Collins, Jr. et al. |
| 2010/0274278 A1 | 10/2010 | Fleenor et al. |
| 2010/0280368 A1 | 11/2010 | Can et al. |
| 2010/0298743 A1 | 11/2010 | Nield et al. |
| 2011/0009857 A1 | 1/2011 | Subramaniam et al. |
| 2011/0028964 A1 | 2/2011 | Edwards |
| 2011/0087224 A1 | 4/2011 | Cadeddu et al. |
| 2011/0257680 A1 | 10/2011 | Reschke et al. |
| 2011/0270245 A1 | 11/2011 | Horner et al. |
| 2011/0278343 A1 | 11/2011 | Knodel et al. |
| 2011/0284014 A1 | 11/2011 | Cadeddu et al. |
| 2011/0290856 A1 | 12/2011 | Shelton, IV et al. |
| 2011/0295295 A1 | 12/2011 | Shelton, IV et al. |
| 2011/0306967 A1 | 12/2011 | Payne et al. |
| 2011/0313415 A1 | 12/2011 | Fernandez et al. |
| 2012/0016413 A1 | 1/2012 | Timm et al. |
| 2012/0022519 A1 | 1/2012 | Huang et al. |
| 2012/0022526 A1 | 1/2012 | Aldridge et al. |
| 2012/0041358 A1 | 2/2012 | Mann et al. |
| 2012/0078244 A1 | 3/2012 | Worrell et al. |
| 2012/0085358 A1 | 4/2012 | Cadeddu et al. |
| 2012/0109186 A1 | 5/2012 | Parrott et al. |
| 2012/0116222 A1 | 5/2012 | Sawada et al. |
| 2012/0116265 A1 | 5/2012 | Houser et al. |
| 2012/0265241 A1 | 10/2012 | Hart et al. |
| 2012/0296371 A1 | 11/2012 | Kappus et al. |
| 2013/0023925 A1 | 1/2013 | Mueller |
| 2013/0035685 A1 | 2/2013 | Fischer et al. |
| 2013/0123776 A1 | 5/2013 | Monson et al. |
| 2013/0158659 A1 | 6/2013 | Bergs et al. |
| 2013/0158660 A1 | 6/2013 | Bergs et al. |
| 2013/0253256 A1 | 9/2013 | Griffith et al. |
| 2013/0296843 A1 | 11/2013 | Boudreaux et al. |
| 2014/0001231 A1 | 1/2014 | Shelton, IV et al. |
| 2014/0001234 A1 | 1/2014 | Shelton, IV et al. |
| 2014/0005640 A1 | 1/2014 | Shelton, IV et al. |
| 2014/0005678 A1 | 1/2014 | Shelton, IV et al. |
| 2014/0005702 A1 | 1/2014 | Timm et al. |
| 2014/0005705 A1 | 1/2014 | Weir et al. |
| 2014/0005718 A1 | 1/2014 | Shelton, IV et al. |
| 2014/0014544 A1 | 1/2014 | Bugnard et al. |
| 2014/0194864 A1 | 7/2014 | Martin et al. |
| 2014/0194874 A1 | 7/2014 | Dietz et al. |
| 2014/0194875 A1 | 7/2014 | Reschke et al. |
| 2014/0207135 A1 | 7/2014 | Winter |
| 2014/0263541 A1 | 9/2014 | Leimbach et al. |
| 2014/0263552 A1 | 9/2014 | Hall et al. |
| 2015/0032150 A1 | 1/2015 | Ishida et al. |
| 2015/0080876 A1 | 3/2015 | Worrell et al. |
| 2015/0257819 A1 | 9/2015 | Dycus et al. |
| 2015/0272571 A1 | 10/2015 | Leimbach et al. |
| 2015/0272659 A1 | 10/2015 | Boudreaux et al. |
| 2015/0327918 A1 | 11/2015 | Sobajima et al. |
| 2016/0045248 A1 | 2/2016 | Unger et al. |
| 2016/0051316 A1 | 2/2016 | Boudreaux |
| 2016/0066980 A1 | 3/2016 | Schall et al. |
| 2016/0143687 A1 | 5/2016 | Hart et al. |
| 2016/0157923 A1 | 6/2016 | Ding |
| 2016/0157927 A1 | 6/2016 | Corbett et al. |
| 2016/0175029 A1 | 6/2016 | Witt et al. |
| 2016/0199124 A1 | 7/2016 | Thomas et al. |
| 2016/0199125 A1 | 7/2016 | Jones |
| 2016/0270842 A1 | 9/2016 | Strobl et al. |
| 2016/0270843 A1 | 9/2016 | Boudreaux et al. |
| 2016/0278848 A1 | 9/2016 | Boudreaux et al. |
| 2016/0296270 A1 | 10/2016 | Strobl et al. |
| 2017/0056097 A1 | 3/2017 | Monson et al. |
| 2017/0105787 A1 | 4/2017 | Witt et al. |
| 2017/0105789 A1 | 4/2017 | Boudreaux et al. |
| 2017/0135751 A1 | 5/2017 | Rothweiler et al. |
| 2017/0164972 A1 | 6/2017 | Johnson et al. |
| 2017/0189102 A1 | 7/2017 | Hibner et al. |
| 2017/0312014 A1 | 11/2017 | Strobl et al. |
| 2017/0312015 A1 | 11/2017 | Worrell et al. |
| 2017/0312017 A1 | 11/2017 | Trees et al. |
| 2017/0312018 A1 | 11/2017 | Trees et al. |
| 2017/0312019 A1 | 11/2017 | Trees et al. |
| 2017/0325878 A1 | 11/2017 | Messerly et al. |
| 2017/0367751 A1 | 12/2017 | Ruddenklau et al. |
| 2018/0085156 A1 | 3/2018 | Witt et al. |
| 2018/0125571 A1 | 5/2018 | Witt et al. |
| 2018/0228530 A1 | 8/2018 | Yates et al. |
| 2018/0263683 A1 | 9/2018 | Renner et al. |
| 2018/0280075 A1 | 10/2018 | Nott et al. |
| 2019/0000468 A1 | 1/2019 | Adams et al. |
| 2019/0000470 A1 | 1/2019 | Yates et al. |
| 2019/0000528 A1 | 1/2019 | Yates et al. |
| 2019/0000530 A1 | 1/2019 | Yates et al. |
| 2019/0000555 A1 | 1/2019 | Schings et al. |
| 2019/0099209 A1 | 4/2019 | Witt et al. |
| 2019/0099212 A1 | 4/2019 | Davison et al. |
| 2019/0099213 A1 | 4/2019 | Witt et al. |
| 2019/0099217 A1 | 4/2019 | Witt et al. |

FOREIGN PATENT DOCUMENTS

| | | |
|---|---|---|
| CN | 2868227 Y | 2/2007 |
| DE | 4300307 A1 | 7/1994 |
| DE | 29623113 U1 | 10/1997 |
| DE | 20004812 U1 | 9/2000 |
| DE | 10201569 A1 | 7/2003 |

(56) References Cited

FOREIGN PATENT DOCUMENTS

| | | |
|---|---|---|
| DE | 102005032371 A1 | 1/2007 |
| EP | 0171967 A2 | 2/1986 |
| EP | 0705571 A1 | 4/1996 |
| EP | 1862133 A1 | 12/2007 |
| EP | 2060238 A1 | 5/2009 |
| EP | 1747761 B1 | 10/2009 |
| EP | 1767164 B1 | 1/2013 |
| EP | 2578172 A2 | 4/2013 |
| ES | 2419159 A2 | 8/2013 |
| GB | 2032221 A | 4/1980 |
| JP | S537994 A | 1/1978 |
| JP | H08229050 A | 9/1996 |
| JP | 2002186627 A | 7/2002 |
| JP | 2009213878 A | 9/2009 |
| JP | 2010057926 A | 3/2010 |
| WO | WO-8103272 A1 | 11/1981 |
| WO | WO-9314708 A1 | 8/1993 |
| WO | WO-9800069 A1 | 1/1998 |
| WO | WO-9923960 A1 | 5/1999 |
| WO | WO-0024330 A1 | 5/2000 |
| WO | WO-0128444 A1 | 4/2001 |
| WO | WO-02080794 A1 | 10/2002 |
| WO | WO-2004078051 A2 | 9/2004 |
| WO | WO-2008130793 A1 | 10/2008 |
| WO | WO-2009067649 A2 | 5/2009 |
| WO | WO-2010104755 A1 | 9/2010 |
| WO | WO-2011008672 A2 | 1/2011 |
| WO | WO-2011044343 A2 | 4/2011 |
| WO | WO-2011144911 A1 | 11/2011 |
| WO | WO-2012044606 A2 | 4/2012 |
| WO | WO-2012061638 A1 | 5/2012 |
| WO | WO-2013131823 A1 | 9/2013 |

OTHER PUBLICATIONS

Sherrit et al., "Novel Horn Designs for Ultrasonic/Sonic Cleaning Welding, Soldering, Cutting and Drilling," Proc. SPIE Smart Structures Conference, vol. 4701, Paper No. 34, San Diego, CA, pp. 353-360, Mar. 2002.
Lim et al., "A Review of Mechanism Used in Laparoscopic Surgical Instruments," Mechanism and Machine Theory, vol. 38, pp. 1133-1147, (2003).
Gooch et al., "Recommended Infection-Control Practices for Dentistry, 1993," Published: May 28, 1993; [retrieved on Aug. 23, 2008]. Retrieved from the internet: URL: http//wonder.cdc.gov/wonder/prevguid/p0000191/p0000191.asp (15 pages).
Dean, D.A., "Electrical Impedance Spectroscopy Study of Biological Tissues," J. Electrostat, 66(34), Mar. 2008, pp. 165-177. Accessed Apr. 10, 2018: https://www.ncbi.nlm.nih.gov/pmc/articles/PMC2597841/.
Hörmann et al., "Reversible and irreversible denaturation of collagen fibers." Biochemistry, 10, pp. 932-937 (1971).
Covidien Brochure, The LigaSure Precise™ Instrument, dated Mar. 2011 (2 pages).
AST Products, Inc., "Principles of Video Contact Angle Analysis," 20 pages, (2006).
Leonard I. Malis, M.D., "The Value of Irrigation During Bipolar Coagulation," 1989.
Abbott, et al. Proceedings of the 2007 IEEEIRDJ International Conference on Intelligent Robots and Systems. 410-416, 2007.
Cadeddu et al., "Magnetic positioning system for trocarless laparoscopic instruments," American College of Surgeons Poster, 2004.
Cadeddu et al., "Novel magnetically guided intra-abdominal camera to facilitate laparoendoscopic single site surgery: initial human experience," Surgical Endoscopy, SAGES Oral Manuscript, 2009.
Cadeddu et al., "Transabdominal magnetic anchoring system for trocar-less laparoscopic surgery," American Urological Association Poster, 2002.
Cadeddu et al., "Transabdominal magnetic anchoring system for trocar-less laparoscopic surgery," Journal of Urology Abstract, 2002.
Castellvi et al., "Completely transvaginal NOTES cholecystectomy in a porcine model using novel endoscopic instrumentation," Accepted for Poster Presentation, SAGES Annual Meeting, 2009.
Castellvi et al., "Hybrid transgastric NOTES cholecystectomy in a porcine model using a magnetically anchored cautery and novel instrumentation," Submitted for Presentation, ASGE, 2009.
Castellvi et al., "Hybrid transvaginal Notes sleeve gastrectomy in a porcine model using a magnetically anchored camera and novel instrumentation," Accepted for Poster Presentation, SAGES Annual Meeting, 2009.
Duchene et al., "Magnetic positioning system for trocarless laparoscopic instruments," Engineering and Urology Society Poster, 2004.
Fernandez et al., "Development of a transabdominal anchoring system for trocar-less laparoscopic surgery," ASME Proceedings of/MECE, 2003.
Gedeon et al., "Maximizing coupling strength of magnetically anchored notes instruments: How thick can we go?" Submittedfor Presentation, Poster, SAGES Annual Meeting, 2008.
Gedeon et al., "Maximizing coupling strength of magnetically anchored notes instruments: How thick can we go?" SAGES Annual Meeting Poster, 2008.
Park et al., "Trocar-less Instrumentation for Laparoscopy: Magnetic Positioning of Intra-Abdominal Camera and Retractor", Annals of Surgery, vol. 245, No. 3, pp. 379-384, Mar. 2007.
Peirs et al., "A miniature manipulator for integration in self-propelling endoscope," Sensors and Actuators, 92:343-9, 2001.
Raman et al., "Complete transvaginal NOTES nephrectomy using magnetically anchored instrumentation," Journal of Endourology, 23(3):, 2009.367-371,2009.
Rapaccini et al., "Gastric Wall Thickness in Normal and Neoplastic Subjects: A Prospective Study Performed by Abdominal Ultrasound", Gastrointestinal Radiology, vol. 13, pp. 197-199. 1988.
Scott et al., "A randomized comparison of laparoscopic, flexible endoscopic, and wired and wireless magnetic Notes cameras on ex-vivo and in-vivo surgical performance," Digestive Disease Week (DDW), American Society for Gastrointestinal Endoscopy (ASGE) Annual Meeting Abstract, 2008.
Scott et al., "Completely transvaginal Notes cholecystectomy using magnetically anchored instruments," Surg. Endosc., 21:2308-2316, 2007.
Scott et al., "Evaluation of a novel air seal access port for transvaginal notes cholecystectomy," Submitted for Presentation, SAGES Annual Meeting, 2008.
Scott et al., "Magnetically anchored instruments for transgastric endoscopic surgery," Oral Presentation for SAGES Annual Meeting, Emerging Technology Oral Abstract ET005, 2006.
Scott et al., "Optimizing magnetically anchored camera, light source, graspers, and cautery dissector for transvaginal notes cholecystectomy," Submitted for Presentation, SAGES Annual Meeting, 2008.
Scott et al., "Short-term survival outcomes following transvaginal NOTES cholecystectomy using magnetically anchored instruments," Oral Presentation, ASGE Annual Meeting/DDW, 2007.
Scott et al., "Trans gastric, transcolonic, and transvaginal cholecystectomy using magnetically anchored instruments," SAGES Annual Meeting Poster, 2007.
Scott et al., "Transvaginal NOTES cholecystectomy using magnetically anchored instruments," Abstract for Video Submission, ASGE II1h Annual Video Forum, 2007.
Scott et al., "Transvaginal single access 'pure' Notes sleeve gastrectomy using a deployable magnetically anchored video camera," Digestive Disease Week (DDW), American Society for Gastrointestinal Endoscopy (ASGE) Annual Meeting Poster, 2008.
Swain et al., "Linear stapler formation of ileo-rectal, entero-enteral and gastrojejunal anastomoses during dual and single access 'pure' NOTES procedures: Methods, magnets and stapler modifications," Digestive Disease Week (DDW), American Society for Gastrointestinal Endoscopy (Asge) Annual Meeting Abstract, 2008.
Swain et al., "Wireless endosurgery for NOTES," Digestive Disease Week (DDW), American Society for Gastrointestinal Endoscopy (ASGE) Annual Meeting Abstract, 2008.
Tang et al., "Live video manipulator for endoscopy and natural orifice transluminal endoscopic surgery (with videos)," Gastrointestinal Endoscopy, 68:559-564, 2008.

(56) References Cited

OTHER PUBLICATIONS

Zeltser et al., "Single trocar laparoscopic nephrectomy using magnetic anchoring and guidance system in the porcine model," The Journal of Urology, 178:288-291, 2007.
Huston et al., "Magnetic and Magnetostrictive Properties of Cube Textured Nickel for Magnetostrictive Transducer Applications," IEEE Transactions on Magnetics, vol. 9(4), pp. 636-640 (Dec. 1973).
Orr et al., "Overview of Bioheat Transfer," pp. 367-384 in Optical-Thermal Response of Laser-Irradiated Tissue, A. J. Welch and M. J. C. van Gernert, eds., Plenum, New York (1995).
F. A. Duck, "Optical Properties of Tissue Including Ultraviolet and Infrared Radiation," pp. 43-71 in Physical Properties of Tissue (1990).
Campbell et al, "Thermal Imaging in Surgery," p. 19-3, in Medical Infrared Imaging, N. A. Diakides and J. D. Bronzino, Eds. (2008).
Sullivan, "Cost-Constrained Selection of Strand Diameter and Number in a Litz-Wire Transformer Winding," IEEE Transactions on Power Electronics, vol. 16, No. 2, Mar. 2001, pp. 281-288.
Covidien Brochure, [Value Analysis Brief], LigaSure Advance™ Pistol Grip, dated Rev. Apr. 2010 (7 pages).
Wright, et al., "Time-Temperature Equivalence of Heat-Induced Changes in Cells and Proteins," Feb. 1998. ASME Journal of Biomechanical Engineering, vol. 120, pp. 22-26.
Covidien Brochure, LigaSure Impact™ Instrument LF4318, dated Feb. 2013 (3 pages).
Covidien Brochure, LigaSure Atlas™ Hand Switching Instruments, dated Dec. 2008 (2 pages).
Covidien Brochure, The LigaSure™ 5 mm Blunt Tip Sealer/Divider Family, dated Apr. 2013 (2 pages).
Erbe Electrosurgery VIO® 200 S, (2012), p. 7, 12 pages, accessed Mar. 31, 2014 at http://www.erbe-med.com/erbe/media/Marketing materialien/85140170 ERBE EN VIO 200 S D027541.
Jang, J. et al. "Neuro-fuzzy and Soft Computing." Prentice Hall, 1997, pp. 13-89, 199-293, 335393, 453-496, 535-549.
Sullivan, "Optimal Choice for Number of Strands in a Litz-Wire Transformer Winding," IEEE Transactions on Power Electronics, vol. 14, No. 2, Mar. 1999, pp. 283-291.
Weir, C.E., "Rate of shrinkage of tendon collagen—heat, entropy and free energy of activation of the shrinkage of untreated tendon. Effect of acid salt, pickle, and tannage on the activation of tendon collagen." Journal of the American Leather Chemists Association, 44, pp. 108-140 (1949).
Henriques. F.C., "Studies in thermal injury V. The predictability and the significance of thermally induced rate processes leading to irreversible epidermal injury." Archives of Pathology, 434, pp. 489-502 (1947).
Wall et al., "Thermal modification of collagen," J Shoulder Elbow Surg, No. 8, pp. 339-344 (Jul./Aug. 1999).
Arnoczky et al., "Thermal Modification of Conective Tissues: Basic Science Considerations and Clinical Implications," J. Am Acad Orthop Surg, vol. 8, No. 5, pp. 305-313 (Sep./Oct. 2000).
Chen et al., "Heat-Induced Changes in the Mechanics of a Collagenous Tissue: Isothermal Free Shrinkage," Transactions of the ASME, vol. 119, pp. 372-378 (Nov. 1997).
Chen et al., "Heat-Induced Changes in the Mechanics of a Collagenous Tissue: Isothermal, Isotonic Shrinkage," Transactions of the ASME, vol. 120, pp. 382-388 (Jun. 1998).
Chen et al., "Phenomenological Evolution Equations for Heat-Induced Shrinkage of a Collagenous Tissue," IEEE Transactions on Biomedical Engineering, vol. 45, No. 10, pp. 1234-1240 (Oct. 1998).
Harris et al., "Kinetics of Thermal Damage to a Collagenous Membrane Under Biaxial Isotonic Loading," IEEE Transactions on Biomedical Engineering, vol. 51, No. 2, pp. 371-379 (Feb. 2004).
Harris et al., "Altered Mechanical Behavior of Epicardium Due to Isothermal Heating Under Biaxial Isotonic Loads," Journal of Biomechanical Engineering, vol. 125, pp. 381-388 (Jun. 2003).
Lee et al., "A multi-sample denaturation temperature tester for collagenous biomaterials," Med. Eng. Phy., vol. 17, No. 2, pp. 115-121 (Mar. 1995).
Moran et al., "Thermally Induced Shrinkage of Joint Capsule," Clinical Orthopaedics and Related Research, No. 281, pp. 248-255 (Dec. 2000).
Wells et al., "Altered Mechanical Behavior of Epicardium Under Isothermal Biaxial Loading," Transactions of the ASME, Journal of Biomedical Engineering, vol. 126, pp. 492-497 (Aug. 2004).
Gibson, "Magnetic Refrigerator Successfully Tested," U.S. Department of Energy Research News, accessed online on Aug. 6, 2010 at http://www.eurekalert.org/features/doe/2001-11/dl-mrs062802.php (Nov. 1, 2001).
Humphrey, J.D., "Continuum Thermomechanics and the Clinical Treatment of Disease and Injury," Appl. Mech. Rev., vol. 56, No. 2 pp. 231-260 (Mar. 2003).
National Semiconductors Temperature Sensor Handbook—http://www.national.com/appinfo/tempsensors/files/temphb.pdf; accessed online: Apr. 1, 2011.
Hayashi et al., "The Effect of Thermal Heating on the Length and Histologic Properties of the Glenohumeral Joint Capsule," American Journal of Sports Medicine, vol. 25, Issue 1, 11 pages (Jan. 1997), URL: http://www.mdconsult.com/das/article/body/156183648-2/jorg=journal&source=MI&sp=1 . . . , accessed Aug. 25, 2009.
Douglas, S.C. "Introduction to Adaptive Filter". Digital Signal Processing Handbook. Ed. Vijay K. Madisetti and Douglas B. Williams. Boca Raton: CRC Press LLC, 1999.
Chen et al., "Heat-induced changes in the mechanics of a collagenous tissue: pseudoelastic behavior at 37° C.," Journal of Biomechanics, 31, pp. 211-216 (1998).
Kurt Gieck & Reiner Gieck, *Engineering Formulas* § Z.7 (7th ed. 1997).
Glaser and Subak-Sharpe,Integrated Circuit Engineering, Addison-Wesley Publishing, Reading, MA (1979). (book—not attached).
https://www.kjmagnetics.com/fieldcalculator.asp, retrieved Jul. 11, 2016, backdated to Nov. 11, 2011 via https://web.archive.org/web/20111116164447/http://www.kjmagnetics.com/fieldcalculator.asp.

* cited by examiner

HIGH POWER BATTERY POWERED RF AMPLIFIER TOPOLOGY

CROSS-REFERENCE TO RELATED APPLICATION

The present application is a continuation application claiming priority under 35 U.S.C. § 120 to U.S. patent application Ser. No. 14/579,543, entitled HIGH POWER BATTERY POWERED RF AMPLIFIER TOPOLOGY, filed Dec. 22, 2014, which issued on Dec. 25, 2018 as U.S. Pat. No. 10,159,524, the entire disclosure of which is hereby incorporated by reference herein.

INTRODUCTION

The present disclosure relates to the design of high-power radiofrequency amplifiers for use in electrosurgical instruments that employ radiofrequency energy to cauterize or coagulate tissue.

Conventional corded electrosurgical instruments are large in size, have large power supplies and control electronics, and take up a lot of space in the operating room. Corded electrosurgical instruments are particularly cumbersome and difficult to use during a surgical procedure in part due to tethering of the hand-held electrosurgical instrument to the power supply and control electronics and the potential for cord entanglement. Some of these deficiencies have been overcome by providing battery powered hand-held electrosurgical instruments in which the power and control electronics are mounted within the instrument itself, such as within the handle of the instrument, to reduce the size of the electrosurgical instrument and make such instruments easier to use during surgical procedures.

Electrosurgical medical instruments generally include an end effector having an electrical contact, a radiofrequency (RF) generation circuit for generating an RF drive signal and to provide the RF drive signal to the at least one electrical contact where the RF generation circuit also includes a resonant circuit. The RF circuit includes circuitry to generate a cyclically varying signal, such as a square wave signal, from a direct current (DC) energy source and the resonant circuit is configured to receive the cyclically varying signal from the switching circuitry. The DC energy source is generally provided by one or more batteries that can be mounted in a handle portion of the housing of the instrument, for example.

Batteries mounted within the electrosurgical instrument have several limitations. For example, the amount of power the batteries provide must be balanced against their weight and size. Thus electrosurgical instruments employing RF energy typically include a high-power RF amplifier, for instance, one producing 5A RMS output, 300 W, at 170V RMS.

The design of high-power RF amplifiers, specifically the design of the output transformer, is complicated by the relatively low voltage provided by battery packs that are practical for handheld devices meant for possibly delicate uses. Such battery packs usually provide voltage in multiples of 4.2V (i.e. LiIon cell potential). The upper practical limit for handled devices is up to five cells in series—for example, in a 2P5S (sets of two parallel cells, five sets in a series string)—due to space and weight constraints. Even with a 2P5S battery configuration, selecting a workable turns ratio for the output transformer is at best a compromise between the maximum allowable primary current when in current limit mode and the need for a reasonable turns ratio for generating 170-250V RMS in the voltage control region of an electrosurgical device's power curve. The present disclosure provides a compact, optimally performing high power RF amplifier with significantly less compromise in the design of the output transformer. The present disclosure provides systems and methods for changing the turns ratio at will, synchronously with the carrier frequency of the energy device. Thus it is possible to adapt to the requirements of each region of an electrosurgical or ultrasonic power curve (current limit, power limit and voltage limit).

SUMMARY

In various embodiments, a control circuit for a radio frequency drive of an electrosurgical device is disclosed. The control circuit comprises a voltage data input configured to receive voltge data from a voltage sensing circuit, a current data input configured to receive current data from a current sensing circuit, and a switching signal output configured to source a switching signal to the radio frequency drive of the electrosurgical device. The control circuit is configured to adjust a frequency drive of the electrosurgical device. The control circuit is configured to adjust a frequency of the switching signal based on the voltage data and the current data. The radio frequency drive comprises a transformer. The transformer comprises a first tap including a first half bridge driver, a second tap including a second half bridge driver, a third tap including a third half bridge driver, a first portion of a primary coil located between the first tap and the second tap, a second portion of the primary coil located between the second tap and the third tap and the second tap, a second portion of the primary coil located between the second tap and the third tap, and a secondary coil. The first, second, and third half bridge drivers are configured to selectively turn on or turn off the first, second, and third taps, respectively. Two of the first, second, and third taps are selected to drive the primary coil between the two selected taps, which allows the transformer to provide a plurality of winding ratio values. A number of coil turns of the primary coil between the two selected taps and a number of coil turns of the secondary coil determine an overall winding ratio value of the transformer. The overall winding ratio value is one of the plurality of winding ratio values provided by the transformer.

In various embodiments, a method of controlling a radio frequency drive circuit of an electrosurgical device is disclosed. The method comprises sampling, by a synchronous I/Q sampling circuit, a plurality of output voltage values of an output voltage of the electrosurgical device, sampling, by the synchronous I/Q sampling circuit, a plurality of output current values of an output current of the electrosurgical device, and sourcing, by a square wave generation module, a switching signal to drive the radio frequency drive circuit. The output voltage and the output current are sourced by the radio frequency drive circuit comprising a transformer. The transformer further comprises a first tap including a first half bridge driver, a second tap including a second half bridge driver, a third tap including a third half bridge driver, a first portion of a primary coil located between the first tap and the second tap, a second portion of the primary coil located between the second tap and the third tap, and a secondary coil, wherein the first, second, and third half bridge drivers are configured to selectively turn on or turn off the first, second, and thrid taps, respectively. Two of the first, second, and third taps are selected to drive the primary coil between the two selected taps, which allows the transformer to provide a plurality of winding ratio values. A number of coil turns of the primary coil between the two selected taps and a number of coil turns of the secondary coil determine an overall winding ratio value of the transformer. The overall winding ratio value is one of the plurality of winding ratio values provided by the transformer.

In another embodiment, the upper and lower switch elements comprise solid-state switching elements. In another embodiment, the solid-state switching elements comprise MOSFETs.

In another embodiment, the upper and lower switch elements comprise IGBTs.

In another embodiment, the upper and lower switch elements comprise mechanical relays.

In another embodiment the current amplifier comprises a parallel capacitor on the secondary coil, such that the output produced by the amplifier is a sine wave.

In another embodiment, the minimum winding ratio is 4:1.

In another embodiment, the maximum winding ratio is 15:1.

In one embodiment, an electrosurgical medical instrument comprises a radio frequency (RF) generation circuit coupled to and operated by a battery and operable to generate an RF drive signal and to provide the RF drive signal to at least one electrical contact, wherein the RF generation circuit comprises: A current amplifier, comprising a transformer, the transformer comprising one or more taps on the primary coil, wherein each tap comprises a half bridge driver.

In another embodiment, the half bridge driver comprises an upper switch element and a lower switch element, a high-side drive input connected to the input of the upper switch element, a low-side drive input connected to the input of the lower switch element, wherein the upper and lower switch elements are connected in a cascade arrangement and the output of the half bridge driver is taken from the node between the upper and lower switch elements.

In another embodiment, the upper and lower switch elements comprise solid-state switching elements. In another embodiment, the solid-state switching elements comprise MOSFETs.

In another embodiment, the upper and lower switch elements comprise IGBTs.

In another embodiment, the upper and lower switch elements comprise mechanical relays.

In another embodiment, the medical instrument comprises a parallel capacitor on the secondary coil, such that the output produced by the amplifier is a sine wave.

In another embodiment, the minimum winding ratio is 4:1.

In another embodiment, the maximum winding ratio is 15:1.

In one embodiment, a current amplifier, comprises a transformer comprising one or more taps on the primary coil, wherein each tap comprises a half bridge driver configured to selectively turn on or turn off the tap, wherein the half bridge driver comprises an upper switch element and a lower switch element, a high-side drive input connected to the input of the upper switch element, a low-side drive input connected to the input of the lower switch element, wherein the upper and lower switch elements are connected in a cascade arrangement and the output of the half bridge driver is taken from the node between the upper and lower switch elements; and a parallel capacitor on the secondary coil, such that the output produced by the amplifier is a sine wave; wherein the minimum winding ratio is 4:1; and wherein the maximum winding ratio is 15:1.

In another embodiment, the upper and lower switch elements comprise solid-state switching elements.

FIGURES

The novel features of the embodiments described herein are set forth with particularity in the appended claims. The embodiments, however, both as to organization and methods of operation may be better understood by reference to the following description, taken in conjunction with the accompanying drawings as follows:

Figure 18:
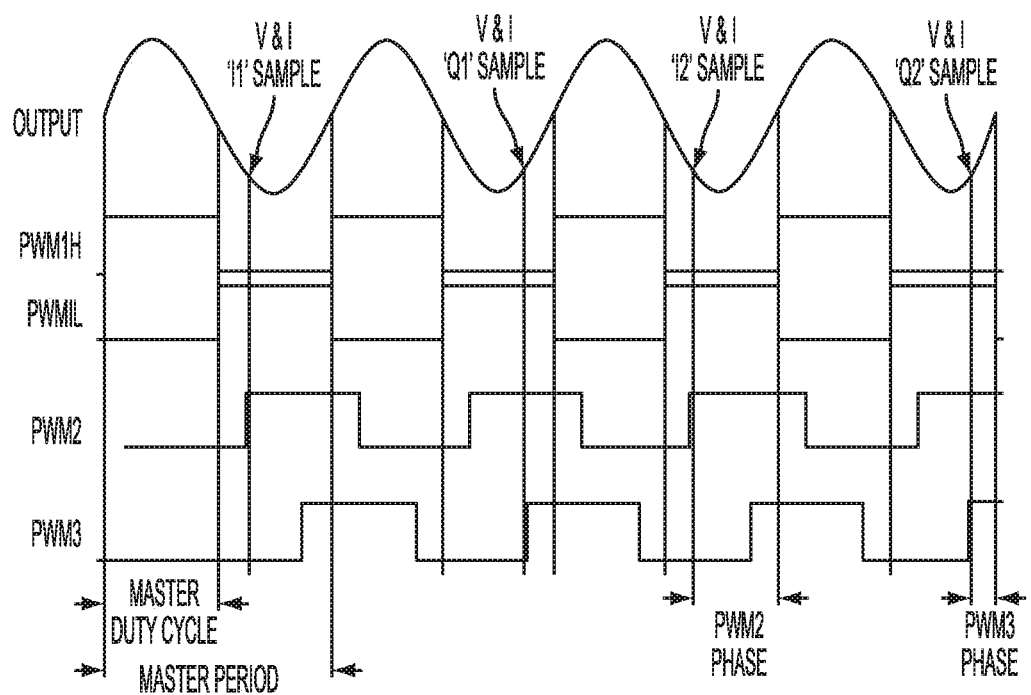
Figure 19:
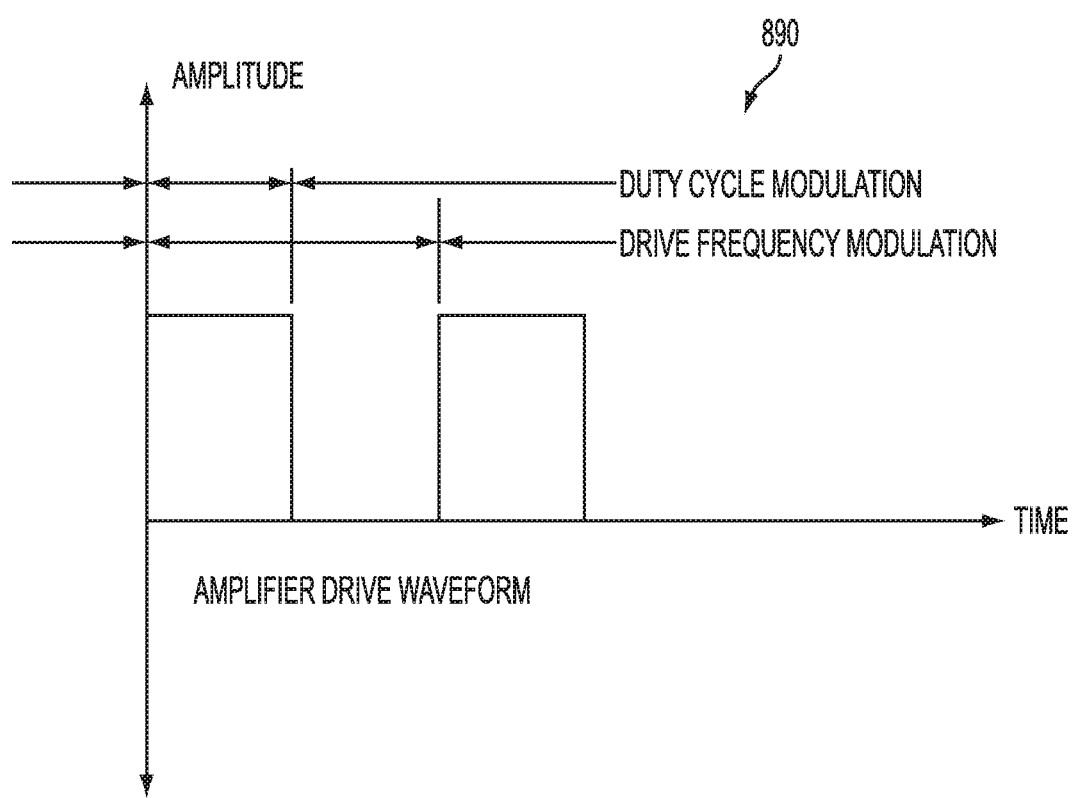

FIG. 18 is a signal plot illustrating the switching signals applied to the FETs, a sinusoidal signal representing the measured current or voltage applied to the load, and the timings when the synchronous sampling circuitry samples the sensed load voltage and load current, according to one embodiment; and FIG. 19 illustrates a drive waveform for driving the FET gate drive circuitry, according to one embodiment.

DESCRIPTION

In the following detailed description, reference is made to the accompanying drawings, which form a part hereof. In the drawings, similar symbols and reference characters typically identify similar components throughout the several views, unless context dictates otherwise. The illustrative embodiments described in the detailed description, drawings, and claims are not meant to be limiting. Other embodiments may be utilized, and other changes may be made, without departing from the scope of the subject matter presented here.

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Before explaining the various embodiments of the high power battery powered RF amplifier technology in detail, it should be noted that the various embodiments disclosed herein are not limited in their application or use to the details of construction and arrangement of parts illustrated in the accompanying drawings and description. Rather, the disclosed embodiments may be positioned or incorporated in other embodiments, variations and modifications thereof, and may be practiced or carried out in various ways. Accordingly, embodiments of the surgical devices disclosed herein are illustrative in nature and are not meant to limit the scope or application thereof. Furthermore, unless otherwise indicated, the terms and expressions employed herein have been chosen for the purpose of describing the embodiments for the convenience of the reader and are not to limit the scope thereof. In addition, it should be understood that any one or more of the disclosed embodiments, expressions of embodiments, and/or examples thereof, can be combined with any one or more of the other disclosed embodiments, expressions of embodiments, and/or examples thereof, without limitation.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument.

Also, in the following description, it is to be understood that terms such as front, back, inside, outside, top, bottom, upper, lower and the like are words of convenience and are not to be construed as limiting terms. Terminology used herein is not meant to be limiting insofar as devices described herein, or portions thereof, may be attached or utilized in other orientations. The various embodiments will be described in more detail with reference to the drawings.

Many surgical procedures require cutting or litigating blood vessels or other vascular tissue. With minimally invasive surgery, surgeons perform surgical operations through a small incision in the patient's body. As a result of the limited space, surgeons often have difficulty controlling bleeding by clamping and/or tying-off transected blood vessels. By utilizing electrosurgical instruments, such as electrosurgical forceps, a surgeon can cauterize, coagulate/desiccate, and/or simply reduce or slow bleeding by controlling the electrosurgical energy applied through jaw members of the electrosurgical forceps, otherwise referred to as clamp arms.

Electrosurgical instruments generally comprise an electronics system for generating and controlling electrosurgical energy. The electronics system comprises an RF generation circuit to generate an RF drive signal and to provide the RF drive signal to at least one electrical contact, where the RF generation circuit also includes a resonant circuit. The electronics system also comprises control elements such as one or more than one microprocessor (or micro-controller) and additional digital electronic elements to control the logical operation of the instrument.

The electronics elements of the power supply and RF amplifier sections should be designed to have the highest efficiency possible in order to minimize heat rejected into the housing of the instrument. Efficiency also provides the longest storage and operational battery life possible. As described in the embodiments illustrated in FIGS. 4-16, litz wire may be wound around a bobbin core to reduce AC losses due to high frequency RF. The litz wire construction provides greater efficiency and thus also prevents heat generation in the device.

In various embodiments, efficiency of the power supply and RF drive and control circuitry sections also may minimize the size of the battery required to fulfill the mission life, or to extend the mission life for a given size battery. In one embodiment, the battery provides a low source impedance at a terminal voltage of 12.6V (unloaded) and a 1030 mA-Hour capacity. Under load, the battery voltage is a nominal 11.1V, for example.

Radio frequency drive amplifier topologies may vary according to various embodiments. In one embodiment, for example, a series resonant approach may be employed where the operating frequency is varied to change the output voltage to force the medical instrument to operate according to a pre-programmed load curve. In a series resonant approach, the impedance of a series resonant network is at a minimum at the resonant frequency, because the reactance of the capacitive and inductive elements cancel, leaving a small real resistance. The voltage maximum for a series resonant circuit also occurs at the resonant frequency (and also depends upon the circuit Q). Accordingly, to produce a high voltage on the output, the series resonant circuit should operate closer to the resonant frequency, which increases the current draw from the DC supply (e.g., battery) to feed the RF amplifier section with the required current. Although the series resonant approach may be referred to as a resonant mode boost converter, in reality, the design is rarely operated at the resonant frequency, because that is the point of maximum voltage. The benefit of a resonant mode topology is that if it is operated very close to the resonant frequency, the switching field effect transistors (FETs) can be switched "ON" or "OFF" at either a voltage or current zero crossing, which dissipates the least amount of power in the switching FETs as is possible.

Another feature of the RF drive and control circuitry section according to one embodiment, provides a relatively high turns ratio transformer which steps up the output voltage to about 85V RMS from the nominal battery voltage of about 11.1V. This provides a more compact implementation because only one transformer and one other inductor are required. In such a circuit, high currents are necessary on the transformer primary to create the desired output voltage or current. Such device, however, cannot be operated at the resonant frequency because allowances are made to take into account for the battery voltage dropping as it is expended. Accordingly, some headroom is provided to maintain the output voltage at the required level. A more detailed description of a series resonant approach is provided in commonly assigned international PCT Patent Application No. PCT/GB2011/000778, titled "Medical Device," filed May 20, 2011, the disclosure of which is incorporated herein by reference in its entirety.

According to another embodiment, an RF instrument topology is provided for a handheld battery powered RF based generator for the electrosurgical medical instrument. Accordingly, in one embodiment, the present disclosure provides an RF instrument topology with an architecture configured such that each power section of the device operate at maximum efficiency regardless of the load resistance presented by the tissue or what voltage, current, or power level is commanded by the controller. In one embodiment, this may be implemented by employing the most efficient modalities of energy transformation presently known and by minimizing the component size to provide a small and light weight electronics package to fit within the instrument's housing, for example.

In one embodiment, the RF power electronics section of the electronics system may be partitioned as a boost mode converter, synchronous buck converter, and a parallel resonant amplifier. According to one embodiment, a resonant mode boost converter section of the medical instrument may be employed to convert the DC battery voltage to a higher DC voltage for use by the synchronous mode buck converter. One aspect to consider for achieving a predetermined efficiency of the resonant mode boost converter section is ratio between input and output voltages of the boost converter. In one embodiment, although a 10:1 ratio is achievable, the cost is that for any appreciable power on the secondary the input currents to the boost mode transformer become quite heavy, in the range of about 15-25A, depending on the load. In another embodiment a transformer turns ratio of about 5:1 is provided. It will be appreciated that transformer ratios in the range of about 5:1 to about 10:1 also may be implemented, without limitation. In a 5:1 transformer turns ratio, the design tradeoff is managing the Q of the parallel resonant output against the boost ratio. The resonant output network performs two functions. First, it filters the square, digital pulses from the Class D output amplifier and removes all but the fundamental frequency sine wave from the output. Second, it provides a passive voltage gain due to the Q of the filter network. In other words, current from the amplifier is turned into output voltage, at a gain determined by the circuit's unloaded Q and the load resistance, which affects the Q of the circuit.

Another aspect to consider for achieving a predetermined efficiency in the resonant mode boost converter section is to utilize a full bridge switcher topology, which allows half the turns ratio for the boost transformer for the same input voltage. The tradeoff is that this approach may require additional FET transistors, e.g., an additional two FETs are required over a half bridge approach, for example. Presently available switchmode FETs, however, are relatively small, and while the gate drive power is not negligible, it provides a reasonable design tradeoff.

Yet another aspect to consider for achieving a predetermined efficiency in the resonant mode boost converter section and operating the boost converter at maximum efficiency, is to always run the circuit at the resonant frequency so that the FETs are always switching at either a voltage or current minima, whichever is selected by the designer (ZCS vs. ZVS switching), for example. This can include monitoring the resonant frequency of the converter as the load changes, and making adjustments to the switching frequency of the boost converter to allow 35 ZVS or ZCS (Zero Voltage Switching/Zero Current Switching) to occur for minimum power dissipation.

Yet another aspect to consider for achieving a predetermined efficiency in the resonant mode boost converter section is to utilize a synchronous rectifier circuit instead of a conventional full-wave diode rectifier block. Synchronous rectification employs FETs as diodes because the on-resistance of the FET is so much lower than that of even a Schottky power diode optimized for low forward voltage drop under high current conditions. A synchronous rectifier requires gate drive for the FETs and the logic to control them, but offers significant power savings over a traditional full bridge rectifier.

In accordance with various embodiments, the predetermined efficiency of a resonant mode boost converter is approximately 98-99% input to output, for example. Any suitable predetermined efficiency may be selected based on the particular implementation. Accordingly, the embodiments described herein are limited in this context.

According to one embodiment, a synchronous buck converter section of the medical instrument may be employed to reduce the DC voltage fed to the RF amplifier section to the predetermined level to maintain the commanded output power, voltage or current as dictated by the load curve, with as little loss as is possible. The buck converter is essentially an LC lowpass filter fed by a low impedance switch, along with a regulation circuit to control the switch to maintain the commanded output voltage. The operating voltage is dropped to the predetermined level commanded by the main controller, which is running the control system code to force the system to follow the assigned load curve as a function of sensed tissue resistance. In accordance with various embodiments, the predetermined efficiency of a synchronous buck regulator is approximately 99%, for example. Any suitable predetermined efficiency may be selected based on the particular implementation. Accordingly, the embodiments described herein are limited in this context.

According to one embodiment, a resonant mode RF amplifier section comprising a parallel resonant network on the RF amplifier section output is provided. In one embodiment, a predetermined efficiency may be achieved by a providing a parallel resonant network on the RF amplifier section output. The RF amplifier section may be driven at the resonant frequency of the output network, which accomplishes three things. First, the high Q network allows some passive voltage gain on the output, reducing the boost required from the boost regulator in order to produce high voltage output levels. Second, the square pulses produced by the RF amplifier section are filtered and only the fundamental frequency is allowed to pass to the output. Third, a full-bridge amplifier is switched at the resonant frequency of the output filter, which is to say at either the voltage zero crossings or the current zero crossings in order to dissipate minimum power. Accordingly, a predetermined efficiency of the RF amplifier section is approximately 98%. Gate drive losses may limit the efficiency to this figure or slightly lower. Any suitable predetermined efficiency may be selected based on the particular implementation. Accordingly, the embodiments described herein are limited in this context.

In view of the RF instrument topology and architecture described above, an overall system efficiency of approximately 0.99*0.99*0.98, which is approximately 96%, may be achieved. Accordingly, to deliver approximately 45 W, approximately 1.8 W would be dissipated by the electronics exclusive of the power required to run the main and housekeeping microprocessors, and the support circuits such as the ADC and analog amplifiers and filters. To deliver approximately 135 W, approximately 5.4 W would be dissipated. This is the amount of power that would be required to implement a large jaw class generator in a hand held electrosurgical medical instrument. Overall system efficiency would likely only be a weak function of load resistance, instead of a relatively strong one as it may be the case in some conventional instruments.

In various other embodiments of the electrosurgical medical instrument, a series resonant topology may be employed to achieve certain predetermined efficiency increase by employing a full bridge amplifier for the primary circuit and isolate the full bridge amplifier from ground to get more voltage on the primary. This provides a larger primary inductance and lower flux density due to the larger number of turns on the primary.

Figure 3:
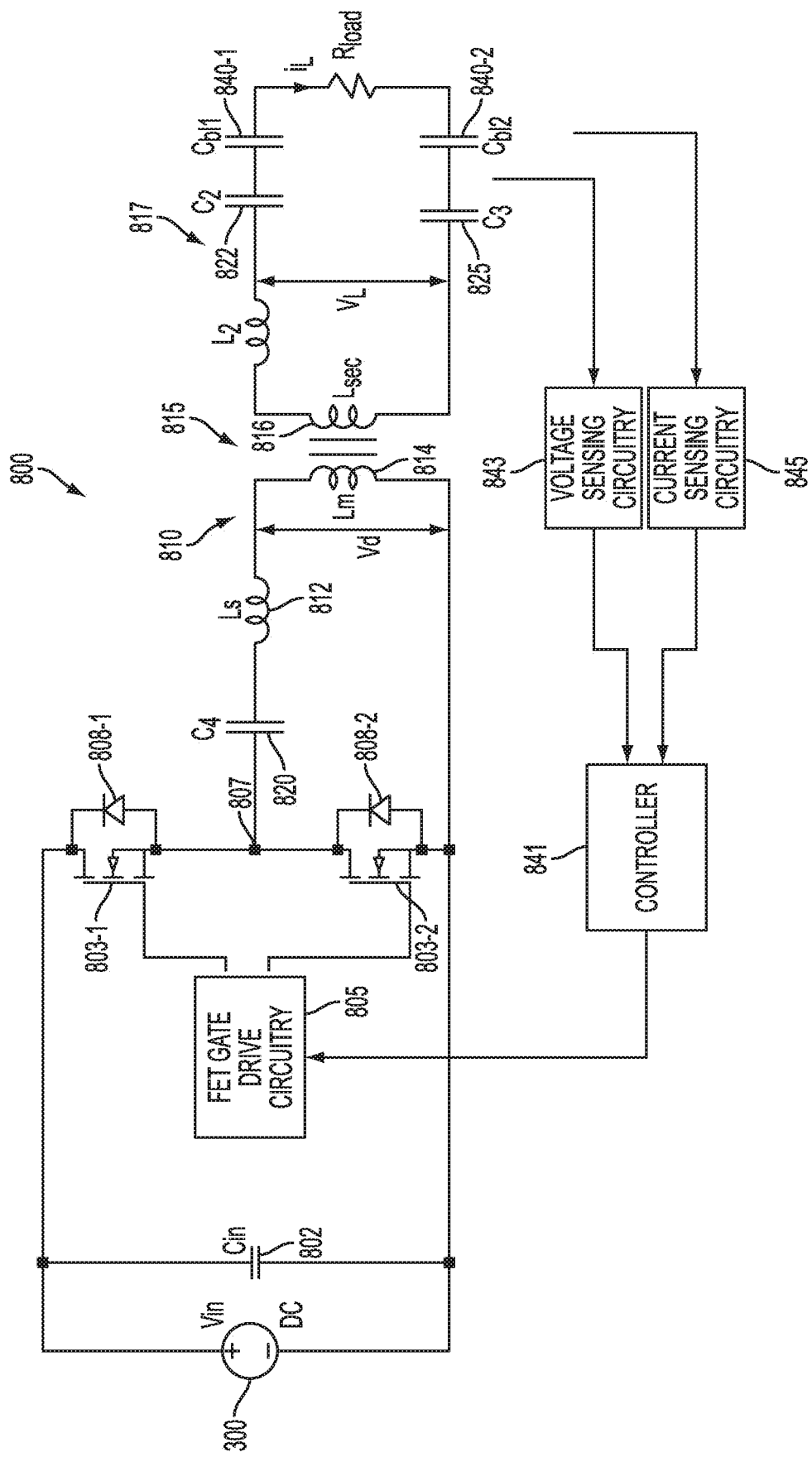
FIG. 3 illustrates an RF drive and control circuit, according to one embodiment.

FIG. 3 illustrates an RF drive and control circuit 800, according to one embodiment. FIG. 3 is a part schematic part block diagram illustrating the RF drive and control circuitry 800 used in this embodiment to generate and control the RF electrical energy supplied to the electrosurgical instrument. As will be explained in more detail below, in this embodiment, the drive circuitry 800 is a resonant mode RF amplifier comprising a parallel resonant network on the RF amplifier output and the control circuitry operates to control the operating frequency of the drive signal so that it is maintained at the resonant frequency of the drive circuit, which in turn controls the amount of power supplied to the instrument. The way that this is achieved will become apparent from the following description.

As shown in FIG. 3, the RF drive and control circuit 800 comprises a battery 300 arranged to supply, in this example, about 0V and about 12V rails. An input capacitor (Cin) 802 is connected between the 0V and the 12V for providing a low source impedance. A pair of FET switches 803-1 and 803-2 (both of which are N-channel in this embodiment to reduce power losses) is connected in series between the 0V rail and the 30 12V rail. FET gate drive circuitry 805 is provided that generates two drive signals—one for driving each of the two FETs 803. The FET gate drive circuitry 805 generates drive signals that causes the upper FET (803-1) to be on when the lower FET (803-2) is off and vice versa. This causes the node 807 to be alternately connected to the 12V rail (when the FET 803-1 is switched on) and the 0V rail (when the FET 803-2 is switched on). FIG. 3 also shows the internal parasitic diodes 808-1 and 808-2 of the corresponding FETs 803, which conduct during any periods that the FETs 803 are open.

Figure 9:
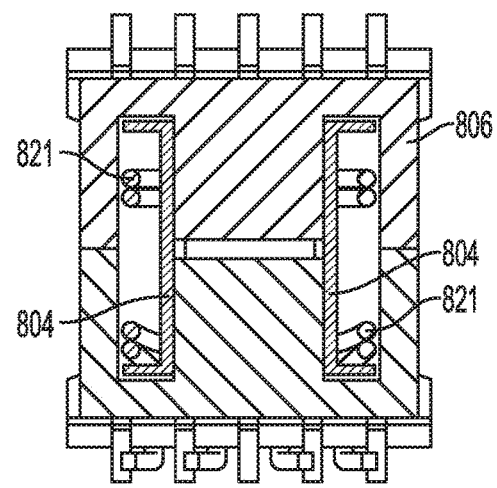
FIG. 9 illustrates a sectional view of the primary coil illustrated in FIG. 5 taken along section 28-28.

As shown in FIG. 3, the node 807 is connected to an inductor-inductor resonant circuit 810 formed by an inductor $L_s$ 812 and an inductor $L_m$ 814, which is the primary coil of a transformer 815. The FET gate driving circuitry 805 is arranged to generate drive signals at a drive frequency ($f_d$) that opens and crosses the FET switches 803 at the resonant frequency of the parallel resonant circuit 810. As a result of the resonant characteristic of the resonant circuit 810, the square wave voltage at node 807 will cause a substantially sinusoidal current at the drive frequency ($f_d$) to flow within the resonant circuit 810. As illustrated in FIG. 9, the inductor $L_m$ 814 is the primary coil of a transformer 815, the secondary coil of which is formed by inductor $L_{sec}$ 816. The inductor $L_{sec}$ 816 of the transformer 815 secondary is connected to a resonant circuit 817 formed by inductor $L_2$, capacitor $C_4$ 820, capacitor $C_2$ 822, and capacitor $C_3$ 825. The transformer 815 up-converts the drive voltage ($V_d$) across the inductor $L_m$ 814 to the voltage that is applied to the output parallel resonant circuit 817. The load voltage ($V_L$) is output by the parallel resonant circuit 817 and is applied to the load (represented by the load resistance $R_{load}$ 819 in FIG. 3) corresponding to the impedance of the forceps' jaws and any tissue or vessel gripped by the forceps 108. As shown in FIG. 3, a pair of DC blocking capacitors $C_{bl1}$ 840-1 and $C_{bl2}$ 840-2 is provided to prevent any DC signal being applied to the load 819.

In one embodiment, the transformer 815 may be implemented with a Core Diameter (mm), Wire Diameter (mm), and Gap between secondary windings in accordance with the following specifications:
Core Diameter, D (mm)
D=19.9×10−3
Wire diameter, W (mm) for 22 AWG wire
W=7.366×10−4
Gap between secondary windings, in gap=0.125
G=gap/25.4

In this embodiment, the amount of electrical power supplied to the electrosurgical instrument is controlled by varying the frequency of the switching signals used to switch the FETs 803. This works because the resonant circuit 810 acts as a frequency dependent (loss less) attenuator. The closer the drive signal is to the resonant frequency of the resonant circuit 810, the less the drive signal is attenuated. Similarly, as the frequency of the drive signal is moved away from the resonant frequency of the circuit 810, the more the drive signal is attenuated and so the power supplied to the load reduces. In this embodiment, the frequency of the switching signals generated by the FET gate drive circuitry 805 is controlled by a controller 841 based on a desired power to be delivered to the load 819 and measurements of the load voltage ($V_L$) and of the load current ($I_L$) obtained by conventional voltage sensing circuitry 843 and current sensing circuitry 845. The way that the controller 841 operates will be described in more detail below.

In one embodiment, the voltage sensing circuitry 843 and the current sensing circuitry 845 may be implemented with high bandwidth, high speed rail-to-rail amplifiers (e.g., LMH6643 by National Semiconductor). Such amplifiers, however, consume a relatively high current when they are operational. Accordingly, a power save circuit may be provided to reduce the supply voltage of the amplifiers when they are not being used in the voltage sensing circuitry 843 and the current sensing circuitry 845. In one-embodiment, a step-down regulator (e.g., LT3502 by Linear Technologies) may be employed by the power save circuit to reduce the supply voltage of the rail-to-rail amplifiers and thus extend the life of the battery 300.

In one embodiment, the transformer 815 and/or the inductor $L_s$ 812 may be implemented with a configuration of litz wire conductors to minimize the eddy-current effects in the windings of high-frequency inductive components. These effects include skin-effect losses and proximity effect losses. Both effects can be controlled by the use of litz wire, which are conductors made up of multiple individually insulated strands of wire twisted or woven together. Although the term litz wire is frequently reserved for conductors constructed according to a carefully prescribed pattern, in accordance with the present disclosure, any wire strands that are simply twisted or grouped together may be referred to as litz wire. Accordingly, as used herein, the term litz wire refers to any insulated twisted or grouped strands of wires.

By way of background, litz wire can reduce the severe eddy-current losses that otherwise limit the performance of high-frequency magnetic components, such as the transformer 815 and/or the inductor $L_s$ 812 used in the RF drive and control circuit 800 of FIG. 3. Although litz wire can be very expensive, certain design methodologies provide significant cost reduction without significant increases in loss, or more generally, enable the selection of a minimum loss design at any given cost. Losses in litz-wire transformer windings have been calculated by many authors, but relatively little work addresses the design problem of how to choose the number and diameter of strands for a particular application. Cost-constrained litz wire configurations are described in C. R. Sullivan, "Cost-Constrained Selection of Strand Wire and Number in a Litz-Wire Transformer Winding," *IEEE Transactions on Power Electronics*, vol. 16, no. 2, pp. 281-288, which is incorporated herein by reference. The choice of the degree of stranding in litz wire for a transformer winding is described in C. R. Sullivan, "Optimal Choice for Number of Strands in a Litz-Wire Transformer Winding," *IEEE Transactions on Power Electronics*, vol. 14, no. 2, pp. 283-291, which is incorporated herein by reference.

In one embodiment, the transformer 815 and/or the inductor $L_s$ 812 may be implemented with litz wire by HM Wire International, Inc., of Canton, Ohio or New England Wire Technologies of Lisbon, N.H., which has a slightly different construction in terms of the number of strands in the intermediate windings, but has the same total number of strands of either 44 gauge or 46 gauge wire by HM Wire International, Inc. Accordingly, the disclosure now turns to FIGS. 4-16, which illustrate one embodiment of the transformer 815 and the inductor $L_s$ 81 implemented with litz wire.

Figure 4:
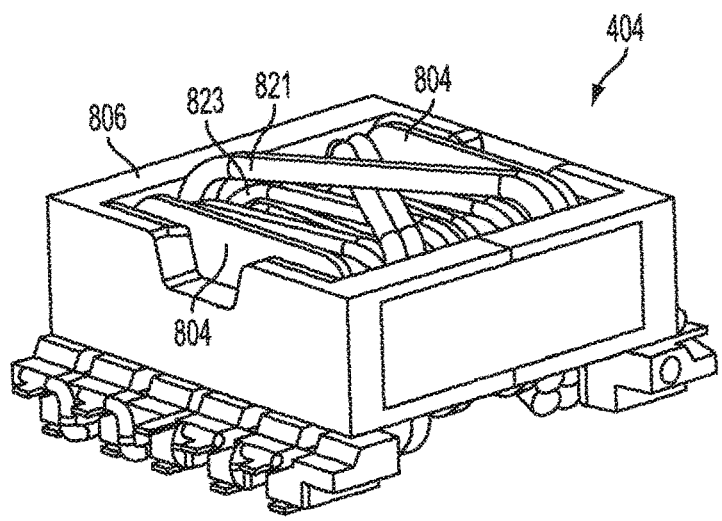
FIG. 4 illustrates a perspective view of one embodiment of the transformer shown as transformer in connection with the RF drive circuit illustrated in FIG. 3.

FIG. 4 illustrates a perspective view of one embodiment of the transformer shown as transformer 815 in connection with the RF drive circuit 800 illustrated in FIG. 3. As shown in FIG. 4, in one embodiment, the transformer 404 comprises a bobbin 804, a ferrite core 806, a primary coil 821 (e.g., inductor $L_m$ 814 in FIG. 3), and a secondary coil 823 (e.g., inductor $L_{sec}$ 816 in FIG. 3). In one embodiment, the bobbin 804 may be a 10-pin surface mounted device (SMD) provided by Ferroxcube International Holding B.V. In one embodiment, the ferrite core 806 may be an EFD 20/107 N49. In one embodiment, the transformer 815 has a power transfer of ~45 W, a maximum secondary current of ~1.5 A RMS, maximum secondary voltage of ~90V RMS, maximum primary current of ~15.5 A RMS, and a turns ratio of 20:2 (secondary turns:primary turns), for example. The operating frequency range of the transformer 404 is from ~370 kHz to ~550 kHz, and a preferred frequency of ~430 kHz. It will be appreciated that these specification are provided as examples and should not be construed to be limiting of the scope of the appended claims.

In one embodiment, the transformer 404 comprises a ferrite core material having particular characteristics. The core used for both the inductor 406 and the transformer 404, albeit with a different gap to yield the required $A_L$ for each component. $A_L$ has units of Henrys/turns$^2$, so the inductance of a winding may be found by using NTURNS$^2$*$A_L$. In one embodiment, an $A_L$ of 37 is used for the inductor 406, and an $A_L$ of 55 is used for the transformer 406. This corresponds to a gap of approximately 0.8 mm and 2.0 mm respectively, although the $A_L$ or the inductance is the parameter to which the manufacturing process controls, with the $A_L$ being an intermediate quantity that we are not measuring directly.

In one embodiment, the inductance of the inductor 406 and transformer 404 winding may be measured directly with "golden bobbins," which are squarely in the middle of the tolerance bands for the winding statistical distributions. Cores that are ground are then tested using the "golden bobbin" to assess whether the grind is good on the cores. Better results were yielded than the industry standard method, which is to fill a bobbin with as many windings as they can fit on the bobbin, and then back calculating the $A_L$ of the core, and controlling $A_L$ instead of the inductance. It was found that using a "golden bobbin" in the manufacturing process yielded better results. The bobbin is what the copper windings are secured to, and the ferrite E cores slip through a hole in the bobbin, and are secured with clips.

Figure 5:
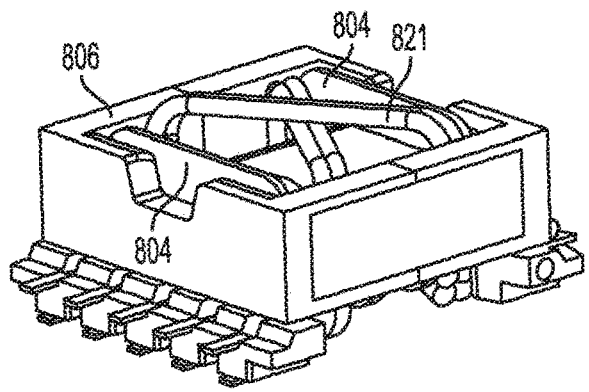
FIG. 5 illustrates a perspective view of one embodiment of the primary coil of the transformer illustrated in FIG. 4.

FIG. 5 illustrates a perspective view of one embodiment of the primary coil 821 (e.g., inductor $L_m$ 814 in FIG. 3) of the transformer 404 illustrated in FIG. 4. In one embodiment, the primary coil 821 windings may be constructed using 300 strand/46 gauge litz wire as indicated in TABLE 1 below, among other suitable configurations. In one embodiment, primary coil 821 has an inductance of ~270 nH, an AC resistance <46mΩ, and a DC resistance of ≤5 mΩ, for example.

TABLE 1

| Primary Coil 821 (Lm 814) 46 Gauge Litz Wire |
|---|
| 300 Strands 46 AWG- 24 turns per foot (TPF) |
| Single Build MW80 155° C. |
| Single Nylon Served |
| Construction: 5 × 3 × 20/46 AWG |
| Ft per lb: 412 Nominal |
| OD: 0.039" Nominal |

Figure 7:
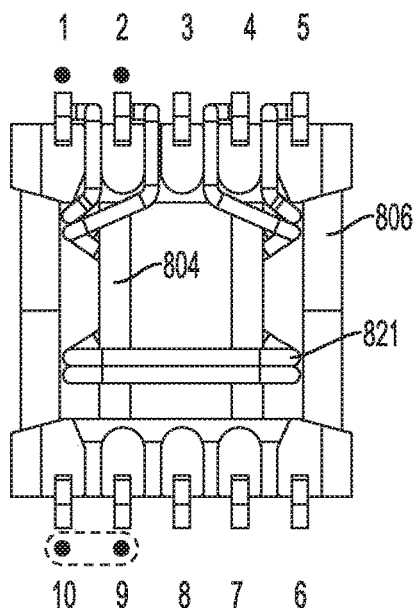
FIG. 7 illustrates a bottom view of the primary coil illustrated in FIG. 5.
Figure 8:
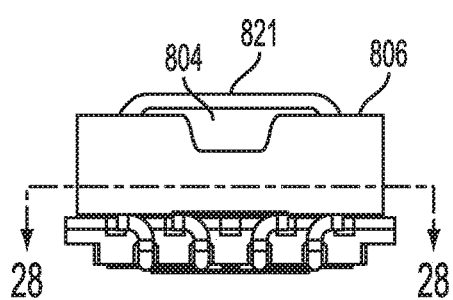
FIG. 8 illustrates a side view of the primary coil illustrated in FIG. 5.

FIG. 7 illustrates a bottom view of the primary coil 821 (e.g., inductor $L_m$ 814 in FIG. 3) illustrated in FIG. 5. FIG. 8 illustrates a side view of the primary coil 821 illustrated in FIG. 5. FIG. 9 illustrates a sectional view of the primary coil 821 illustrated in FIG. 5 taken along section 28-28.

Figure 6:
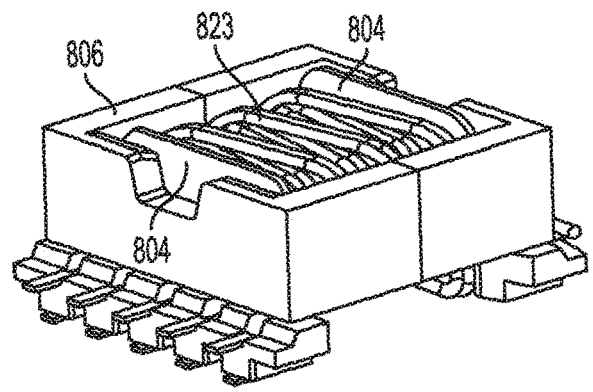
FIG. 6 illustrates a perspective view of one embodiment of a secondary coil of the transformer illustrated in FIG. 4.

FIG. 6 illustrates a perspective view of one embodiment of a secondary coil 823 (e.g., inductor $L_{sec}$ 816 in FIG. 3) of the transformer 404 illustrated in FIG. 4. In one embodiment, the secondary coil 823 windings may be constructed using 105 strand/44 gauge litz wire as indicated in TABLE 2 below, among other suitable configurations. In one embodiment, the secondary coil 823 has an inductance of 22 µH±5% @430 kHz, an AC resistance <2.5Ω, and a DC resistance ≤80 mΩ, for example.

TABLE 2

| Secondary Coil 823 (Lsec 816) 44 Gauge Litz Wire |
|---|
| 105 Strands 44 AWG 24 TPF |
| Single Build MW80 155° C. |
| Single Nylon Served |
| Construction: 5 × 21/44 AWG |
| Ft per lb: 1214 Nominal |
| OD: 0.023" Nominal |

Figure 10:
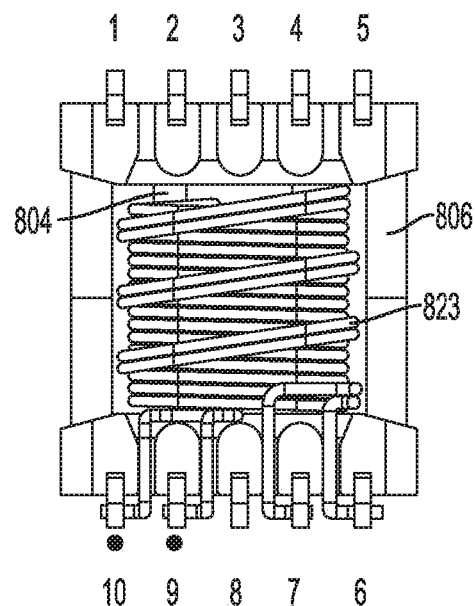
FIG. 10 illustrates a bottom view of the secondary coil illustrated in FIG. 6.
Figure 11:
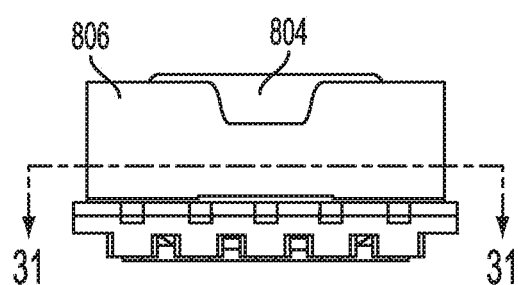
FIG. 11 illustrates a side view of the secondary coil illustrated in FIG. 6.
Figure 12:
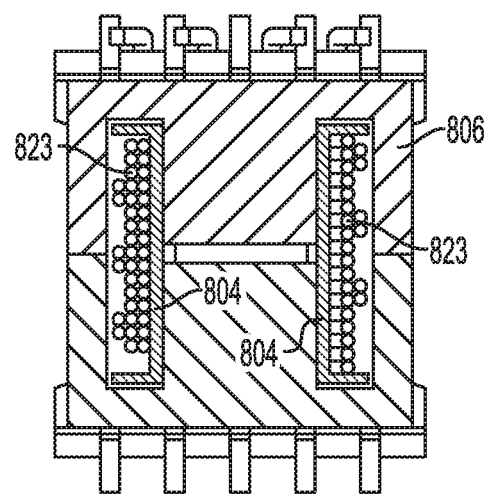
FIG. 12 illustrates a sectional view of the secondary coil illustrated in FIG. 11 taken along section 31-31.

FIG. 10 illustrates a bottom view of the secondary coil 823 (e.g., inductor $L_{sec}$ 816 in FIG. 3) illustrated in FIG. 6. FIG. 11 illustrates a side view of the secondary coil 823 illustrated in FIG. 6. FIG. 12 illustrates a sectional view of the secondary coil 8235 illustrated in FIG. 11 taken along section 31-31.

Figure 13:
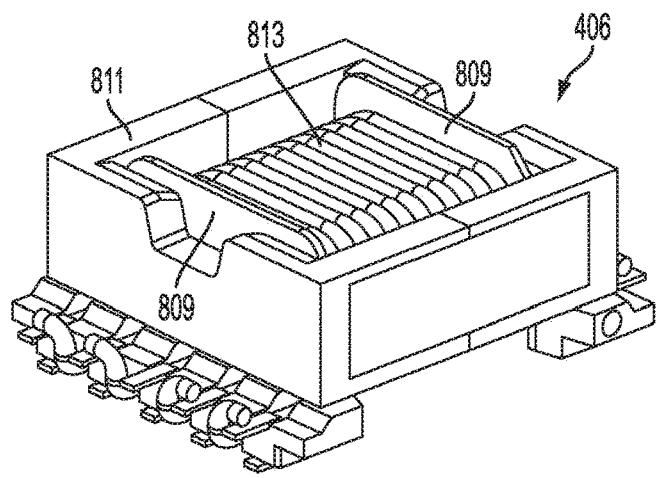
FIG. 13 is a perspective view of one embodiment of the inductor shown as inductor $L_s$ in connection with the RF drive circuit illustrated in FIG. 3.

FIG. 13 is a perspective view of one embodiment of the inductor 406 shown as inductor $L_s$ 812 in connection with the RF drive circuit 800 illustrated in FIG. 3. As shown in FIG. 13, in one embodiment, the inductor 406 comprises a bobbin 809, a ferrite core 811, and a coil 813. In one embodiment, the bobbin 809 may be a 10-pin surface mounted device (SMD) provided by Ferroxcube International Holding B.V. In one embodiment, the ferrite core 811 may be an EFD 20/107 N49. In one embodiment, the coil 813 windings may be constructed using 300 strand/46 gauge litz wire wound at 24 TPF. In one embodiment, the inductor $L_s$ 812 may have an inductance of ~345 nH±6% @430 kHz, an AC resistance <50 mΩ, and a DC resistance ≤7 mΩ, for example. The operating frequency range of the inductor $L_s$ 812 is from ~370 kHz to ~550 kHz, and a preferred frequency of ~430 kHz, and an operating current of ~15.5 A RMS. It will be appreciated that these specification are provided as examples and should not be construed to be limiting of the scope of the appended claims.

Figure 14:
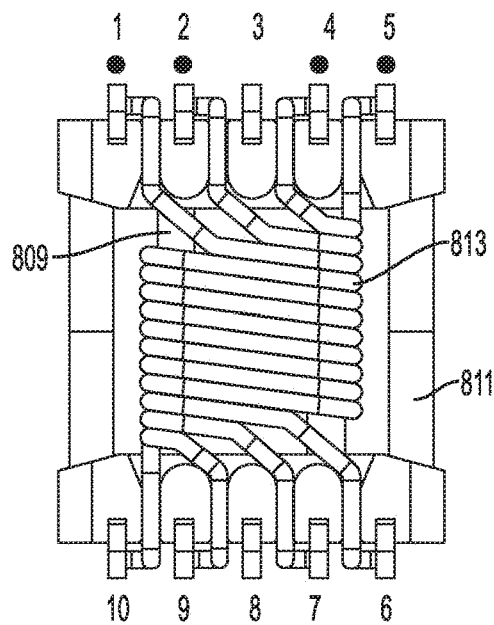
FIG. 14 illustrates a bottom view of the inductor illustrated in FIG. 13.
Figure 15:
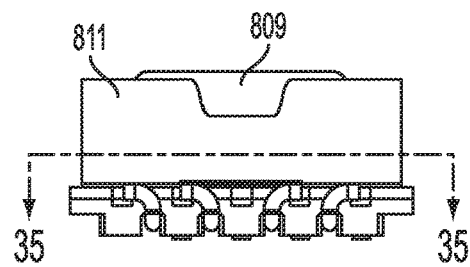
FIG. 15 illustrates a side view of the inductor illustrated in FIG. 13.
Figure 16:
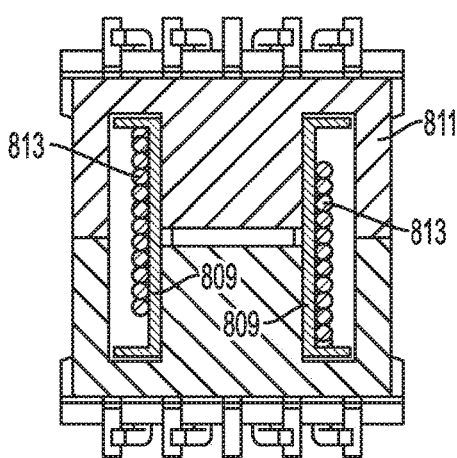
FIG. 16 illustrates a sectional view of the inductor illustrated in FIG. 15 taken along section 35-35.

FIG. 14 illustrates a bottom view of the inductor 406 (e.g., inductor $L_s$ 812 in FIG. 3) illustrated in FIG. 13. FIG. 15 illustrates a side view of the inductor 406 illustrated in FIG. 13. FIG. 16 illustrates a sectional view of the inductor 406 illustrated in FIG. 15 taken along section 35-35.

Accordingly, as described above in connection with FIGS. 4-16, in one embodiment, the transformer 404 (e.g., transformer 815) and/or the inductor 406 (e.g., inductor 812) used in the RF drive and control circuit 800 of FIG. 3 may be implemented with litz wire. One litz wire configuration may be produced by twisting 21 strands of 44 AWG SPN wire at 18 twists per foot (left direction twisting). Another litz wire configuration may be produced by twisting 5×21/44 AWG (105/44 AWG SPN), also at 18 twists per foot (left direction twisting). Other litz wire configurations include 300/46 AWG litz wire as well as 46 AWG or finer gauge size wire.

Figure 17:
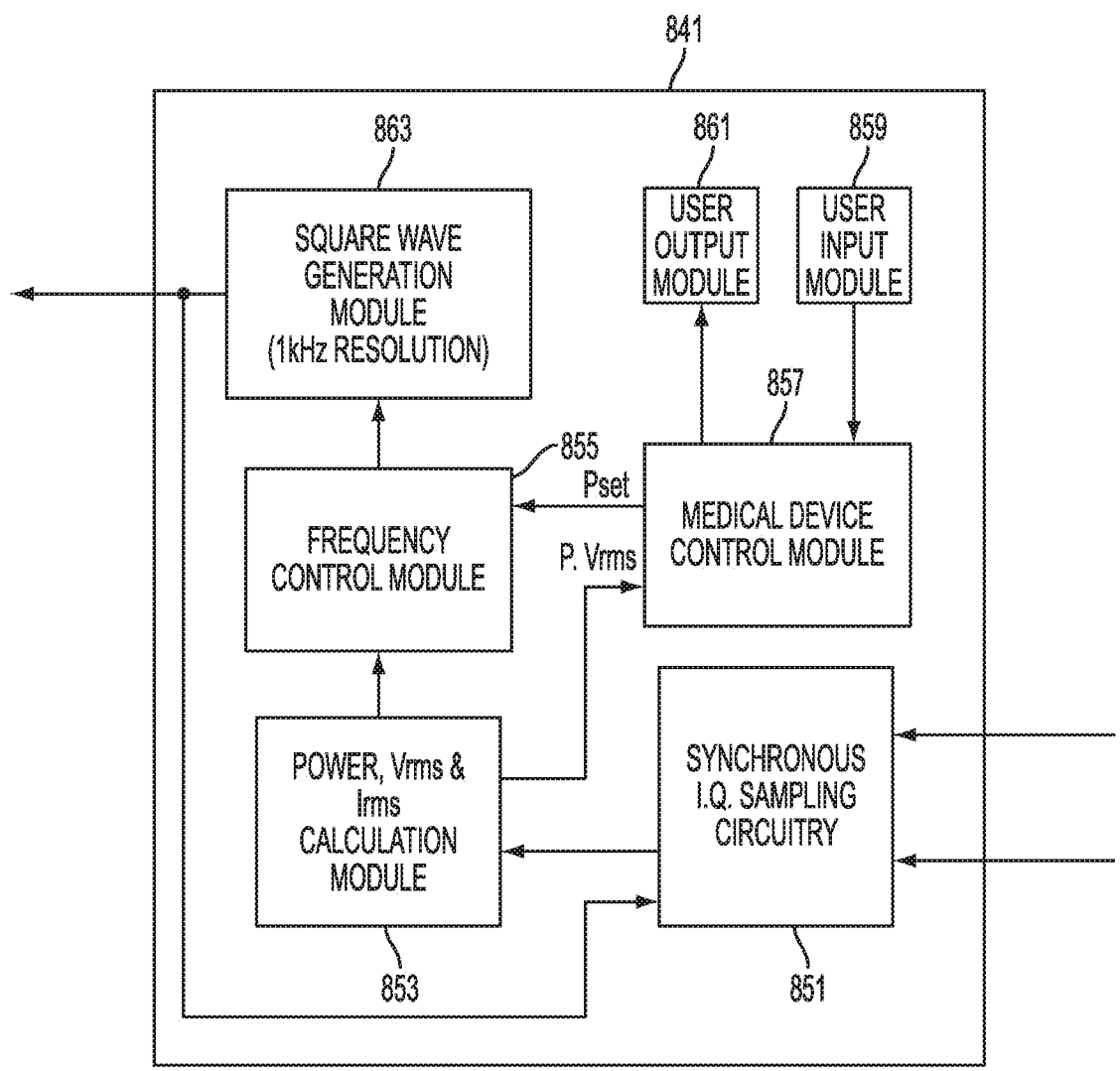
FIG. 17 illustrates the main components of the controller, according to one embodiment.

FIG. 17 illustrates the main components of the controller 841, according to one embodiment. In the embodiment illustrated in FIG. 17, the controller 841 is a microprocessor based controller and so most of the components illustrated in FIG. 3 are software based components. Nevertheless, a hardware based controller 841 may be used instead. As shown, the controller 841 includes synchronous I, Q sampling circuitry 851 that receives the sensed voltage and current signals from the sensing circuitry 843 and 845 and obtains corresponding samples which are passed to a power, $V_{rms}$ and $I_{rms}$ calculation module 853. The calculation module 853 uses the received samples to calculate the RMS voltage and RMS current applied to the load 819 and, from the voltage and current, the power that is presently being supplied to the load 839. The determined values are then passed to a frequency control module 855 and a medical device control module 857. The medical device control module 857 uses the values to determine the present impedance of the load 819 and based on this determined impedance and a pre-defined algorithm, determines what set point power ($P_{set}$) should be applied to the frequency control module 855. The medical device control module 857 is in turn controlled by signals received from a user input module 859 that receives inputs from the user and also controls output devices (lights, a display, speaker or the like) on the handle of the instrument via a user output module 861.

The frequency control module 855 uses the values obtained from the calculation module 853 and the power set point ($P_{set}$) obtained from the medical device control module 857 and predefined system limits (to be explained below), to determine whether or not to increase or decrease the applied frequency. The result of this decision is then passed to a square wave generation module 863 which, in this embodiment, increments or decrements the frequency of a square wave signal that it generates by 1 kHz, depending on the received decision. As those skilled in the art will appreciate, in an alternative embodiment, the frequency control module 855 may determine not only whether to increase or decrease the frequency, but also the amount of frequency change required. In this case, the square wave generation module 863 would generate the corresponding square wave signal with the desired frequency shift. In this embodiment, the square wave signal generated by the square wave generation module 863 is output to the FET gate drive circuitry 805, which amplifies the signal and then applies it to the FET 803-1. The FET gate drive circuitry 805 also inverts the signal applied to the FET 803-1 and applies the inverted signal to the FET 803-2.

FIG. 18 is a signal plot illustrating the switching signals applied to the FETs 803, a sinusoidal signal representing the measured current or voltage applied to the load 819, and the timings when the synchronous sampling circuitry 851 samples the sensed load voltage and load current, according to one embodiment. In particular, FIG. 18 shows the switching signal (labeled PWM1 H) applied to upper FET 803-1 and the switching signal (labeled PWM1 L) applied to lower FET 803-2. Although not illustrated for simplicity, there is a dead time between PWM1 H and PWM1 L to ensure that that both FETs 803 are not on at the same time. FIG. 18 also shows the measured load voltage/current (labeled OUTPUT). Both the load voltage and the load current will be a sinusoidal waveform, although they may be out of phase, depending on the impedance of the load 819. As shown, the load current and load voltage are at the same drive frequency ($f_e$) as the switching Signals (PWM1 H and PWM1 L) used to switch the FETs 803. Normally, when sampling a sinusoidal signal, it is necessary to sample the signal at a rate corresponding to at least twice the frequency of the signal being sampled—i.e. two samples per period. However, as the controller 841 knows the frequency of the switching signals, the synchronous sampling circuit 851 can sample the measured voltage/current signal at a lower rate. In this embodiment, the synchronous sampling circuit 851 samples the measured signal once per period, but at different phases in adjacent periods. In FIG. 18, this is illustrated by the "I" sample and the "Q" sample. The timing that the synchronous sampling circuit 851 makes these samples is controlled, in this embodiment, by the two control signals PWM2 and PWM3, which have a fixed phase relative to the switching signals (PWM1 H and PWM1 L) and are out of phase with each other (preferably by quarter of the period as this makes the subsequent calculations easier). As shown, the synchronous sampling circuit 851 obtains an "I sample on every other rising edge of the PWM2 signal and the synchronous sampling circuit 851 obtains a "0" sample on every other rising edge of the PWM3 signal. The synchronous sampling circuit 851 generates the PWM2 and PWM3 control signals from the square wave signal output by the square wave generator 863 (which is at the same frequency as the switching signals PWM1 H and PWM1 L). Thus control signals PWM2 and PWM3 also change (whilst their relative phases stay the same). In this way, the sampling circuitry 851 continuously changes the timing at which it samples the sensed voltage and current signals as the frequency of the drive signal is changed so that the samples are always taken at the same time points within the period of the drive signal.

Therefore, the sampling circuit 851 is performing a "synchronous" sampling operation instead of a more conventional sampling operation that just samples the input signal at a fixed sampling rate defined by a fixed sampling clock.

The samples obtained by the synchronous sampling circuitry 851 are then passed to the power, $V_{rms}$ and $I_{rms}$ calculation module 853 which can determine the magnitude and phase of the measured signal from just one "I" sample and one "Q" sample of the load current and load voltage. However, in this embodiment, to achieve some averaging, the calculation module 853 averages consecutive "I" samples to provide an average "I" value and consecutive "Q" samples to provide an average "0" value; and then uses the average I and Q values to determine the magnitude and phase of the measured signal (in a conventional manner). As those skilled in the art will appreciate, with a drive frequency of about 400 kHz and sampling once per period means that the synchronous sampling circuit 851 will have a sampling rate of 400 kHz and the calculation module 853 will produce a voltage measure and a current measure every 0.01 ms. The operation of the synchronous sampling circuit 851 offers an improvement over existing products, where measurements can not be made at the same rate and where only magnitude information is available (the phase information being lost).

In one embodiment, the RF amplifier and drive circuitry for the electrosurgical medical instrument employs a resonant mode step-up switching regulator, running at the desired RF electrosurgical frequency to produce the required tissue effect. The waveform illustrated in FIG. 18 can be employed to boost system efficiency and to relax the tolerances required on several custom components in the electronics system 400. In one embodiment, a first generator control algorithm may be employed by a resonant mode switching topology to produce the high frequency, high voltage output signal necessary for the medical instrument. The first generator control algorithm shifts the operating frequency of the resonant mode converter to be nearer or farther from the resonance point in order to control the voltage on the output of the device, which in turn controls the current and power on the output of the device. The drive waveform to the resonant mode converter has heretofore been a constant, fixed duty cycle, with frequency (and not amplitude) of the drive waveform being the only means of control.

FIG. 19 illustrates a drive waveform for driving the FET gate drive circuitry 805, according to one embodiment. Accordingly, in another embodiment, a second generator control algorithm may be employed by a resonant mode switching topology to produce the high frequency, high voltage output signal necessary for the medical instrument. The second generator control algorithm provides an additional means of control over the amplifier in order to reduce power output in order for the control system to track the power curve while maintaining the operational efficiency of the converter. As shown in FIG. 19, according to one embodiment, the second generator control algorithm is configured to not only modulate the drive frequency that the converter is operating at, but to also control the duty cycle of the drive waveform by duty cycle modulation. Accordingly, the drive waveform 890 illustrated in FIG. 19 exhibits two degrees of freedom. Advantages of utilizing the drive waveform 890 modulation include flexibility, improved overall system efficiency, and reduced power dissipation and temperature rise in the amplifier's electronics and passive inductive components, as well as increased battery life due to increased system efficiency.

RF Amplifier Topology

Figure 1:
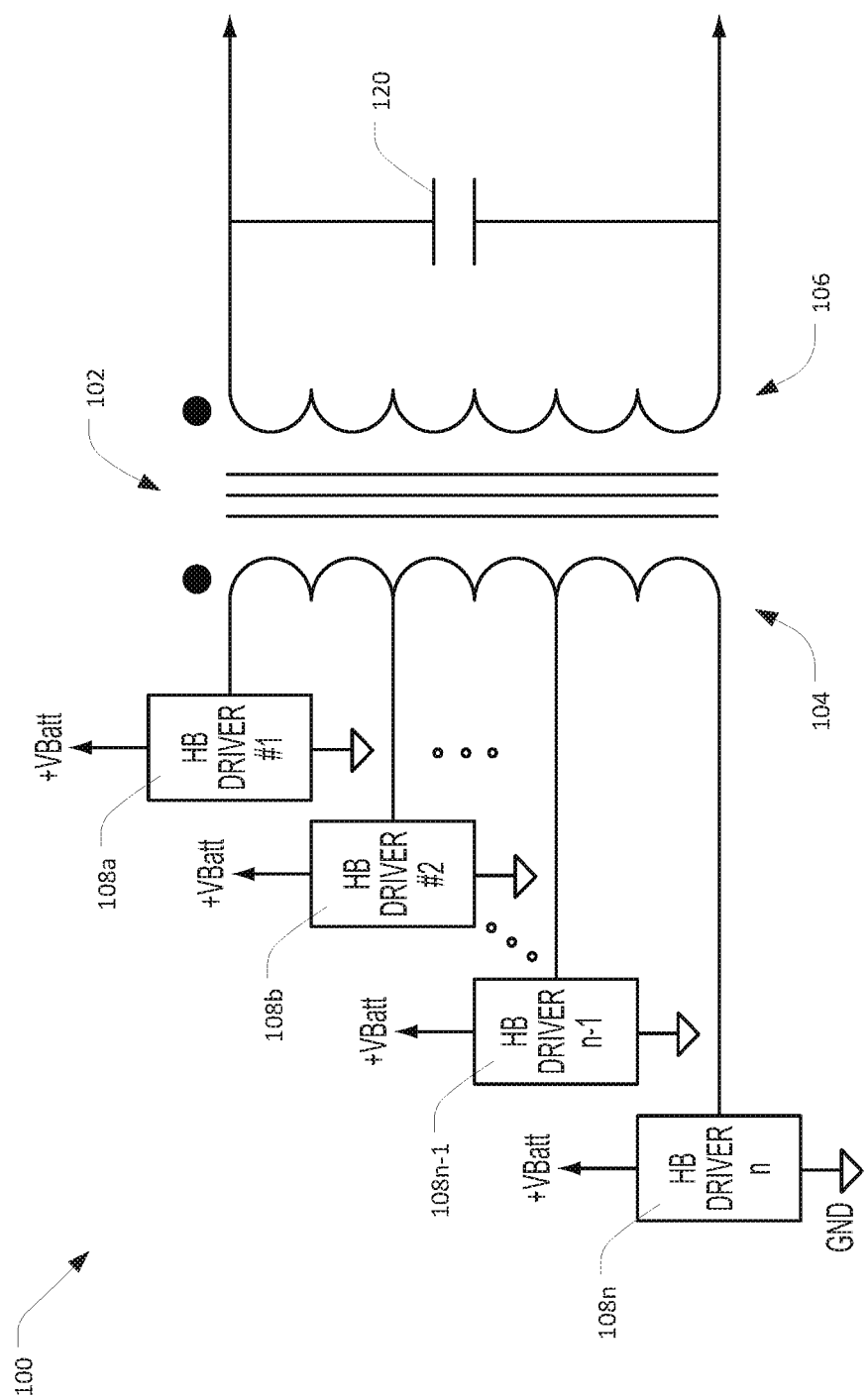
FIG. 1 illustrates one embodiment of an RF amplifier with one or more of taps on the primary coil, wherein each tap is controlled by a half bridge driver.

FIG. 1 illustrates one embodiment of an RF amplifier 100 with one or more of taps on the primary coil 104, wherein each tap is controlled by a half bridge driver 108. As discussed below, each half bridge driver 108 may comprise transistors, MOSFETs, insulated-gate bipolar transistors (IGBTs) or any other suitable switching devices configured in a half bridge drive configuration. The output transformer primary winding 104 may be driven between any two of the half bridge drivers 108, with the number of turns between the half bridge drivers 108 and the fixed output winding 106 determining the overall turns ratio for the transformer 102.

This topology allows for a lower turns ration for high current output on the secondary coil 106 while limiting the primary current to a value that is compatible with currently available lithium-ion (Li-Ion) batteries. For example, a primary current in the range of 20-30 A implies a turns ration of about 4:1. Conversely, when generating a relatively high voltage on the secondary coil 106, for example in the range of 170-250V RMS, it is desirable to have a relatively higher turns ration between the primary coil 104 and the secondary coil 106, for example a ration of about 15:1. This can be accomplished by reducing the number of turns in the primary coil 104 relative to a secondary coil 106 with a fixed number of turns.

This topology provides the ability to dynamically vary the turns ratio, in real time and in sync the output waveform being generated. This is in keeping with a zero-voltage switching (ZVS) or zero current switching (ZCS) methodology for driving the amplifier at its resonant frequency for maximum efficiency and minimum power dissipation in the switching transistors, MOSFETs, IGBTs or other switching devices.

With this topology, the amplifier 100 can also be dynamically driven in a half bridge or a full bridge mode on a output-cycle-by-cycle basis, within a resonant mode drive scheme. This allows for better output regulation.

This topology also provides the ability to match the turns ratio to the region of tissue resistance. This optimizes the losses in the transformer windings by preventing excessive currents in the primary coil 104. It also optimizes the battery voltage required to produce a high voltage on the secondary coil 106 for large-jaw devices and the types of anatomical structures such devices are typically called upon to seal and cut. Multiple turns ratio values may be provided in order to optimize each region or sub-region of the electrosurgical power curve, as necessary.

With this topology the efficiency of the amplifier may be kept arbitrarily close to the optimal value by selection of taps on the primary coil 104.

An arbitrary number of half bridge driver 108 circuits and transformer taps may be provided, tailored to the performance requirements of the particular RF amplifier 100.

Figure 2:
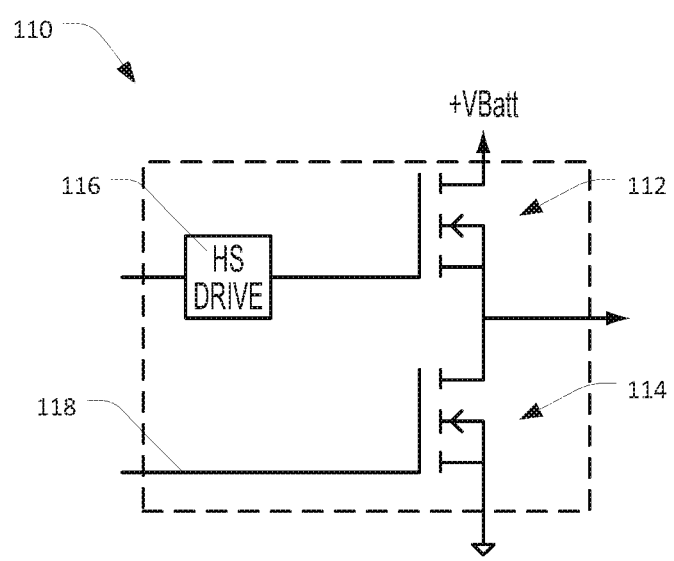
FIG. 2 illustrates one embodiment of a half bridge circuit that may be employed by the half bridge driver.

FIG. 2 illustrates one embodiment of a half bridge circuit 110 that may be employed by the half bridge driver 108. The half bridge circuit 110 comprises an upper switch 112 and a lower switch 114, here illustrated as MOSFETs, wherein the upper 112 and lower 114 switches are connected in a cascade arrangement. The half bridge circuit 110 further comprises an input voltage +VBatt that is provided by the instrument's onboard batteries and a ground return. The half bridge circuit 110 further comprises a high-side gate drive input 116 and a low-side gate drive input 118. The output from the half bridge circuit 110 is at the node between the upper 112 and lower 114 switches. In operation, the switches 112, 114 are turned on and off complementary to each other, with non-overlapping dead time, by applying the correct voltage waveforms at each of the gate drive inputs. This half bridge circuit 110 topology provides for four-quadrant switching, zero-voltage switching (ZVS), zero-current switching (ZCS), high-frequency operation, low EMI, and high efficiency.

While FIG. 2 illustrates a half bridge circuit 110 comprising MOSFET switches, any switch may be used, such as for example transistors, IGBTs or any other suitable switching device.

Furthermore, the design of half bridge circuits is well understood, and any half bridge circuit may be employed in the amplifier topology described above.

Various embodiments of the amplifier 100 as described above may comprise alternate topologies. For example, some embodiments may use solid-state switching elements, such as MOSFETs or other semiconductors that can be similarly controlled. Other embodiments may use physical relays, though physical relays have limitations, including relatively long switching times and arcing that occurs at the contacts when they are switched, caused because it is not possible to switch mechanical relays at a current or voltage zero crossing at the primary coil 104 or secondary coil 106. Arcing is an issue for designs that are intended to be reprocessed and reused.

FIG. 1 illustrates on embodiment of an amplifier 100 with a parallel resonant output section, comprising a parallel capacitor 120. Such an amplifier 100 is intended to produce a relatively pure sine wave as an output. The parallel capacitor 120 that forms the other half of the resonant tank circuit, with the transformer secondary inductance and leakage inductance, may be omitted, to produce a square wave approximate output waveform. when a peak-detector type of circuit is used for output voltage and current sensing, then issues with higher Nyquis rate sampling on the output may be avoided: the output pseudo-square wave will contain significant energy at the third, fifth, seventh and ninth harmonics, which will distort the output measurements if the A/D converter in the design does not have adequate bandwidth to sample these harmonics and keep them from aliasing. A lowpass anti-aliasing filter and software linearization (correction) for measured quantities could also be contemplated as solutions to reduce the Nyquist rate sampling rate required to avoid aliasing.

It is worthy to note that any reference to "one aspect," "an aspect," "one embodiment," or "an embodiment" means that a particular feature, structure, or characteristic described in connection with the aspect is included in at least one aspect. Thus, appearances of the phrases "in one aspect," "in an aspect," "in one embodiment," or "in an embodiment" in various places throughout the specification are not necessarily all referring to the same aspect. Furthermore, the particular features, structures or characteristics may be combined in any suitable manner in one or more aspects.

Although various embodiments have been described herein, many modifications, variations, substitutions, changes, and equivalents to those embodiments may be implemented and will occur to those skilled in the art. Also, where materials are disclosed for certain components, other materials may be used. It is therefore to be understood that the foregoing description and the appended claims are intended to cover all such modifications and variations as falling within the scope of the disclosed embodiments. The following claims are intended to cover all such modification and variations.

Although various embodiments have been described herein, many modifications, variations, substitutions, changes, and equivalents to those embodiments may be implemented and will occur to those skilled in the art. Also, where materials are disclosed for certain components, other materials may be used. It is therefore to be understood that the foregoing description and the appended claims are intended to cover all such modifications and variations as falling within the scope of the disclosed embodiments. The following claims are intended to cover all such modification and variations.

What is claimed is:

1. A control circuit for a radio frequency drive of an electrosurgical device, the control circuit comprising:
    a voltage data input configured to receive voltage data from a voltage sensing circuit;
    a current data input configured to receive current data from a current sensing circuit; and
    a switching signal output configured to source a switching signal to the radio frequency drive of the electrosurgical device,
    wherein the control circuit is configured to adjust a frequency of the switching signal based on the voltage data and the current data, and
    wherein the radio frequency drive comprising a transformer, wherein the transformer comprises:
        a first tap including a first half bridge driver;
        a second tap including a second half bridge driver;
        a third tap including a third half bridge driver;
        a first portion of a primary coil located between the first tap and the second tap;
        a second portion of the primary coil located between the second tap and the third tap; and
        a secondary coil, wherein the first, second, and third half bridge drivers are configured to selectively turn on or turn off the first, second, and third taps, respectively,
        wherein two of the first, second, and third taps are selected to drive the primary coil between the two selected taps, which allows the transformer to provide a plurality of winding ratio values, wherein a number of coil turns of the primary coil between the two selected taps and a number of coil turns of the secondary coil determine an overall winding ratio value of the transformer,
        wherein the overall winding ratio value is one of the plurality of winding ratio values provided by the transformer.

2. The control circuit of claim 1, further comprising a synchronous I/Q sampling circuit, configured to sample the voltage data and to sample the current data.

3. The control circuit of claim 2, wherein the synchronous I/Q sampling circuit is configured to sample the voltage data and the current data based on a period of the switching signal.

4. The control circuit of claim 3, wherein the synchronous I/Q sampling circuit is configured to sample the voltage data and to sample the current data once per period of the switching signal at a first phase of a first period of the switching signal, and at a second phase of an adjacent period of the switching signal.

5. The control circuit of claim 3, wherein the synchronous I/Q sampling circuit is configured to sample the voltage data and to sample the current data in-phase with and in-quadrature to the switching signal.

6. The control circuit of claim 5, further comprising a power calculation circuit configured to calculate a power value, an RMS voltage value, and an RMS current value based on the sampled voltage data and the sampled current data.

7. The control circuit of claim 6, wherein the power calculation circuit is configured to calculate the RMS voltage value from an average of successive in-phase samples of the voltage data and an average of successive in-quadrature samples of the voltage data, and
   wherein the power calculation circuit is configured to calculate the RMS current value from an average of successive in-phase samples of the current data and an average of successive in-quadrature samples of the current data.

8. The control circuit of claim 6, further comprising a square wave generation module in data communication with the switching signal output and is configured to generate the switching signal.

9. The control circuit of claim 8, wherein the square wave generation module has a frequency resolution of 1 kHz.

10. The control circuit of claim 8, wherein the square wave generation module is configured to adjust a frequency of the switching signal based at least in part on the RMS voltage value, the RMS current value, and the power value.

11. The control circuit of claim 10, wherein the square wave generation module is configured to increase a frequency of the switching signal or decrease the frequency of the switching signal.

12. A method of controlling a radio frequency drive circuit of an electrosurgical device, the method comprising:
   sampling, by a synchronous I/Q sampling circuit, a plurality of output voltage values of an output voltage of the electrosurgical device;
   sampling, by the synchronous I/Q sampling circuit, a plurality of output current values of an output current of the electrosurgical device; and
   sourcing, by a square wave generation module, a switching signal to drive the radio frequency drive circuit,
   wherein the output voltage and the output current are sourced by the radio frequency drive circuit comprising a transformer, wherein the transformer further comprises:
   a first tap including a first half bridge driver;
   a second tap including a second half bridge driver;
   a third tap including a third half bridge driver;
   a first portion of a primary coil located between the first tap and the second tap;
   a second portion of the primary coil located between the second tap and the third tap; and
   a secondary coil, wherein the first, second, and third half bridge drivers are configured to selectively turn on or turn off the first, second, and third taps, respectively,
   wherein two of the first, second, and third taps are selected to drive the primary coil between the two selected taps, which allows the transformer to provide a plurality of winding ratio values, wherein a number of coil turns of the primary coil between the two selected taps and a number of coil turns of the secondary coil determine an overall winding ratio value of the transformer, wherein the overall winding ratio value is one of the plurality of winding ratio values provided by the transformer.

13. The method of claim 12 further comprising, adjusting, by the square wave generation module, a frequency of the switching signal.

14. The method of claim 13, wherein adjusting, by the square wave generation module, a frequency of the switching signal comprises adjusting, by the square wave generation module, a frequency of the switching signal to a resolution of 1 kHz.

15. The method of claim 13, wherein adjusting, by the square wave generation module, a frequency of the switching signal comprises adjusting, by the square wave generation module, a frequency of the switching signal based at least in part on the plurality of sampled output voltage values and the plurality of sampled output current values.

16. The method of claim 12, wherein sampling, by a synchronous I/Q sampling circuit, a plurality of output voltage values comprises sampling, by the synchronous I/Q sampling circuit, a plurality of output voltage values based on a period of the switching signal, and
   wherein sampling, by a synchronous I/Q sampling circuit, a plurality of output current values comprises sampling, by the synchronous I/Q sampling circuit, a plurality of output current values based on the period of the switching signal.

17. The method of claim 12, wherein sampling, by a synchronous I/Q sampling circuit, a plurality of output voltage values comprises sampling, by the synchronous I/Q sampling circuit, a plurality of output voltage values in-phase with and in-quadrature to the switching signal, and
   wherein sampling, by a synchronous I/Q sampling circuit, a plurality of output current values comprises sampling, by a synchronous I/Q sampling circuit, a plurality of output current values in-phase with and in-quadrature to the switching signal.

18. The method of claim 12, further comprising calculating, by a power calculation circuit, an RMS voltage value, and an RMS current value based on the output voltage values and the output current values.

19. The method of claim 18, further comprising, adjusting, by the square wave generation module, a frequency of the switching signal based at least in part on the RMS voltage value and the RMS current value.

* * * * *